United States Patent [19]

Farbood et al.

[11] Patent Number: 4,946,782

[45] Date of Patent: Aug. 7, 1990

[54] PROCESS FOR PREPARING COMPOSITIONS CONTAINING UNSATURATED LACTONES, PRODUCTS PRODUCED THEREBY AND ORGANOLEPTIC USES OF SAID PRODUCTS

[75] Inventors: Mohamad I. Farbood, Holmde; James A. Morris, Belmar; Mark A. Sprecker, Sea Bright; Lynda J. Bienkowski, Perth Amboy; Kevin P. Miller, Middletown; Manfred H. Vock, Locust; Myrna L. Hagedorn, Edison, all of N.J.

[73] Assignee: International Flavors & Fragrances Inc., New York, N.Y.

[21] Appl. No.: 228,512

[22] Filed: Aug. 5, 1988

[51] Int. Cl.$^5$ .................. C12P 17/04; C12P 17/02; C12P 17/08; C12N 1/16
[52] U.S. Cl. ................................ 435/126; 435/124; 435/123; 435/255
[58] Field of Search .............. 435/123, 124, 126, 921, 435/255

[56] References Cited

U.S. PATENT DOCUMENTS 4,560,656  12/1985  Farbood et al. .

FOREIGN PATENT DOCUMENTS 0258993  3/1988  European Pat. Off. .
8301072  3/1983  PCT Int'l Appl. .

OTHER PUBLICATIONS

Okui et al., *The Journal of Biochemistry*, vol. 54, No. 6, 1963, pp. 536–540.

Primary Examiner—Elizabeth C. Weimar
Assistant Examiner—Irene Marx
Attorney, Agent, or Firm—Arthur L. Liberman

[57] ABSTRACT

Described is a process for the preparation of compositions of matter containing unsaturated lactones defined according to the generic structure:

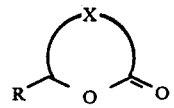

wherein R represents $C_6$ alkyl or alkenyl; and X represents $C_2$, $C_4$ or $C_6$ alkylene or alkenylene; with the provisos that R is $C_6$ alkyl when X is alkenylene and R is $C_6$ alkenyl when X is alkylene by means of the sequential steps of (i) fermentation of castor oil or ricinoleic acid using a microorganism selected from the group consisting of:

*Candida petrophilum*, ATCC 20226;
*Candida oleophila*, ATCC 20177;
*Candida sp.*, ATCC 20504; and
*Candida sake*, ATCC 28137 whereby gamma hydroxydecanoic acid and a mixture of other acids defined according to the generic structure:

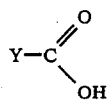

is formed wherein Y represents an oxo-saturated, oxo-unsaturated or di-unsaturated $C_9$, $C_{11}$ or $C_{13}$ moiety according to the reaction:

(Abstract continued on next page.)

-continued

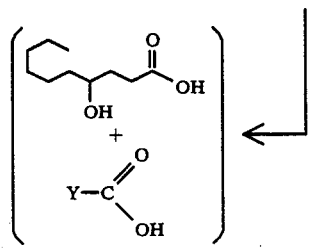

(ii) lactonization of the resulting gamma hydroxydecanoic acid by means of simultaneous acidification and heating according to the reaction:

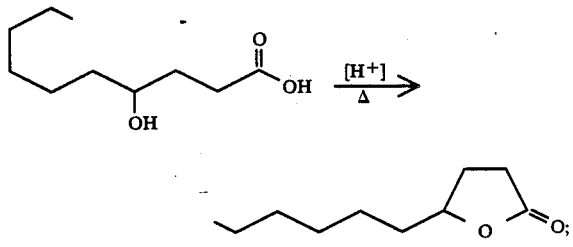

and (iii) lactonization (via distillation) of one or more of the resulting acids defined according to the structure:

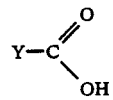

to form one or more lactones defined according to the generic structure:

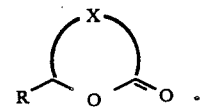

according to the reaction:

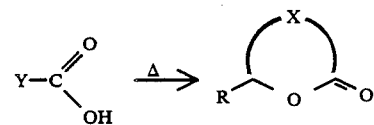

wherein the sum of the number of carbon atoms in the X moiety and in the R moiety is equal to the number of carbon atoms in the Y moiety minus 1.

Also described are the products produced according to such process as well as their organoleptic utilities for augmenting or enhancing the aroma or taste of consumable materials selected from the group consisting of perfume compositions, colognes, perfumed articles, foodstuffs, chewing gums, medicinal products, toothpastes, chewing tobaccos and smoking tobaccos.

1 Claim, 19 Drawing Sheets

GLC PROFILE FOR EXAMPLE I.

GLC PROFILE FOR EXAMPLE I.

GLC PROFILE FOR EXAMPLE II.

GLC PROFILE FOR EXAMPLE II.

GLC PROFILE FOR EXAMPLE III

GLC PROFILE FOR FRACTION 23 OF EXAMPLE V.

GLC PROFILE FOR FRACTION 24 OF EXAMPLE V.

GLC PROFILE FOR FRACTION I OF EXAMPLE V.

MASS SPECTRUM

PMR SPECTRUM

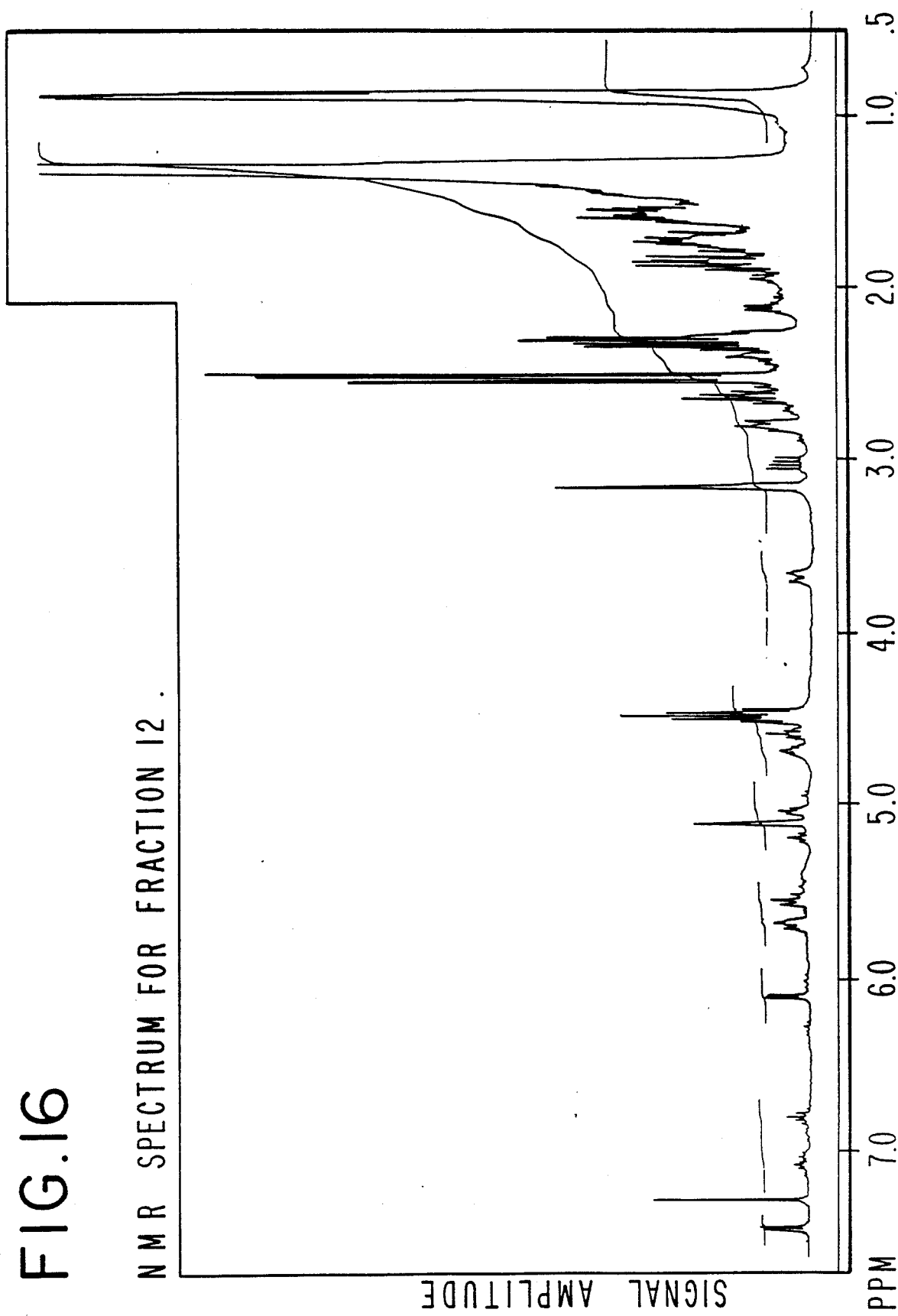
FIG. 16 NMR SPECTRUM FOR FRACTION 12.

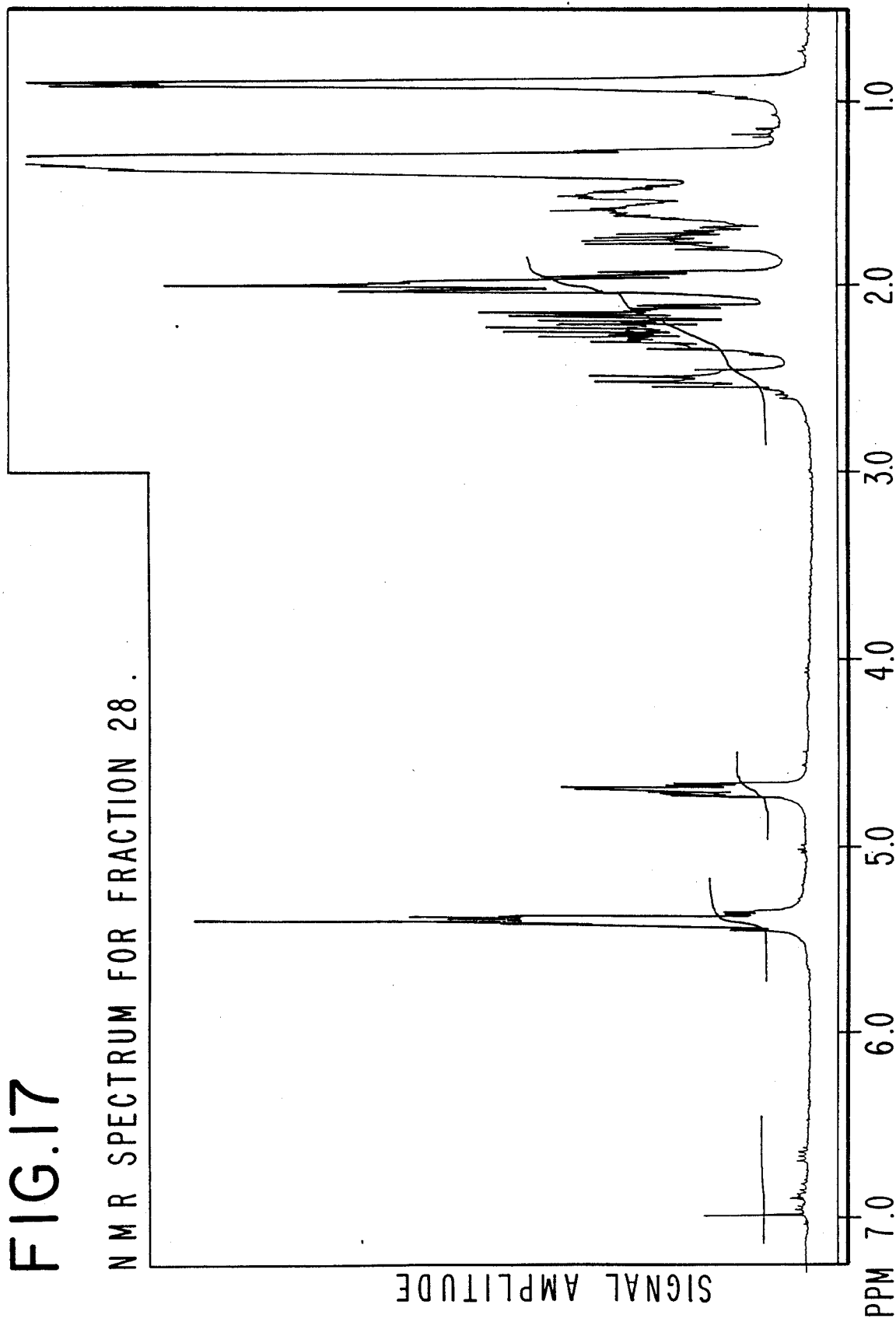
FIG. 17 NMR SPECTRUM FOR FRACTION 28.

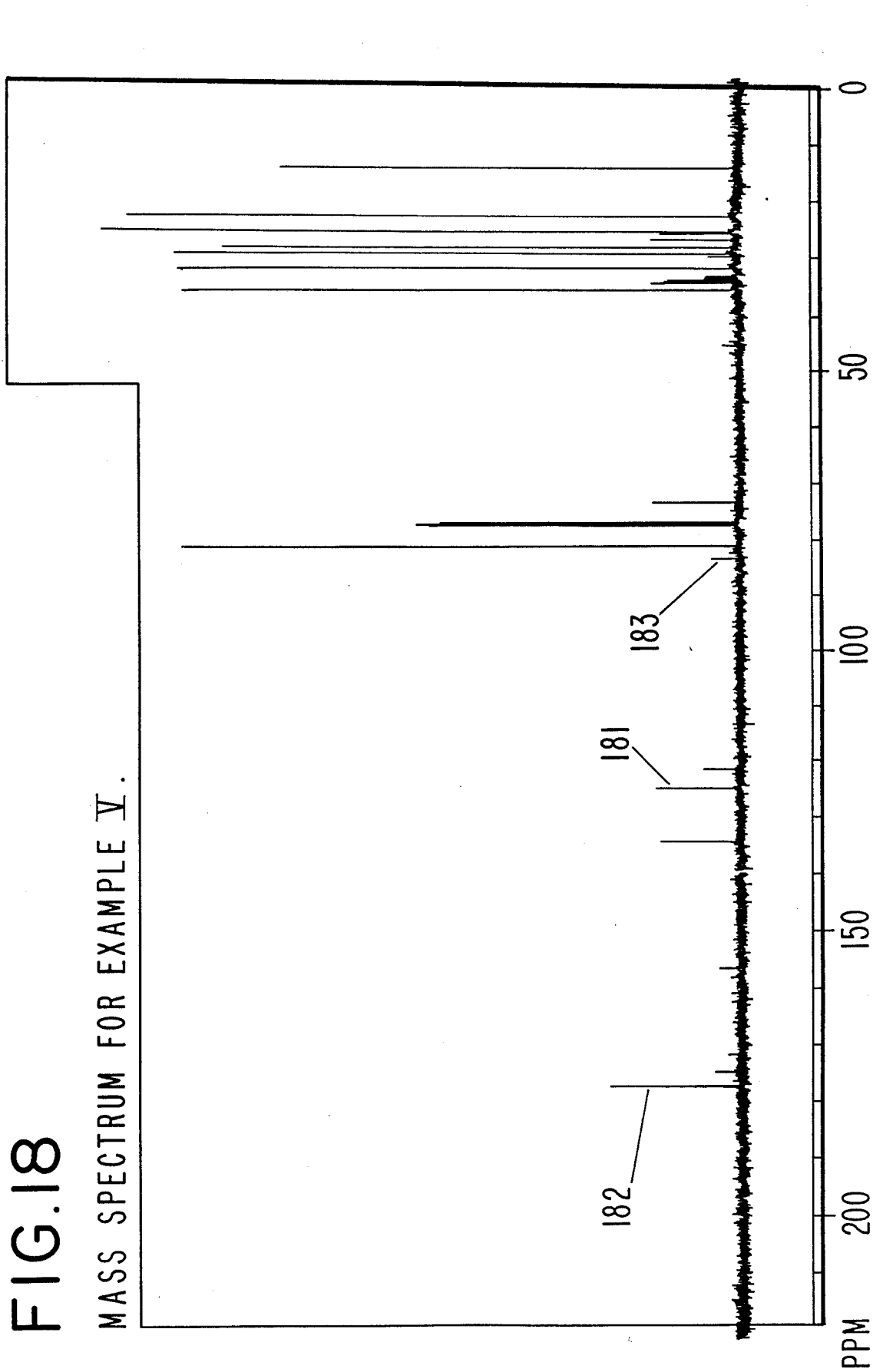
FIG. 18 MASS SPECTRUM FOR EXAMPLE V.

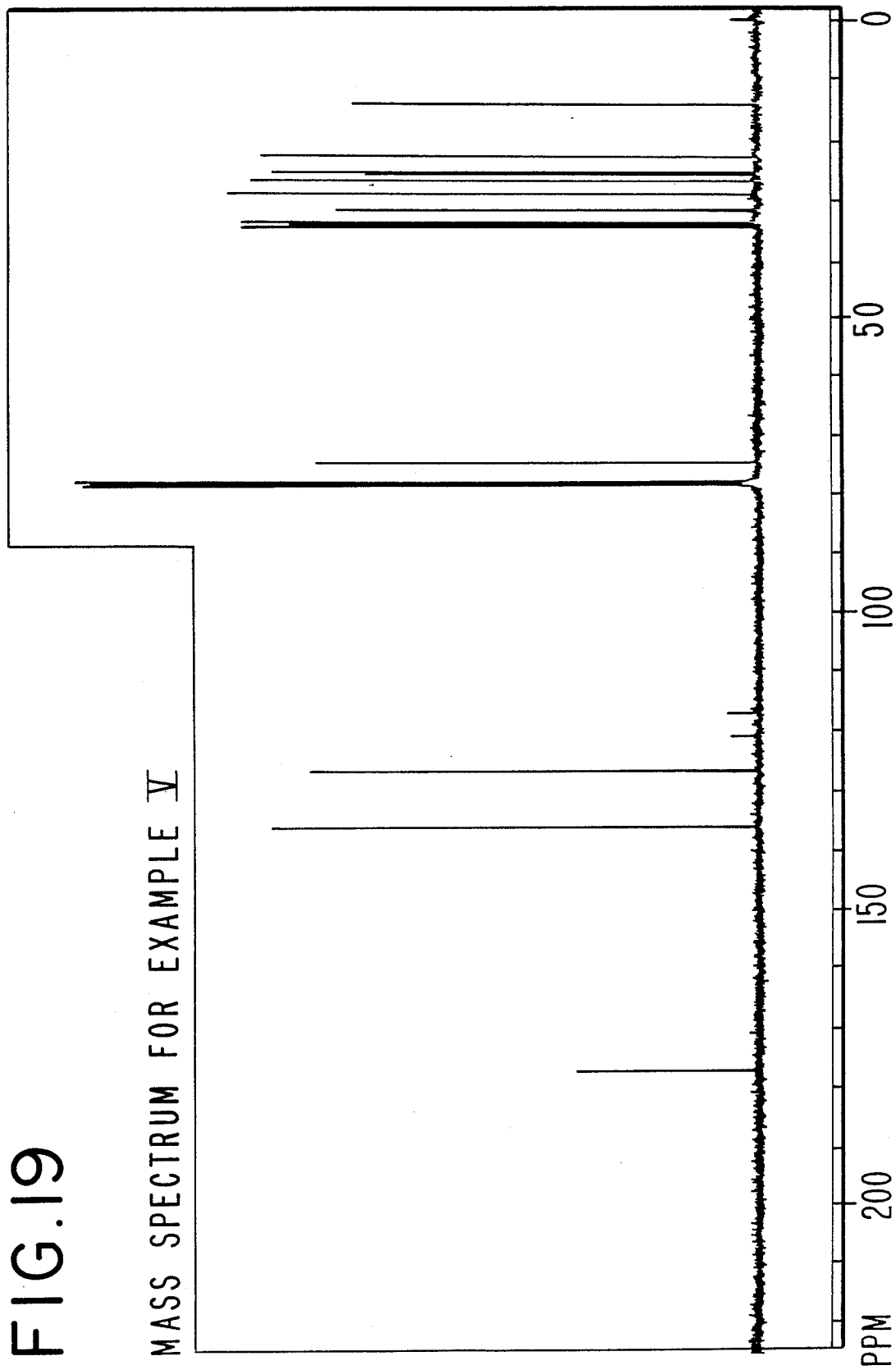

PROCESS FOR PREPARING COMPOSITIONS CONTAINING UNSATURATED LACTONES, PRODUCTS PRODUCED THEREBY AND ORGANOLEPTIC USES OF SAID PRODUCTS

BACKGROUND OF THE INVENTION

This invention is concerned with a microbial process for the production of compositions of matter containing unsaturated lactones.

Considerable time and effort have been expended by microbiologists in the search for better processes for the production of unsaturated lactones; and more generally lactones per se. U.S. Pat. No. 3,076,750 discloses a method of preparing certain optically active lactones and the corresponding hydroxycarboxylic acids by microbial reduction of ketocarboxylic acids. The metabolism of ricinoleic acid by some Candida strains was investigated by Okui, et al (J. Biochemistry, 54, 536–540, 1963) who showed that gamma hydroxydecanoic acid was an intermediate in the oxidative degradation of ricinoleic acid. However, only trace amounts of gamma hydroxydecanoic acid were recovered from the fermentation medium due to the metabolysis of gamma hydroxydecanoic acid upon completion of the fermentation, and the toxicity of ricinoleic acid to the microorganism, which limits the amount of substrate that can be used.

U.S. Pat. No. 4,560,656 provided a method of producing optically active gamma hydroxydecanoic acid comprising culturing or incubating a microorganism capable of hydrolyzing castor oil, and effecting beta-oxidation of the resulting hydrolysate in the presence of castor oil, to produce gamma hydroxydecanoic acid.

U.S. Pat. No. 4,560,656 also provided a method of producing optically active gamma hydroxydecanoic acid comprising enzymatically hydrolyzing castor oil using lipase to form an enzymatic hydrolysate and culturing or incubating a microorganism capable of effecting beta-oxidation of the enzymatic hydrolysate in the presence of said hydrolysate to produce gamma hyroxydecanoic acid.

U.S. Pat. No. 4,560,656 also provided a method of producing optically active gamma hydroxydecanoic acid comprising culturing or incubating a microorganism capable of hydrolyzing castor oil and a microorganism capable of effecting beta-oxidation of castor oil hydrolysate in the presence of castor oil to produce gamma hydroxydecanoic acid.

European Published Patent Application 258993 published on Apr. 9, 1988 discloses a process for the production of optically active gamma hydroxydecanoic acid suitable for conversion to optically active gamma decalactone. The process cover steps of:
(a) culturing *Sporobolomyces odorous;* and/or *Rhodotorula glutinis* on a medium containing a ricinoleic acid source at 15°–35° C. at a pH of 3–9 and optionally; and
(b) lactonizing the resulting gamma hydroxydecanoic acid to gamma decalactone.

Nothing in the prior art however discloses the ability by means of fermentation to create a novel mixture of unsaturated lactones together with, optionally, gamma decalactone found to be useful in augmenting or enhancing the organoleptic properties of consumable materials.

In the flavor and fragrance art, a need has arisen for the development and efficient production of naturally occurring lactones which have heretofor been found to be useful and necessary in the creation of flavor formulations used in augmenting or enhancing the aroma or taste of foodstuffs, chewing gums, toothpastes, medicinal products, chewing tobaccos and smoking tobaccos and also useful in augmenting or enhancing the aroma of perfume compositions, colognes and perfumed articles (e.g., solid or liquid anionic, cationic, nonionic or zwitterionic detergents, perfumed polymers, fabric softener compositions, fabric softener articles, hair preparations, cosmetic powders and the like).

Although U.S. Pat. No. 4,560,656 has partially fulfilled the need for provision of saturated gamma decalactone defined according to the structure:

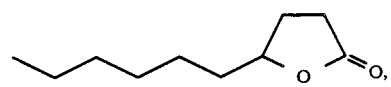

nothing in the prior art sets forth the creation of unsaturated lactones defined generically according to the structure:

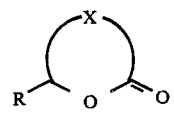

and defined more specifically according to the structures:

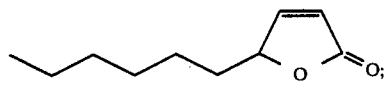

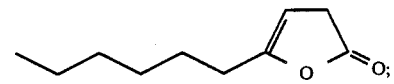

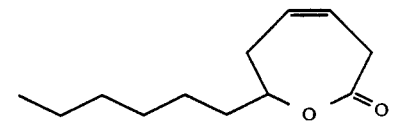

and

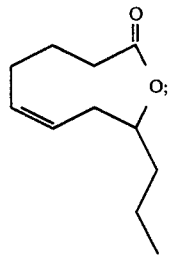

-continued

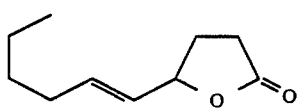

and

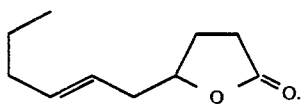

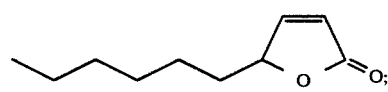

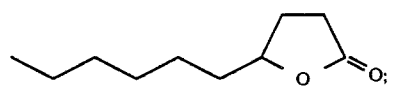

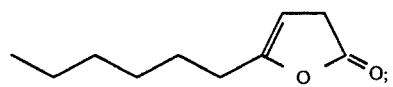

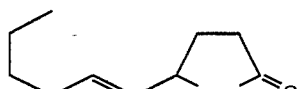

and

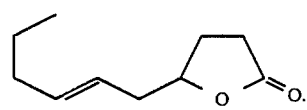

Figure 2:
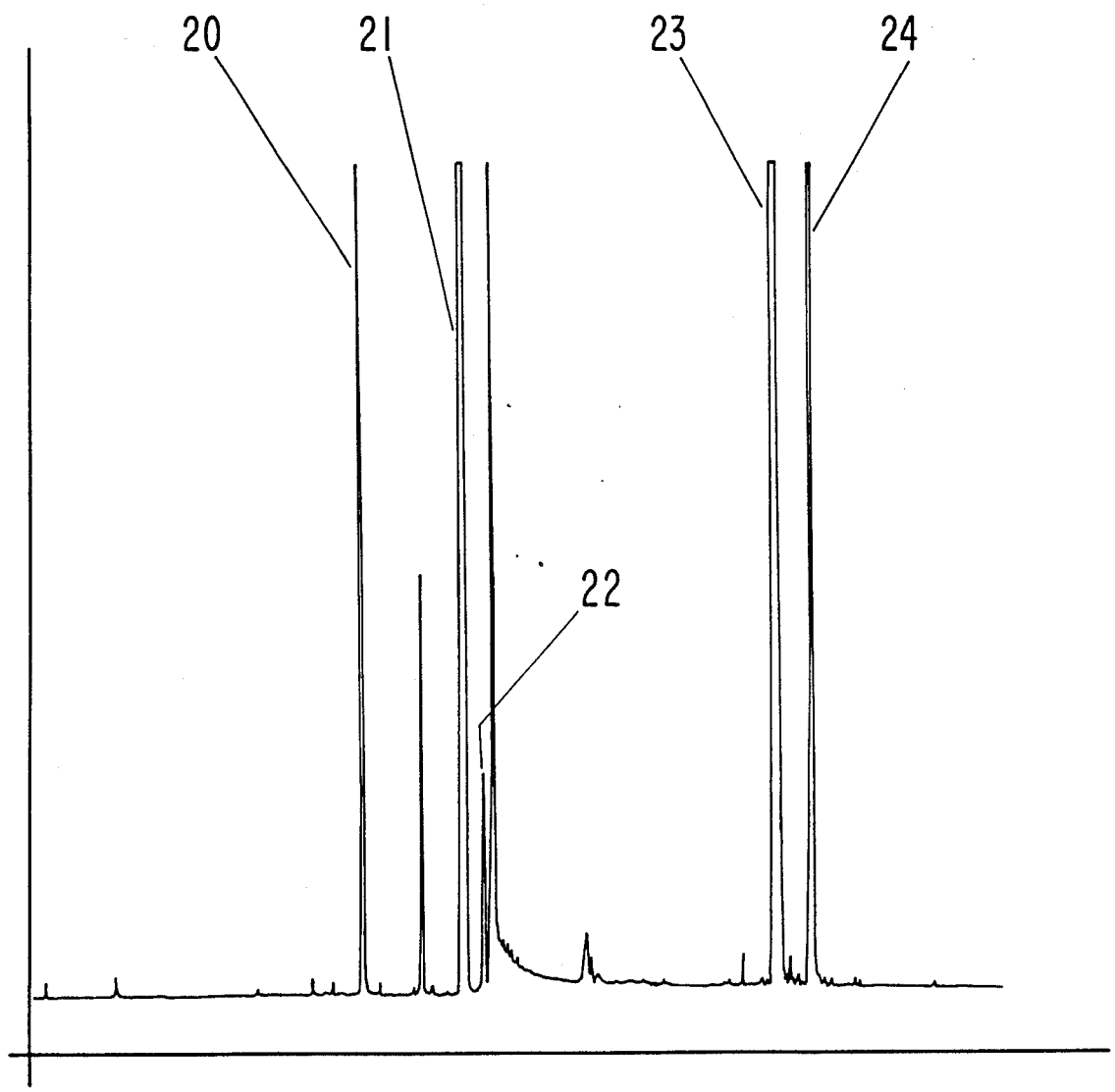

FIG. 2 is the GLC profile for the reaction product of Example I containing the compounds having the structures:

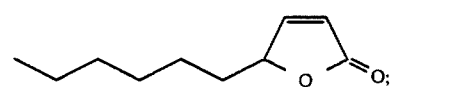

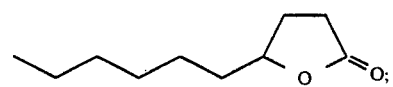

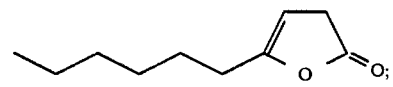

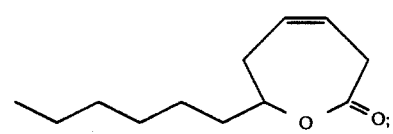

-continued

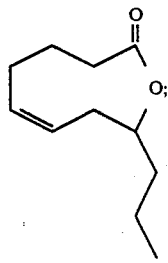

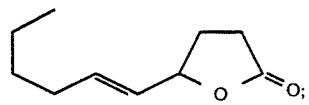

and

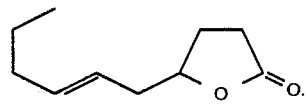

Figure 3:
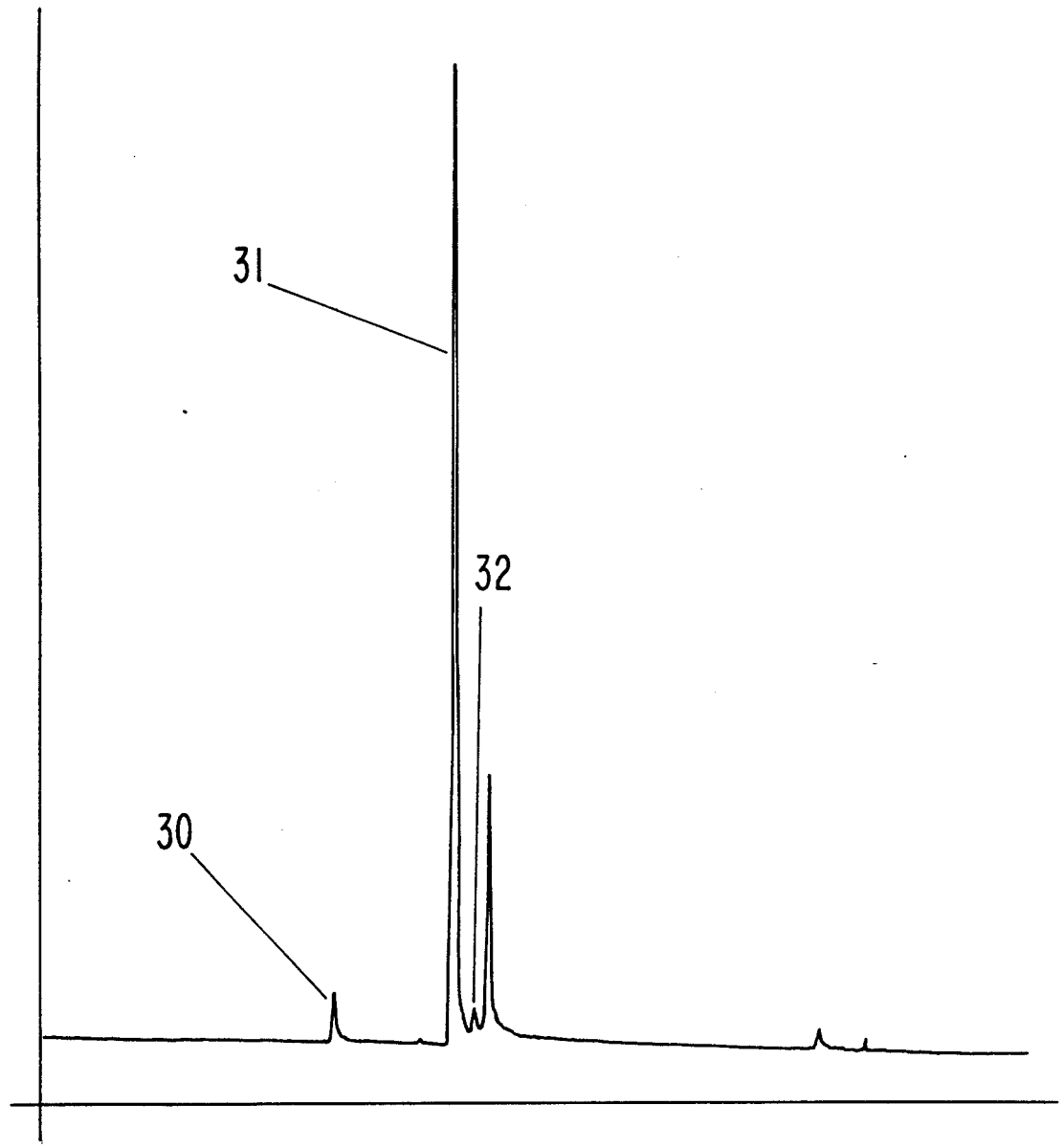

FIG. 3 is the GLC profile for the reaction product of Example II containing the compounds having the structures:

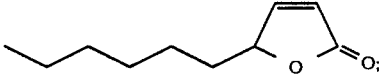

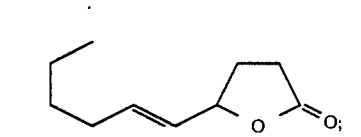

and

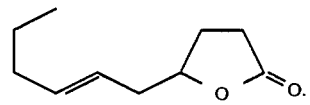

Figure 4:
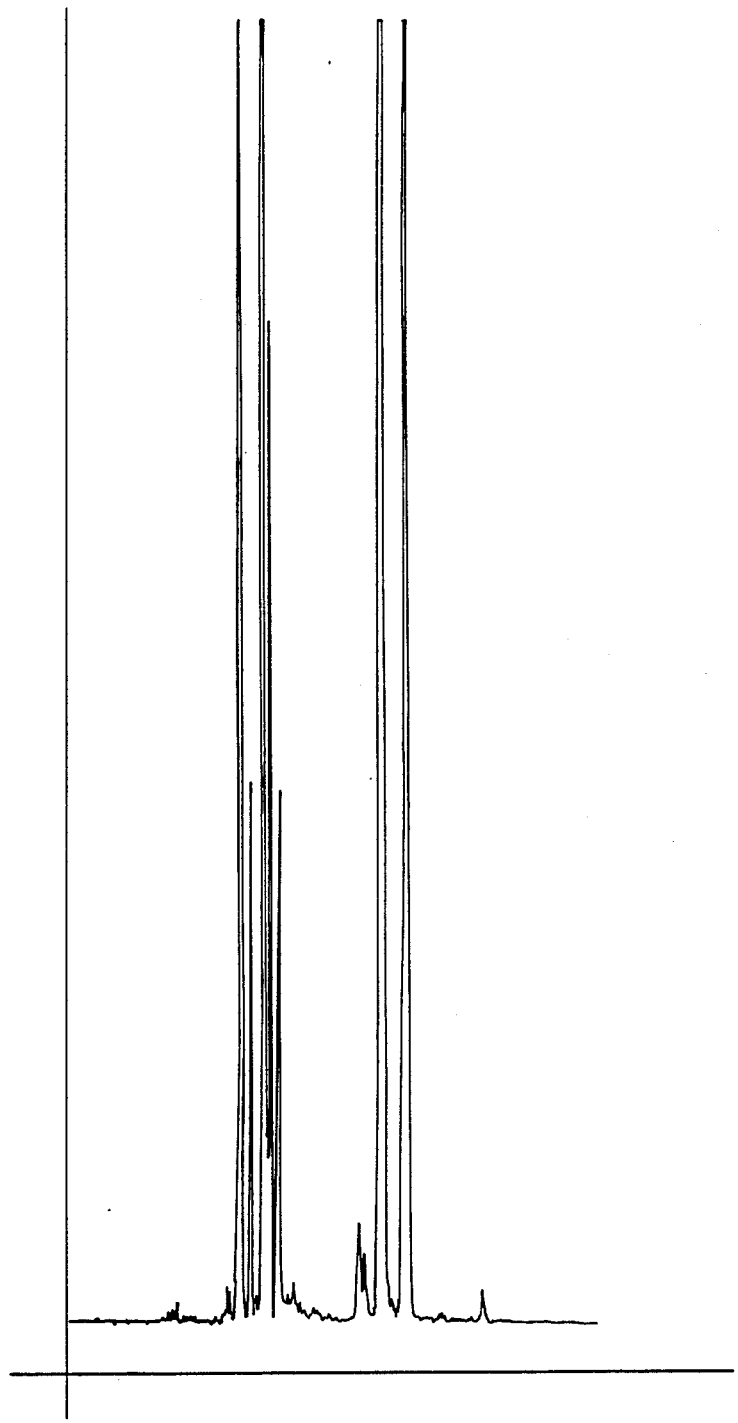

FIG. 4 is the GLC profile for Fraction 19 of the distillation of the reaction product of Example II.

Figure 5:
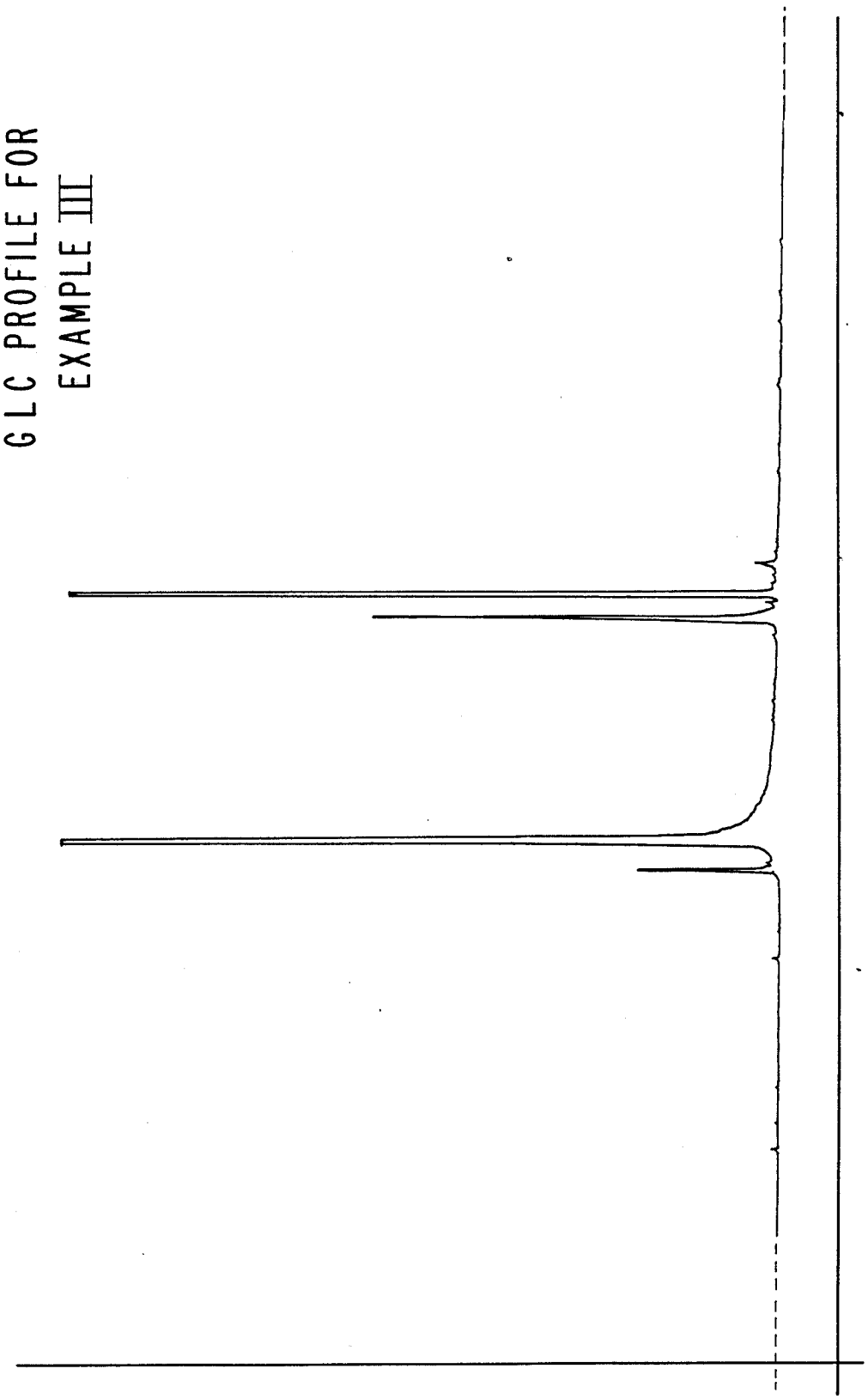

FIG. 5 is the GLC profile for the reaction product of Example III.

Figure 6:
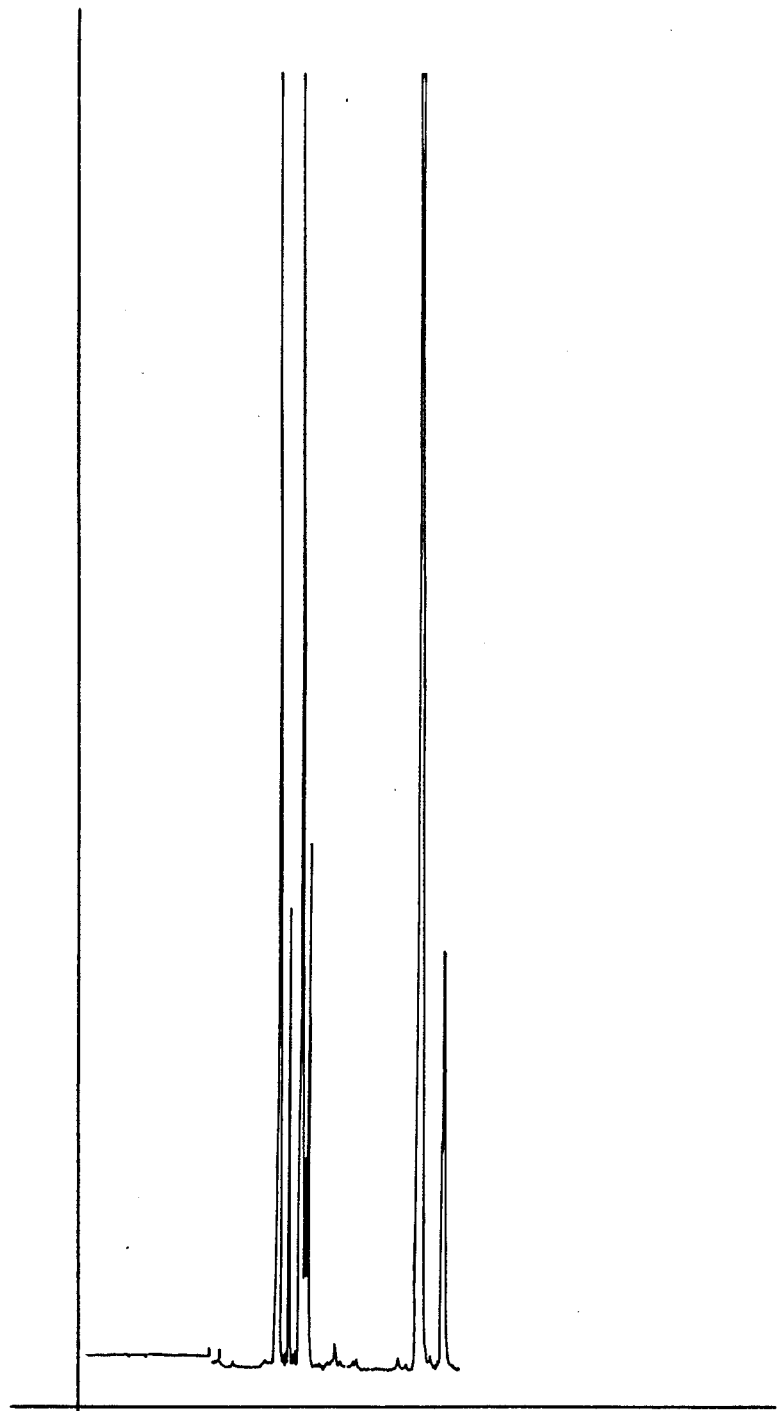

FIG. 6 is the GLC profile for Fraction 23 of the distillation of the reaction product of Example V.

Figure 7:
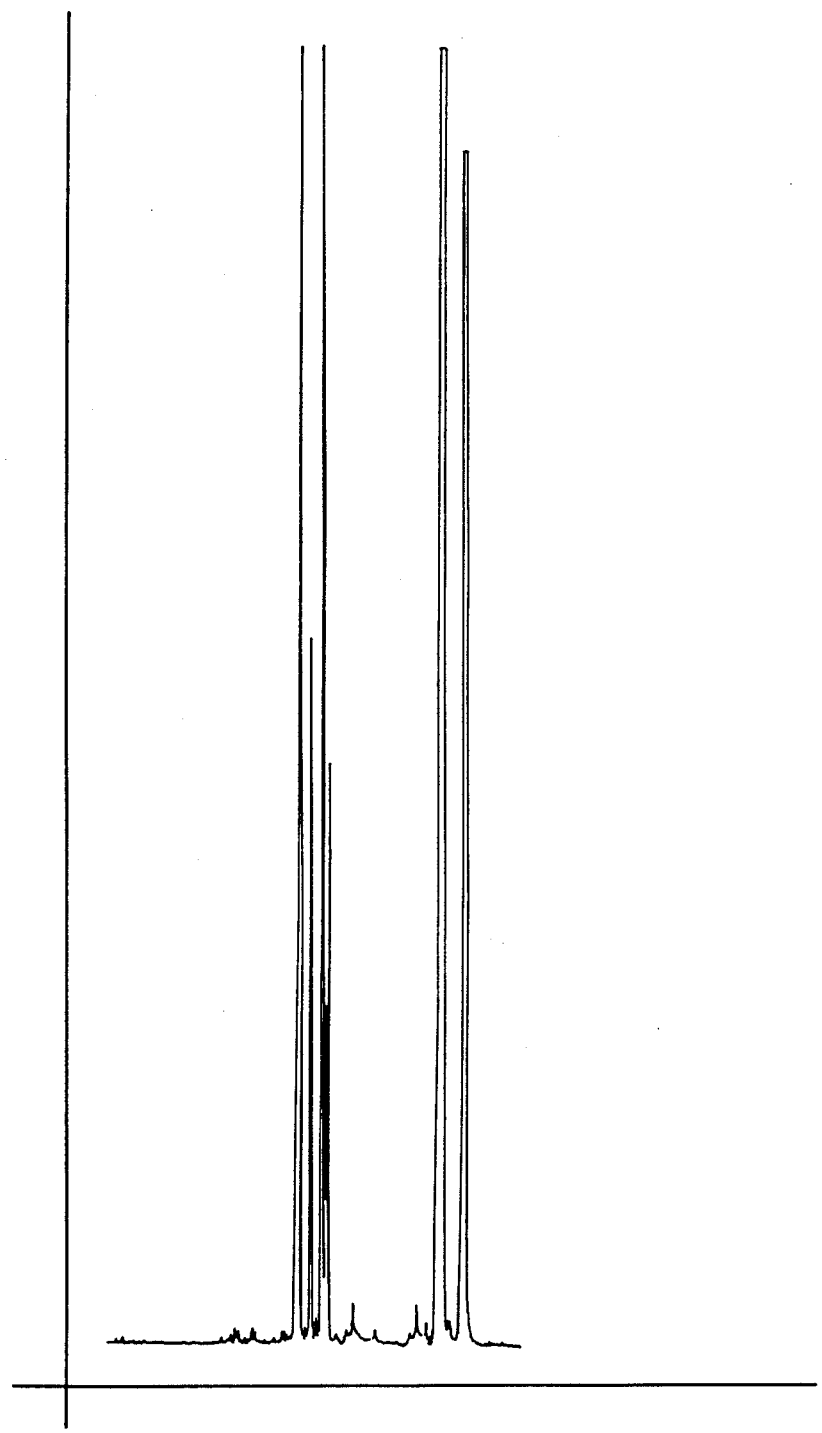

FIG. 7 is the GLC profile for Fraction 24 of the distillation of the reaction product of Example V.

Figure 8:
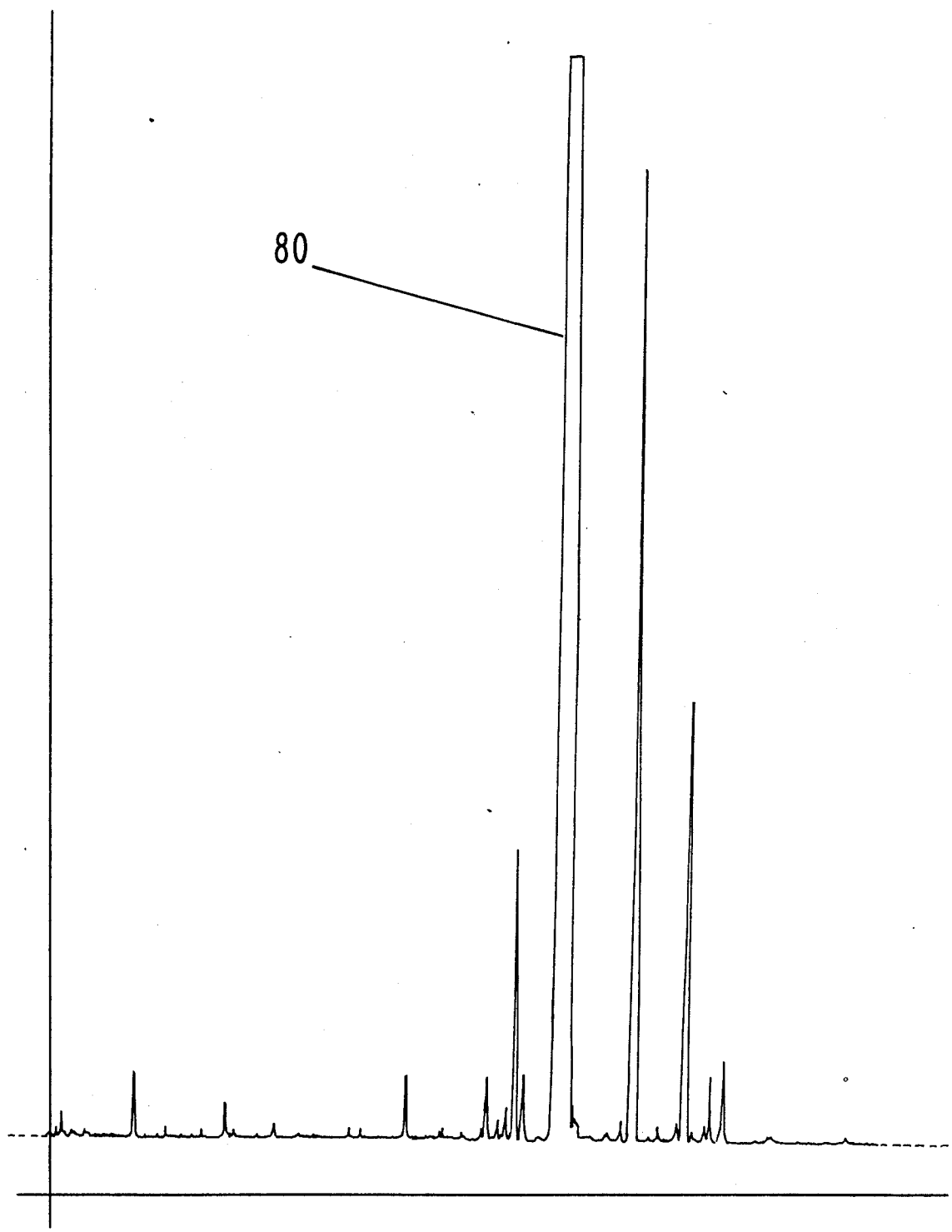

FIG. 8 is the GLC profile for Fraction 1 of the distillation of the reaction product of Example V containing the compound having the structure:

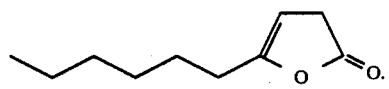

Figure 9:
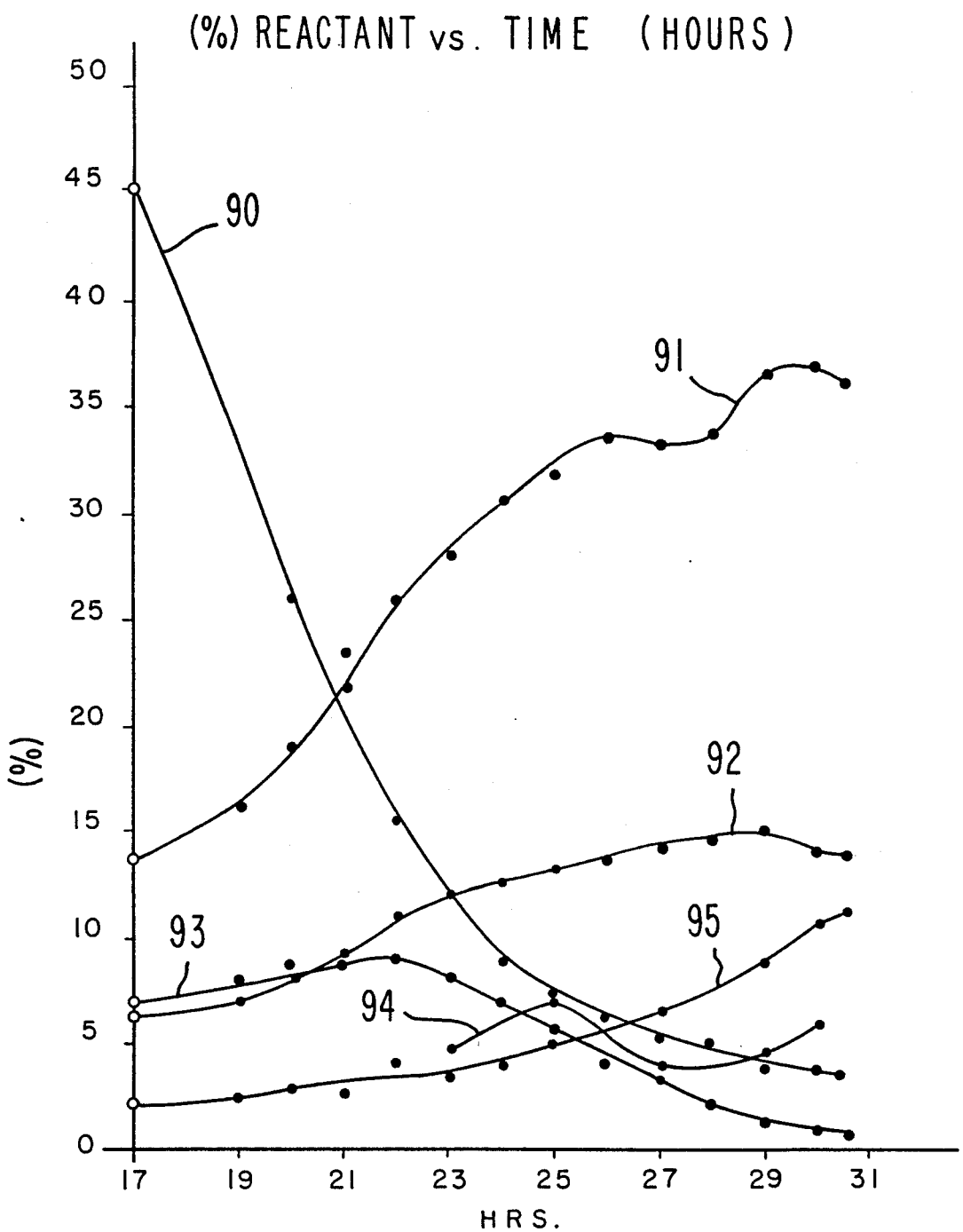

FIG. 9 is a series of graphs showing percent reactant versus time (hours) for the reaction carried out in Example V.

Figure 10:
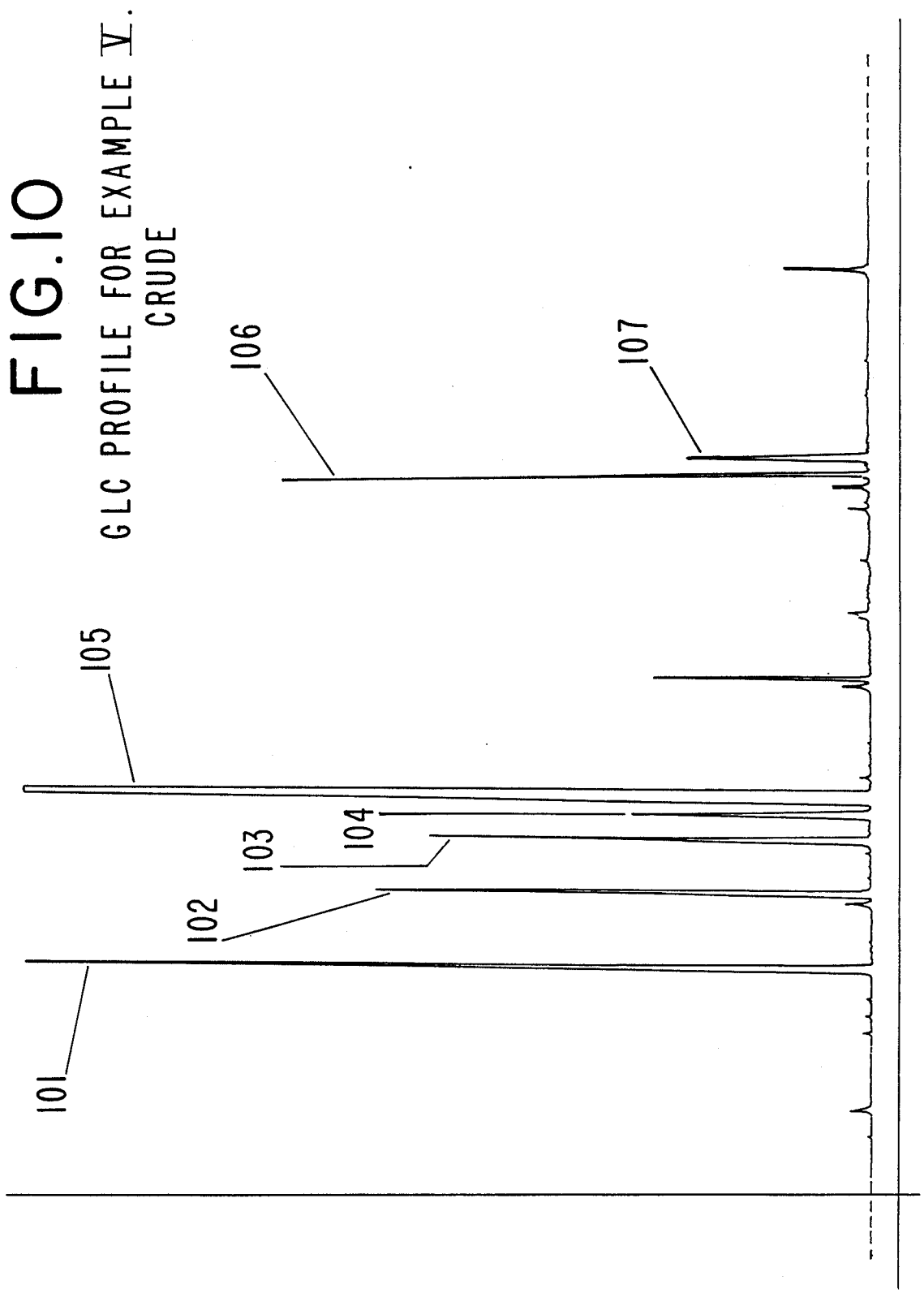

FIG. 10 is the GLC profile for the crude reaction product of Example V containing the compounds having the structures:

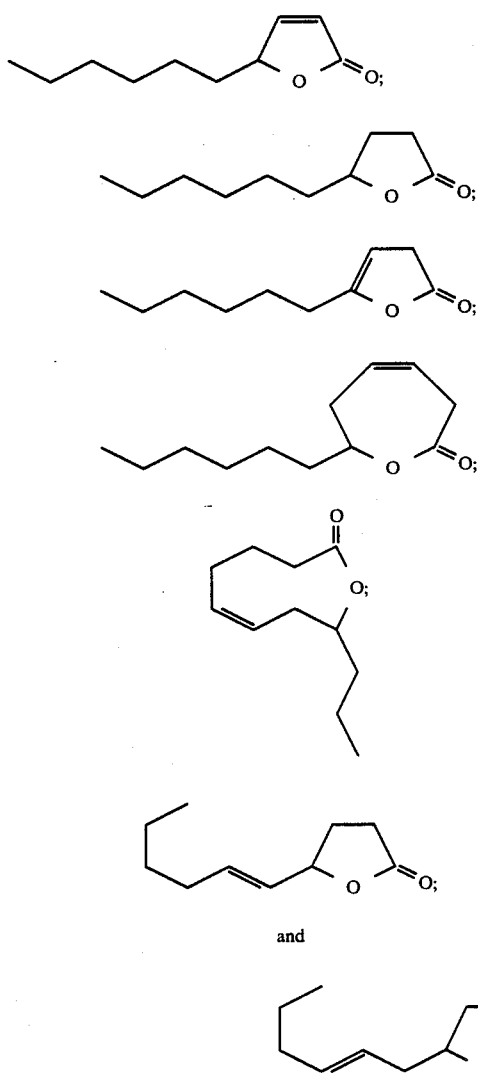

and

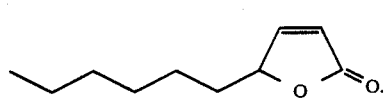

Figure 11:
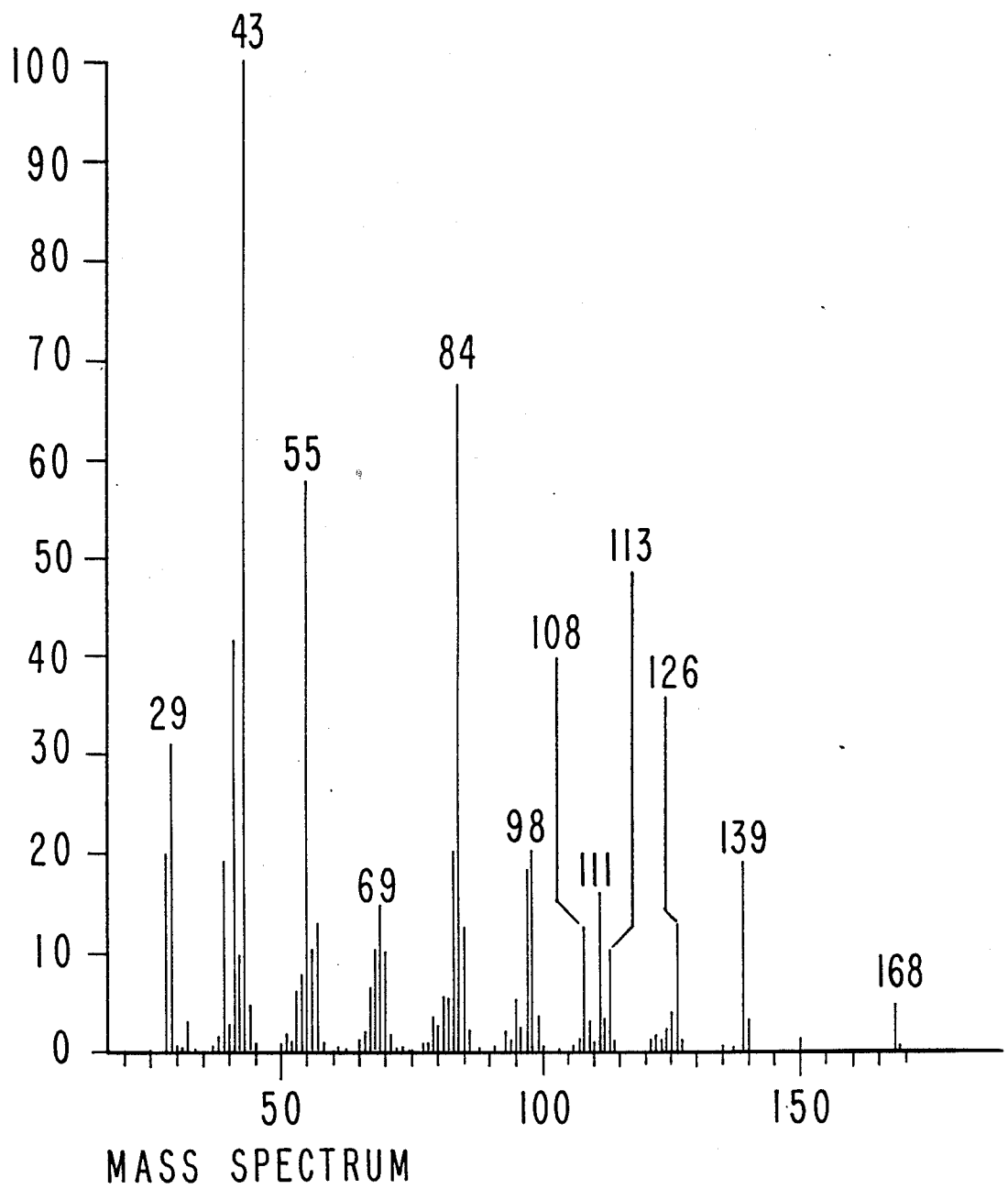

FIG. 11 is the mass spectrum for the compound having the structure:

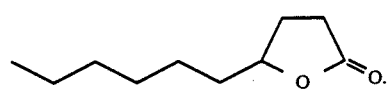

Figure 12:
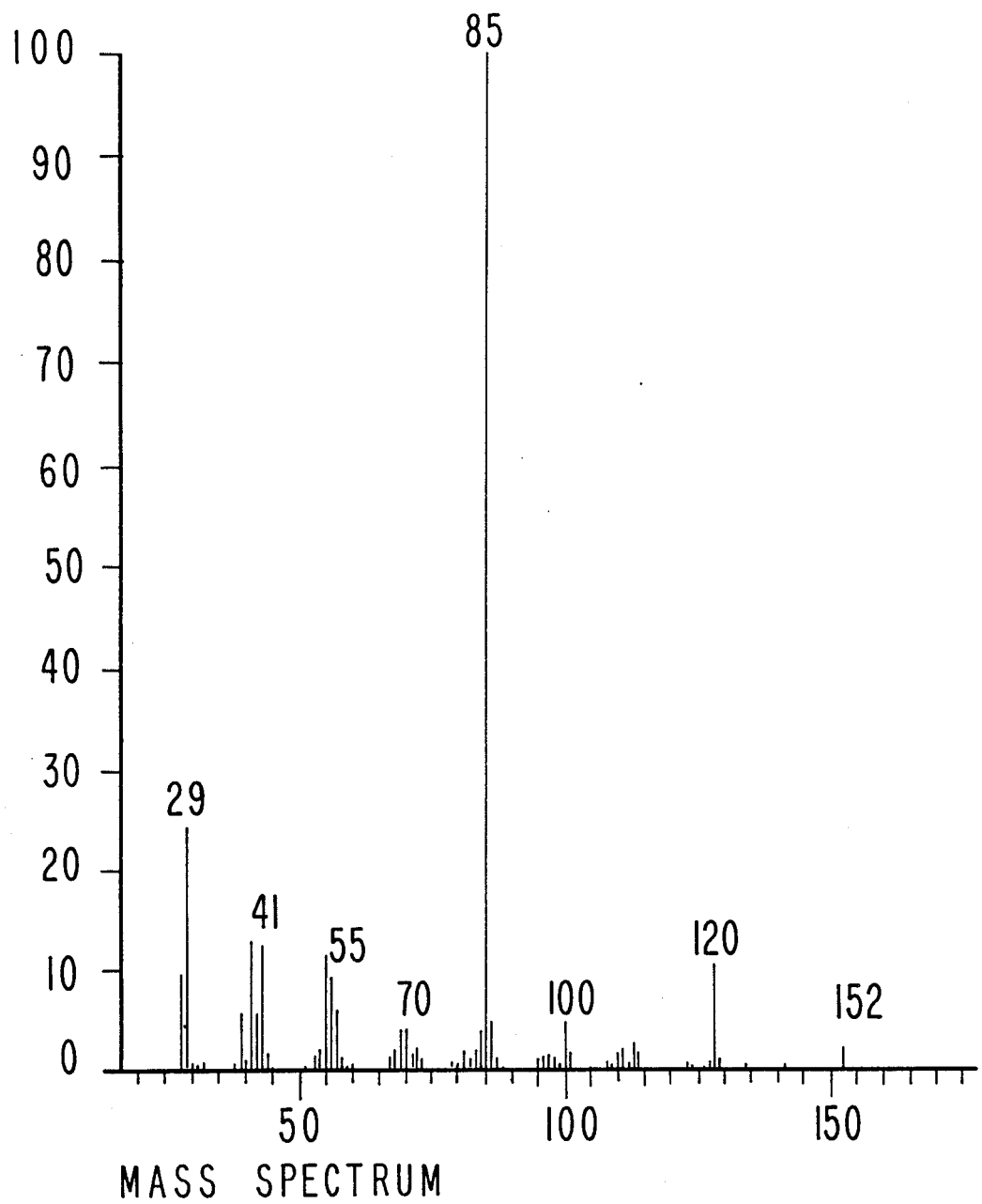
Figure 13:
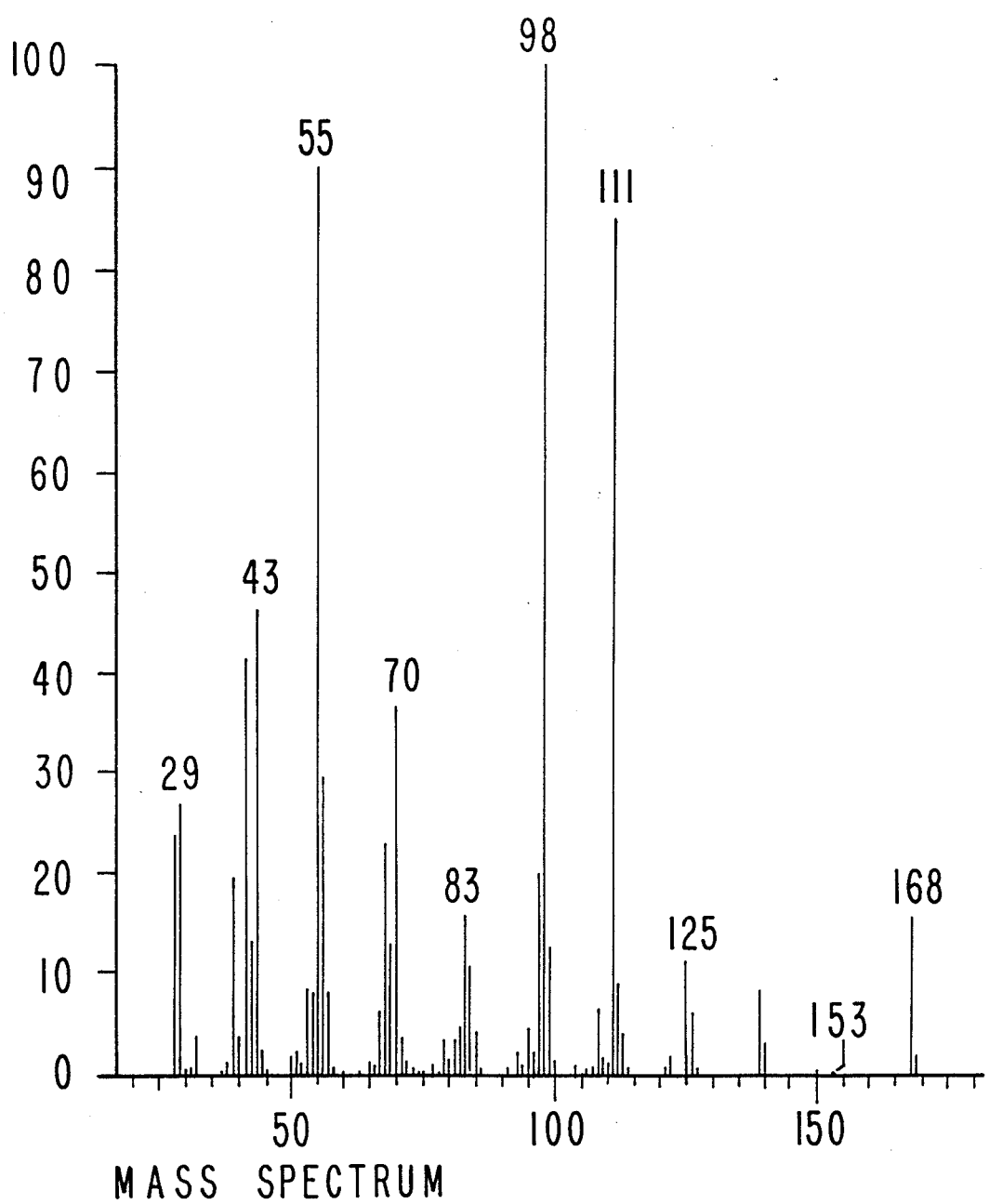

FIG. 12 is the mass spectrum for the compound having the structure:

FIG. 13 is the mass spectrum for the compound having the structure:

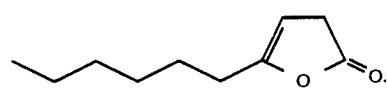

Figure 14:
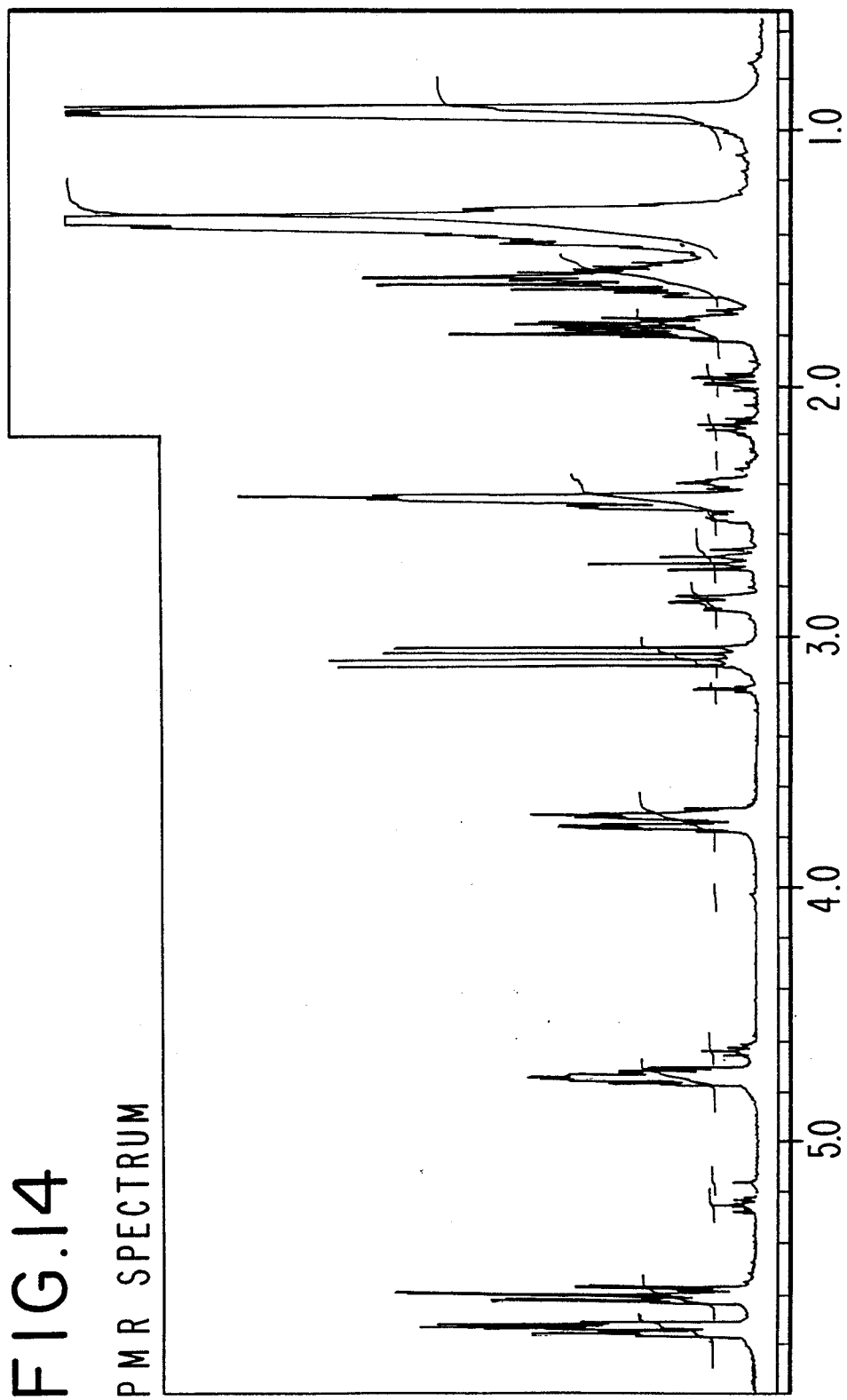

FIG. 14 is the PMR spectrum for the compound having the structure:

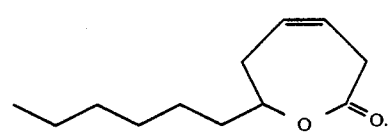

Figure 15:
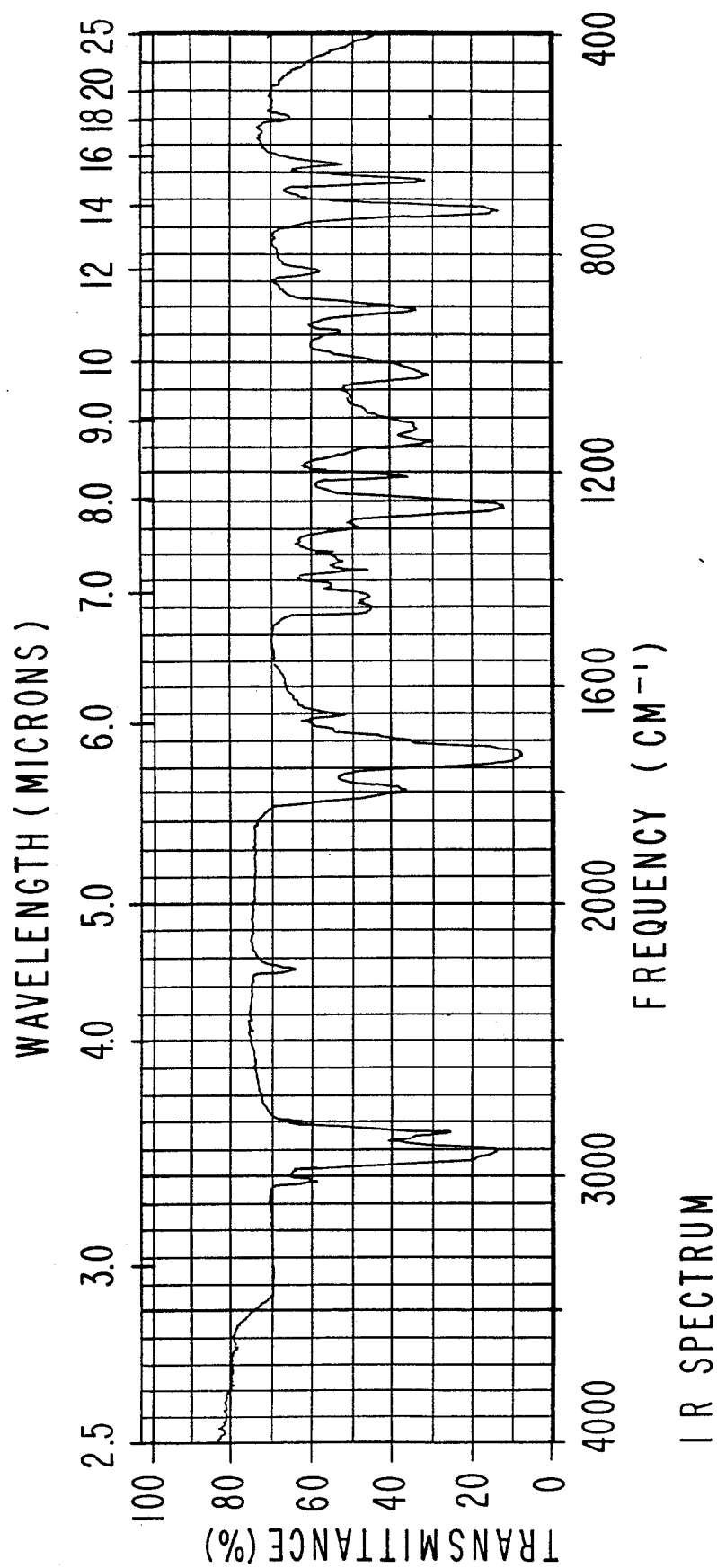

FIG. 15 is the infra red spectrum for the compound having the structure:

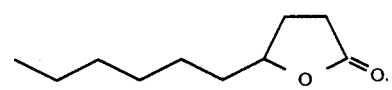

FIG. 16 is the NMR spectrum for Fraction 12 of the distillation of the reaction product of Example V.

FIG. 17 is the NMR spectrum for the compound having the structure:

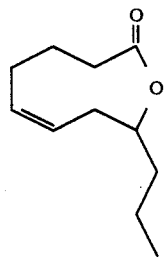

produced according to Example V.

FIG. 18 is the mass spectrum for the mixture of compounds having the structures:

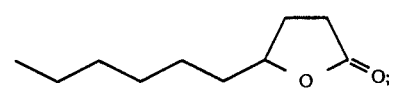

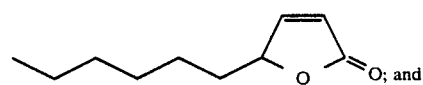

-continued

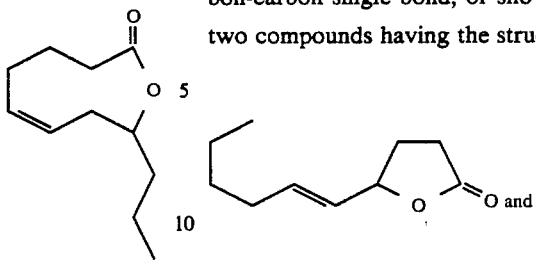

produced according to Example V.

FIG. 19 is the mass spectrum for the compound having the structure:

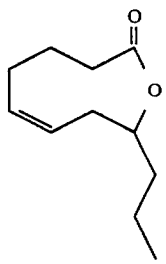

produced according to Example V.

DETAILED DESCRIPTION OF THE DRAWINGS

Figure 1:
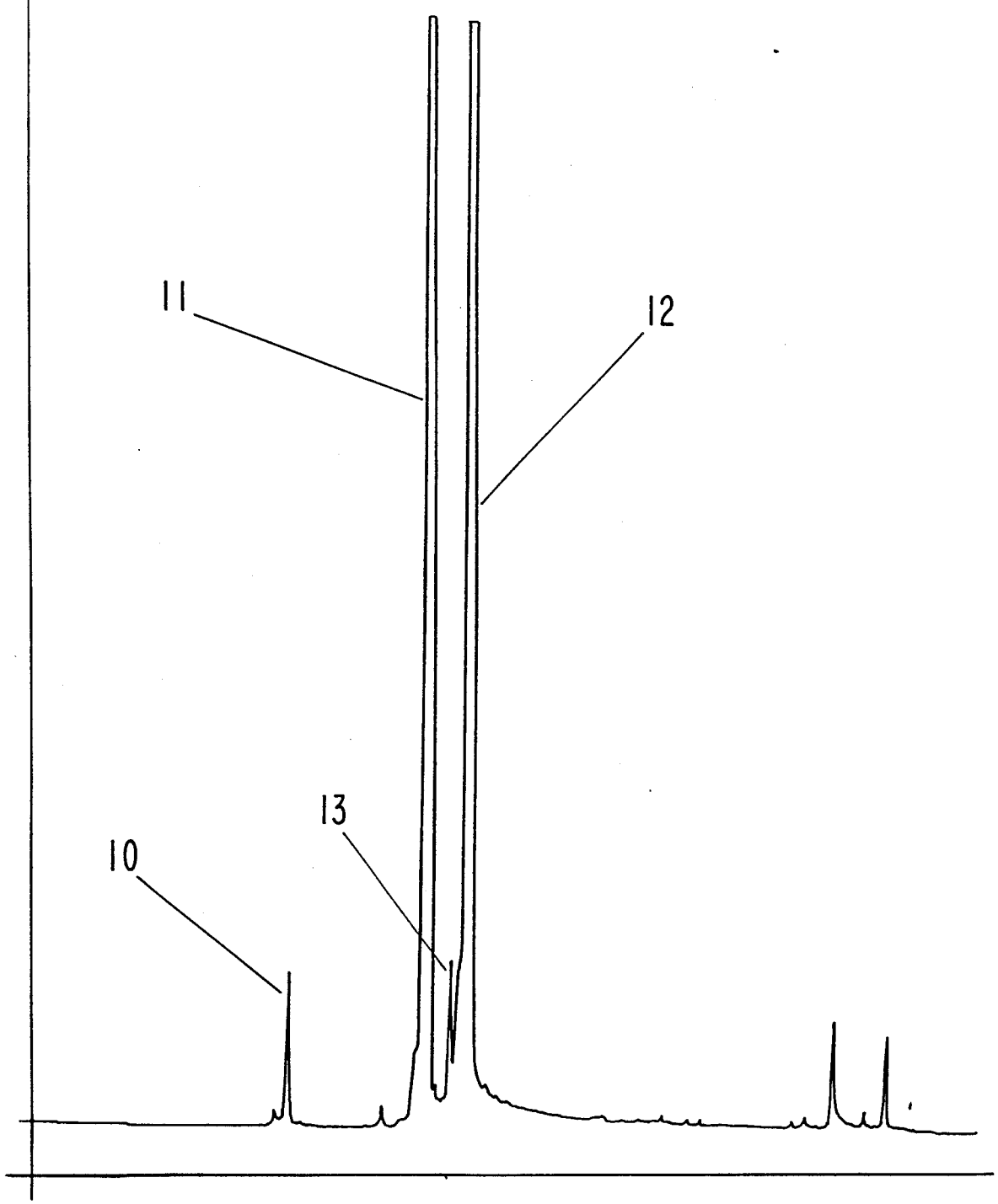
FIG. 1 is the GLC profile for the reaction product of Example I containing the compounds having the structures.

FIG. 1 is the GLC profile for the reaction product of Example I. The peak indicated by reference numeral 10 is the peak for the compound having the structure:

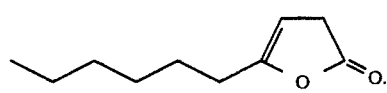

The peak indicated by reference numeral 11 is the peak for the compound having the structure:

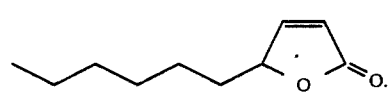

The peak indicated by reference numeral 12 is the peak for the compound having the structure:

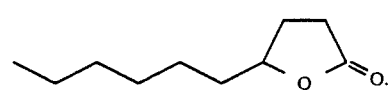

The peak indicated by reference numeral 13 is the peak for the mixture of compounds shown according to the structure:

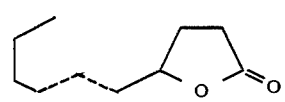

(wherein one of the dashed lines is a carbon-carbon double bond and the other of the dashed lines is a carbon-carbon single bond; or shown as a mixture of the two compounds having the structures:

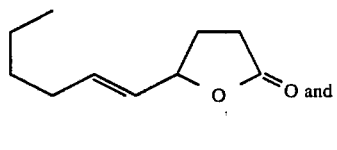

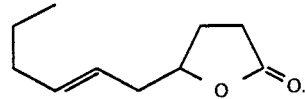

FIG. 2 is the GLC profile of the distilled reaction product of Example I. The peak indicated by reference numeral 20 is the peak for the compound having the structure:

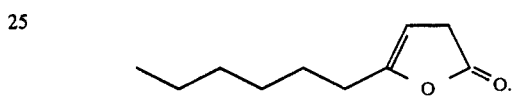

The peak indicated by reference numeral 21 is the peak for the compound having the structure:

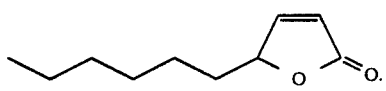

The peak indicated by reference numeral 22 is the peak for the mixture of compounds having the structures:

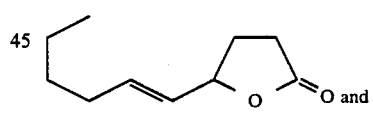

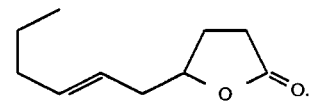

The peak indicated by reference numeral 23 is the peak for the compound having the structure:

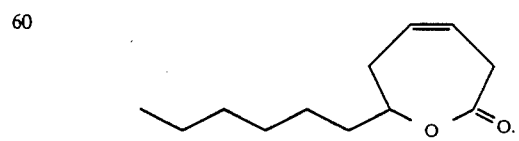

The peak indicated by reference numeral 24 is the peak for the compound having the structure:

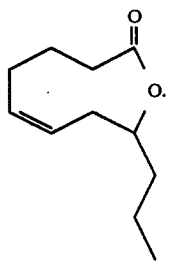

FIG. 3 is the GLC profile for the reaction product of Example II. The peak indicated by reference numeral 30 is the peak for the compound having the structure:

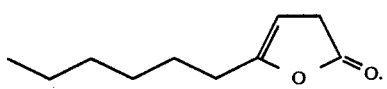

The peak indicated by reference numeral 31 is the peak for the compounds having the structures:

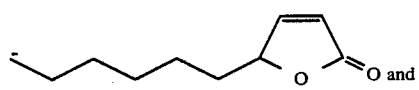

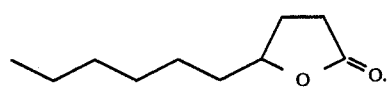

The peak indicated by reference numeral 32 is the peak for the mixture of compounds having the structures:

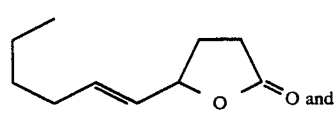

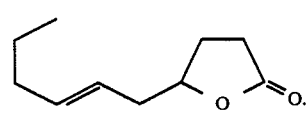

FIG. 8 is the GLC profile for Fraction 1 of the distillation of the reaction product of Example V (Conditions: 50 m×0.32 mm OV-1 fused silica column). The peak indicated by reference numeral 80 is the peak for the compound having the structure:

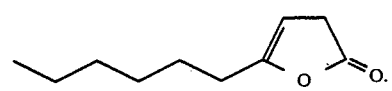

FIG. 9 is a graph showing percent reactant versus time (hours) for Example V. The graph indicated by reference numeral 90 is the graph showing percent ricinoleic acid. The peak indicated by reference numeral 91 is the peak for $C_{12}$ lactone having the structure:

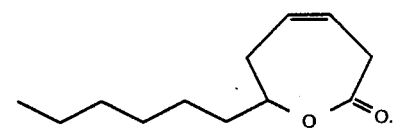

The peak indicated by reference numeral 92 is the peak for gamma decalactone having the structure:

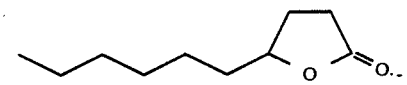

The peak indicated by reference numeral 93 is the peak for $C_{14}$ lactone having the structure:

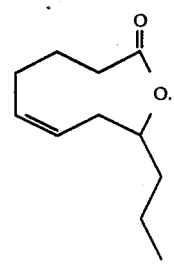

The peak indicated by reference numeral 94 is the peak for gamma decalactone via distillation having the structure:

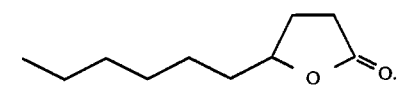

The peak indicated by reference numeral 95 is the peak for another isomer of the compound having the structure:

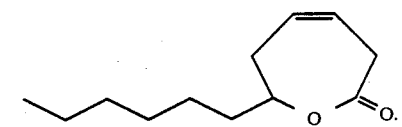

FIG. 10 is the GLC profile for the crude reaction product of Example V. The peak indicated by reference numeral 101 is the peak for the compound having the structure:

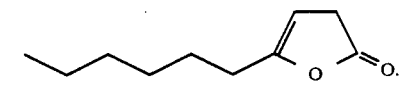

The peak indicated by reference numeral 102 and the peak indicated by reference numeral 104 are peaks for the compounds having the structures:

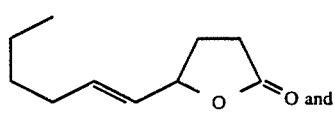

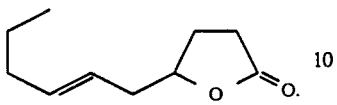

The peak indicated by reference numeral 103 is the peak for the compound having the structure:

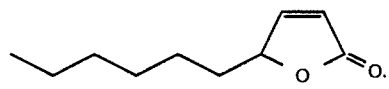

The peak indicated by reference numeral 105 is the peak for the compound having the structure:

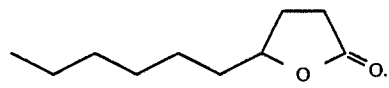

The peak indicated by reference numeral 106 is the peak for the compound having the structure:

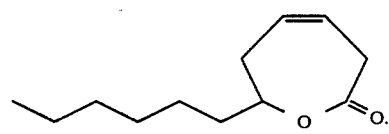

The peak indicated by reference numeral 107 is the peak for the compound having the structure:

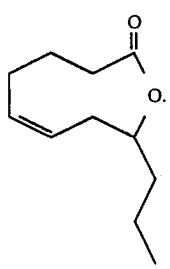

FIG. 18 is the mass spectrum for the mixture of compounds having the structures:

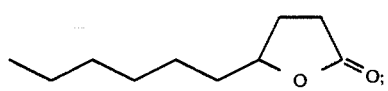

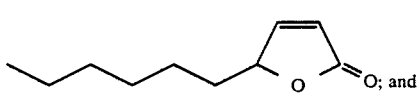

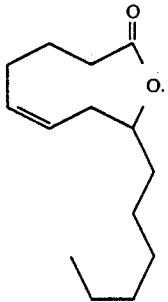

The peak indicated by reference numeral 182 is the peak for the compound having the structure:

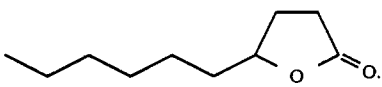

The peak indicated by reference numeral 181 is a peak for the compound having the structure:

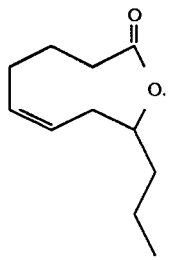

The peak indicated by reference numeral 183 is a peak for the compound having the structure:

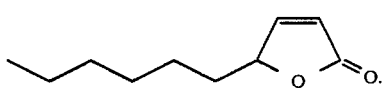

SUMMARY OF THE INVENTION

Our invention relates to a method using fermentation techniques to produce and recover certain naturally occurring lactones found to be useful for their organoleptic properties in augmenting or enhancing the aroma or taste of consumable materials such as foodstuffs, chewing gums, toothpastes, medicinal products, chewing tobaccos, smoking tobaccos, perfume compositions, colognes and perfumed articles, e.g., solid or liquid anionic, cationic, nonionic or zwitterionic detergents, perfumed polymers, fabric softener compositions, fabric softener articles, cosmetic powders, hair preparations and the like which lactones are defined according to the structures:

and taken alone or taken further together with the lactone having the structure:

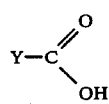

wherein R represents $C_6$ alkyl or alkenyl; and X represents alkylene or alkenylene with the provisos that R is $C_6$ alkyl when X is alkenylene and R is $C_6$ alkenyl when X is alkenylene. The lactone compositions are produced by means of fermentation of castor oil or ricinoleic acid or a castor oil hydrolysate to form a mixture of carboxylic acids having the structure:

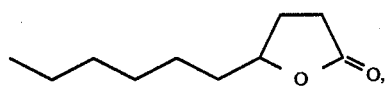

together with the gamma hydroxydecanoic acid according to the reaction:

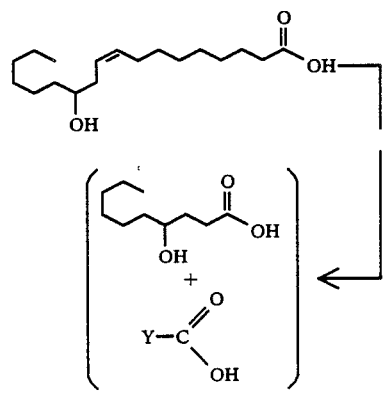

with the reaction of the castor oil going to the ricinoleic acid being shown, thusly:

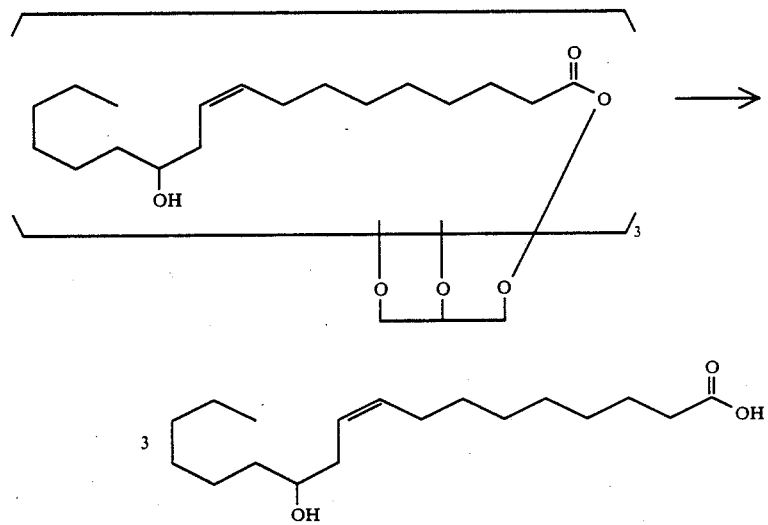

More specifically, the fermentation reaction of the ricinoleic acid going to the various carboxylic acids is shown according to the reaction:

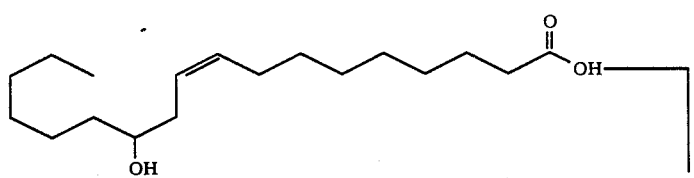

-continued

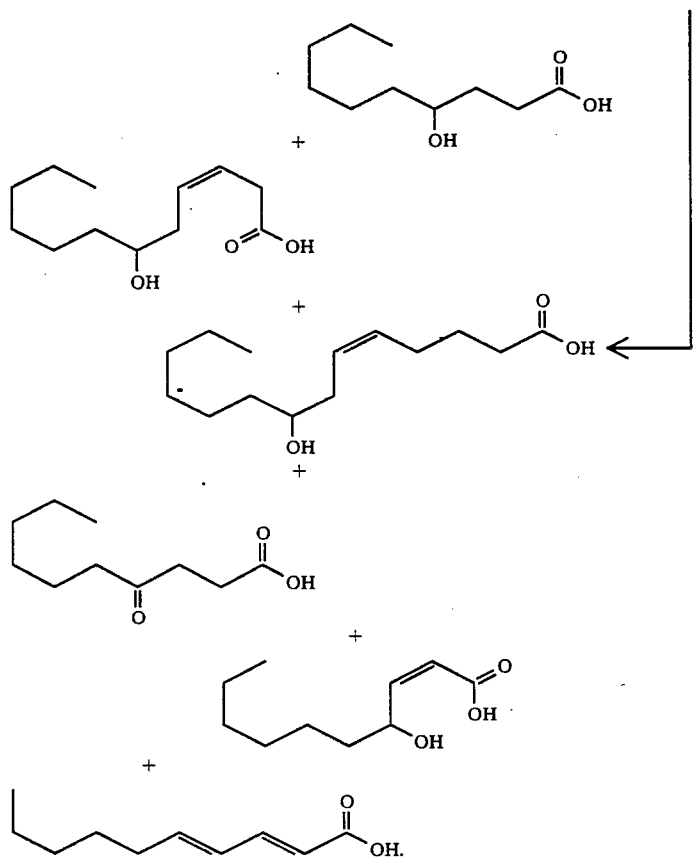

The fermentation reaction is effected as a result of the presence in the reaction mass of certain organism, to wit, one of:
Candida petrophilum, ATCC 20226;
Candida oleophila, ATCC 20177;
Candida sp., ATCC 20504; or
Candida sake, ATCC 28137.

The resulting reaction mass is then subjected to a pH reduction to a pH in the range of 0–5 and heated at a temperature in the range of about 90° up to about 120° C. whereupon lactinization of the gamma hydroxydecanoic acid takes place, thusly:

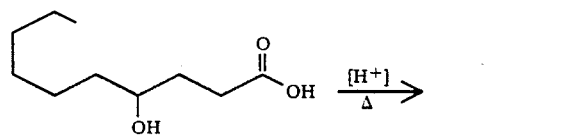

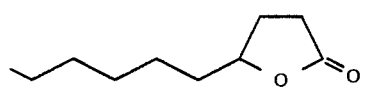

The other acids in the reaction mass do not lactinize.

The third step of the process of our invention involves distillation of the reaction mass at a temperature in the range of 120°–220° C. and at a pH of between about 1 and about 7 whereby the unsaturated acids lactinize according to the reaction:

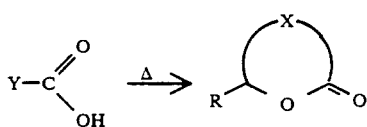

wherein the sum of the carbon atoms in the X moiety and in the R moiety is equal to the number of carbon atoms in the Y moiety minus 1 and wherein Y represents an oxo-saturated, oxo-unsaturated or di-unsaturated $C_9$, $C_{11}$ or $C_{13}$ moiety.

The resulting products, in the form of mixtures of lactones or as separate lactones or groups of lactones are useful in augmenting or enhancing the aroma or taste of consumable materials as set forth, supra.

The first step of the process of our invention involving the reactions:

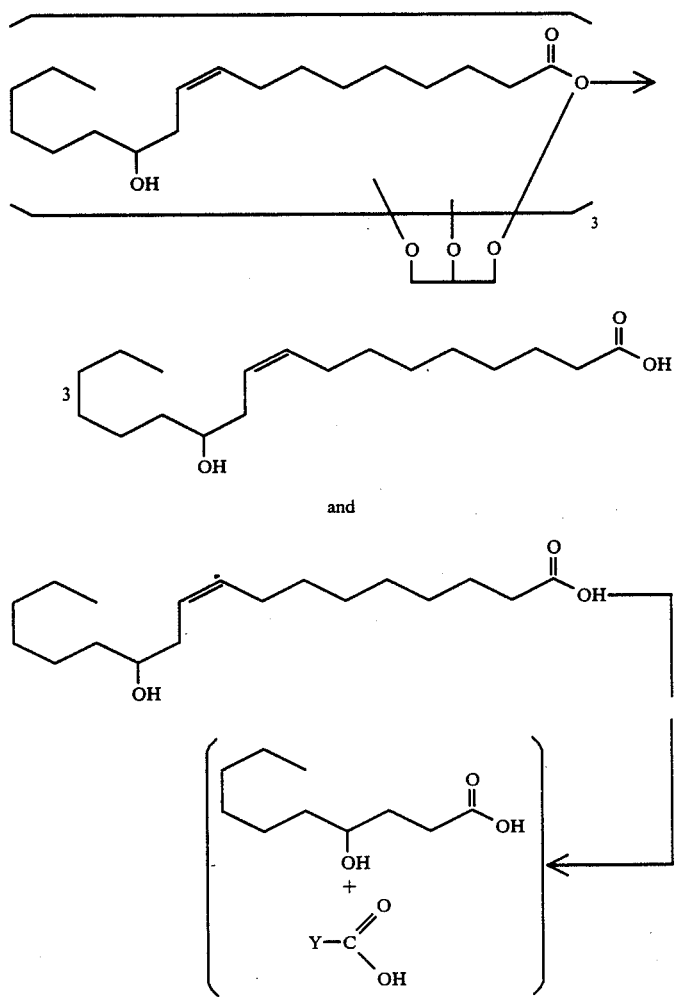

takes place at a pH in the range of 5.5 up to 7 and a temperature in the range of from about 20° up to about 35° C.

Prior to the reaction taking place an inoculum is produced whereby the microorganism, e.g., *Candida petrophilum*, ATCC 20226 is grown in olive oil for a period of about 10 up to about 30 hours. The resulting inoculum is then admixed with castor oil or a castor oil hydrolysate substrate.

The form in which the microorganisms are used is not critical. They can be used as the culture (suspension), i.e., including the cells and the corresponding nutrient solution, or in the form of cells suspended in a buffer solution. The cells or an enzyme extract thereof may be immobilized on a suitable solid support which may then be used to effect the transformations.

The culture suspension is prepared by inoculation of a suitable medium with the microorganism. A suitable medium is one which contains carbon sources, nitrogen sources, inorganic salts and growth factors. Among the suitable carbon sources are for example, glucose, galactose, L-sorbose, maltose, sucrose, cellobiose, trehalose, L-arabinoise, L-rhamnoise, ethanol, glycerol, L-erythritol, D-mannitol, lactose, melibiose, raffinose, meleritose, starch, D-xylose, D-sorbitol, alpha-methyl-D-glucoside, lactic acid, citric acid and succinic acid. Among the suitable nitrogen sources are, for example, nitrogen-containing organic substances such as peptone, meat extract, yeast extract, corn steep liquor, and casein, urea, amino acids, or nitrogen containing inorganic compounds such as nitrates, nitriles, and inorganic ammonium salts. Among the suitable inorganic salts are, for example, phosphates, magnesium, potassium, calcium, sodium. The above mentioned nutrients in the culture medium may be supplemented with, for example, one or more vitamins of the B Group and/or one or more trace minerals such as Fe, Mo, Cu, Mn, B as desired. However, the process can be performed in a vitamin-free medium, for example, when a small amount of yeast extract is added to the medium there is no need for vitamins or trace minerals.

The cultivation of the microorganism can be carried out as a stationary culture or as a submersed culture (e.g., shaking culture, fermentors) preferably under aerobic conditions. One suitably may work in the pH range of from about 3.5 to about 8.0, and preferably in the range of from about 4.0 to about 7.5. The pH may be regulated by the addition of inorganic or organic bases, such as sodium hydroxide, potassium hydroxide, calcium hydroxide, calcium carbonate, by ion-exchange resins, or by the addition of a buffer such as phosphate or phthalate. The incubation temperature is suitably maintained at between about 15° C. and about 33° C., with a range from about 20° C. to about 30° C. being preferred.

The process in accordance with the invention is conveniently carried out by adding castor oil or castor oil hydrolysate, as the substrate, to the culture medium at the onset of cultivation, as the sole carbon source. Alternatively, the substrate may be added in combination with another carbon source, such as dextrose, either during cultivation, or when cultivation is complete. The amount level, or concentration of the substrate in the medium any vary. For example, in the case of hydrolyzed castor oil, levels of from about 0.3% to about 5% may make up the medium initially or be added during the course of the fermentation, whereas substantially any level of castor oil may be used.

The reaction time may vary depending on the composition of the culture medium and the substrate concentration. In general, shaking flask cultures require from between about 2 h. and about 240 h. depending upon the microorganism and the composition of the culture medium. However, when a fermentor is used the fermentation time may be reduced to about 100 h. or less.

The fermentation may be carried out using the cells of the microorganism isolated from the culture solution, or with an enzyme extract isolated from the cells in a manner known per se. In this case, the fermentation can be conveniently carried out in aqueous solution, for example, in a buffer solution, in a physiological salt solution, in a fresh nutrient solution, or in water. The isolated cells or enzyme extract may be immobilized on a solid support and the desired transformation effected in the absence of the live microorganism. The transformation of the substrate may be effected by mutants of the microorganism. Such mutants can be obtained readily by methods well known in the art, for example, by exposing the cells to UV or X-rays, or customary mutagenic substances such as, for example, acridine orange.

The substrate is generally added directly to the medium. A surface-active agent or dispersion agent, such as Tween 80 (polyoxyethylenesorbitan monostearate), can also be added to an aqueous suspension of the substrate. Conventional antifoam agents, such as silicone oils (e.g., UCON), polyalkyleneglycol derivatives, maize oil, or soya oil can be used to control foaming.

The transformation of the substrate can be monitored using standard analytical techniques such as GLC, TLC, HPLC, IR and NMR. If a rapid disappearance of the substrate is observed, more substrate can then be added in order to maximize the transformation capacity of the microorganisms. The incubation is generally terminated when all the substrate has disappeared from the culture medium.

After the fermentation process is complete, the lactonization steps may take place. The first lactonization, involving the reaction of gamma hydroxydecanoic acid, to wit:

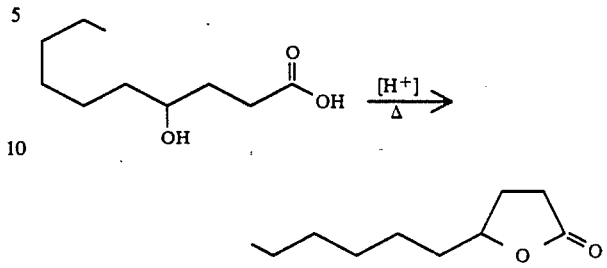

takes place at a pH in the range of 0–5 at a temperature of 90°–120° C. The pH is adjusted using acids such as 85% aqueous phosphoric acid. The reaction time may vary from about 0.25 hours up to about 2 hours. During this first lactonization step the unsaturated carboxylic acids defined according to the structure:

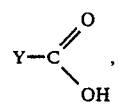

e.g., the carboxylic acids having the structures:

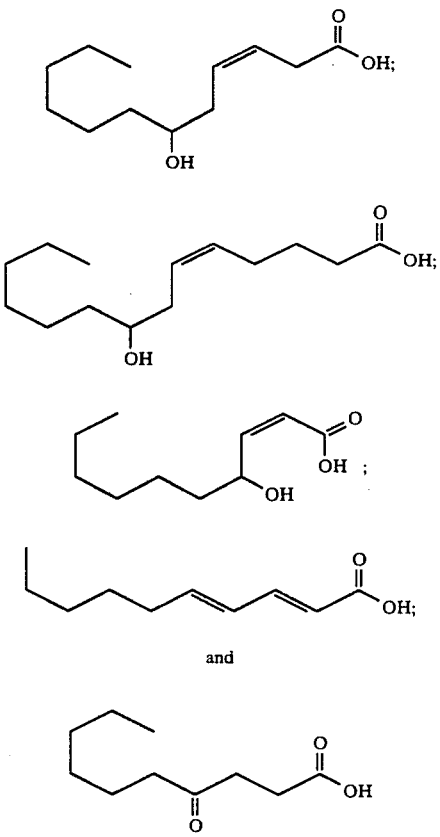

they do not lactonize.

However, when the resulting mixture containing the gamma decalactone having the structure:

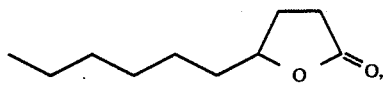

is distilled at 120°–220° C. while the pH of the reaction product is in the range of 1–7 lactones having the structures:

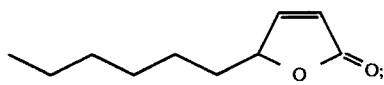

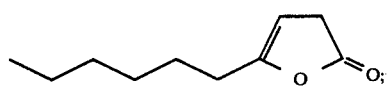

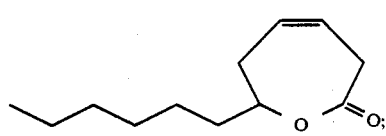

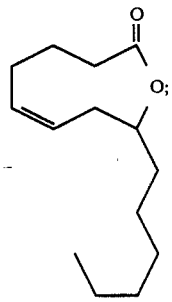

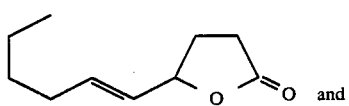   and

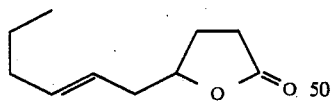

are produced according to the reactions:

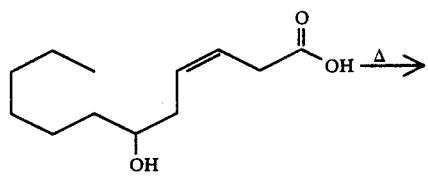

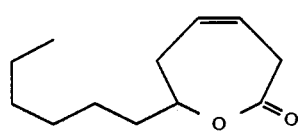

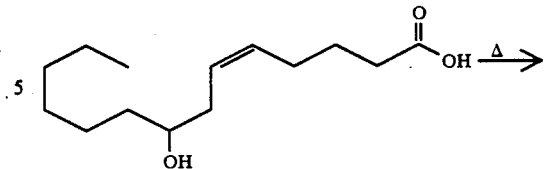

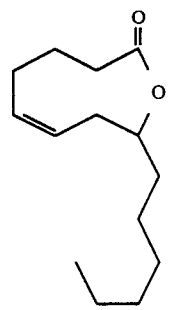

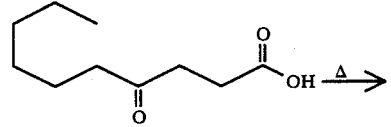

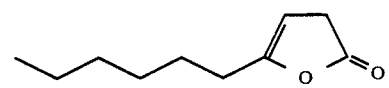

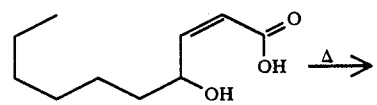

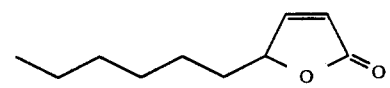

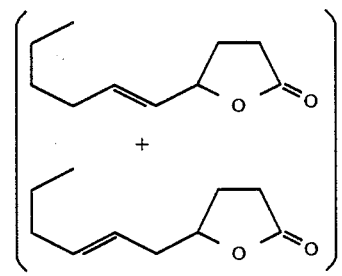

The lactone derivative(s) and one or more auxiliary perfume ingredients, including, for example, hydrocarbons, alcohols, ketones, aldehydes, nitriles, esters other than the lactone derivatives of our invention ethers, synthetic essential oils, and natural essential oils may be admixed so that the combined odors of the individual components produce a pleasant and desired fragrance, particularly and preferably in the fruity area (e.g., peach and apricot aromas). Such perfume compositions usually contain (a) the main note or the "bouquet" or foundation stone of the composition; (b) modifers which round off and accompany the main note; (c) fixatives which include odorous substances which lend a particular note to the perfume throughout all stages of evaporation and substances which retard evaporation and (d) topnotes which are usually low-boiling, fresh-smelling materials.

In perfume compositions, it is the individual compositions which contribute to their particular olfactory characteristics, however, the overall sensory effect of the perfume composition will be at least the sum total of the effects of each of the ingredients. Thus, one or more of the lactone derivative(s) of our invention can be used to alter, modify or enhance the aroma characteristics of a perfume composition, for example, by utilizing or moderating the olfactory reaction contributed by another ingredient in the composition.

The amount of lactone derivative(s) of our invention which will be effective in perfume compositions as well as in perfumed articles and colognes depends upon many factors including the other ingredients, their amounts and the effects which are desired. It has been found that perfume compositions containing as little as 0.005% of lactone derivative(s) or even less (e.g., 0.002%) can be used to impart sweet, fruity (peach and apricot) aromas to soaps, cosmetics, detergents including anionic, cationic, nonionic and zwitterionic solid or liquid detergents, perfumed polymers and other products. The amount employed can range up to 70% of the fragrance components and will depend upon the consideration of cost, nature of the end product, the effect desired on the finished product and the particular fragrance sought.

The lactone derivative(s) of our invention are useful (taken alone or taken together with other ingredients in perfume compositions) in detergents, soaps, space odorants and deodorants, perfumes, colognes, toilet waters, bath preparations, hair preparations such as lacquers, brilliantines, pomades and shampoos; cosmetic preparations such as creams, deodorants, hand lotions and sun screens; powders such as talcs, dusting powders, face powders and the like.

As little as 0.25% of the lactone derivative(s) will suffice to impart an intense, sweet, fruity (peach and apricot) aroma to floral perfume formulations. Generally no more than 5% of the lactone derivative(s) based on the ultimate end product is required to be used in the perfume compositions.

Furthermore, as little as 0.25% of the lactone derivative(s) will suffice to impart such aromas to perfumed articles per se, whether in the presence of other perfume materials or whether used by themselves. Thus, the range of use of the lactone derivative(s) of our invention in perfumed articles, e.g., perfumed polymers and solid or liquid anionic, cationic, nonionic or zwitterionic solid or liquid detergents, may vary from 0.25% up to about 5% by weight based on the total weight of the perfumed article.

In addition, the perfume composition or fragrance composition of our invention can contain a vehicle or carrier for the lactone derivative(s). The vehicle can be a liquid such as a non-toxic alcohol, e.g., ethanol, a non-toxic glycol, e.g., propylene glycol, or the like. The carrier can also be an absorbent solid such as a gum (e.g., guam arabic or xanthan gum or guar gum) or components for encapsulating the composition by means of coacervation (such as by gelatin) or by means of formation of a polymer around a liquid center (as by using a urea formaldehyde prepolymer to form a polymeric capsule around a perfume composition center).

It will be appreciated from the present disclosure that the lactone derivatives according to the present invention can be used to alter, vary, fortify, modify, enhance or otherwise improve the flavor of a wide variety of materials which are ingested, consumed or otherwise organoleptically sensed.

The terms "alter" and "modify" in their various forms will be understood herein to mean the supplying or imparting of a flavor character or note to an otherwise bland, relatively tasteless substance, or augmenting a existing flavor characteristic where the natural flavor is deficient in some regard or supplementing the existing flavor impression to modify their organoleptic character.

The term "enhance" is intended herein to mean the intensification (by use of the lactone derivative of our invention) of a flavor or aroma note or nuance in a tobacco flavor or foodstuff or perfume composition or perfumed article without changing the quality of said note or nuance.

A "flavoring composition" is taken to mean one which contributes a part of the overall flavor impression by supplementing or fortifying a natural or artifical flavor in a material or one which supplies substantially all the flavor and/or aroma character to a consumable article.

The term "foodstuff" as used herein includes both solid and liquid ingestible materials for man or animals which materials usually do, but need not, have nutritional value. Thus, foodstuffs include meats, gravies, soups, convenience foods, malt, alcoholic and other beverages, milk and dairy products, seafoods, including fish, crustaceans, mollusks and the like, candies, vegetables, cereals, soft drinks, snacks, dog and cat foof, other veterinary products, and the like. The lactone derivative(s) of our invention are also useful tobacco flavorants and flavor enhancers.

The term "tobacco" will be understood herein to mean natural products such as, for example, burley, Turkish tobacco, Maryland tobacco, flue-cured tobacco and the like including tobacco-like or tobacco-based products such as reconstituted or homogenized leaf and the like as well as tobacco substitutes intended to replace natural tobacco such as lettuce and cabbage leaves and the like. The tobaccos and tobacco products in which the lactone derivative(s) of our invention are useful include those designed or used for smoking such as in cigarettes, cigar and pipe tobacco, as well as products such as snuff, chewing tobacco and the like.

When the lactone derivative(s) of this invention are used in a flavoring composition, they can be combined with conventional flavoring materials or adjuvants.

Such co-ingredients or flavoring adjuvants are well known in the art for such and have been extensively described in the literature. Requirements of such adjuvant materials are: (1) that they be non-reactive with the lactone derivative(s) of our invention; (2) that they be organoleptically compatible with the lactone derivative(s) of our invention whereby the flavor of the ultimate consumable material to which the lactone derivative(s) are added is not detrimentally affected by the use of the adjuvant; (3) that they be ingestibly acceptable and thus non-toxic or otherwise non-deleterious. Apart from these requirements, conventional materials can be used and broadly include other flavor materials, vehicles, stabilizers, thickeners, surface active agents, conditioners, and flavor intensifiers.

Such conventional flavoring materials include saturated fatty acids, unsaturated fatty acids and amino acids; alcohols including primary and secondary alcohols, esters, carbonyl compound including ketons and aldehydes; lactones; other cyclic organic materials including benzene derivatives, allicyclic compounds, heterocyclics such as furans, pyridines, pyrazines and the like; sulfur-containing compounds including thiols, sulfides, disulfies and the like; proteins; lipids, carbohydrates; so-called flavor potentiators such as monosodium glutamate, magnesium glutamate, calcium glutamate, guanylates and inosinates; natural flavoring materials such as cocoa, vanilla and caramel; essential oils and extracts such as anise oil, clove oil and the like and artificial flavoring materials such as vanillin and the like.

Specific preferred flavor adjuvants are as follows:
anise oil;
ethyl-2-methyl butyrate;
vanillin;
cis-3-heptenol;
cis-3-hexenol;
trans-2-heptenol;
cis-3-heptenal;
butyl valerate;
2,3-diethyl pyrazine;
methyl cyclopentenolone;
benzaldehyde;
valerian oil;
3,4-dimethoxyphenol;
amyl acetate;
amyl cinnamate;
gamma butyryl lactone;
furfural;
benzaldehyde;
trimethyl pyrazine;
phenyl acetic acid;
isovaleraldehyde;
ethyl maltol;
ethyl vanillin;
ethyl valerate;
ethyl butyrate;
cocoa extract;
coffee extract;
peppermint oil;
spearmint oil;
clove oil;
anethol;
cardamom oil;
wintergreen oil;
cinnamic aldehyde;
2,3-diethyl pyrazine;
ethyl-2-methyl valerate;
gamma bexenyl lactone;
2.4-decadienal;
2,4-haptadienal; and
butylidene phthalide.

According to another aspect of our invention, an organoleptically improved smoking tobacco product and additives therefor as well as methods of making the same which overcome specific problems heretofore encountered in which specific Turkish, oriental-like aromas prior to smoking and improved Turkish, oriental aromas on smoking in the main stream and the side stream are created or enhanced or modified or agumented and may be readily controlled and maintained at the desired uniform level regardless of variations in the tobacco components of the blend. In particular, low grade Virginia-type tobaccos may be upgraded using the lactone derivative(s) of our invention.

This invention further provides improved tobacco additives and methods whereby various desirable natural aromatic Turkish tobacco flavoring characteristics with oriental notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient one or more of the lactone derivative(s) of our invention.

In addition to the lactone derivative(s) of our invention, other flavoring and aroma additives may be added to the smoking tobacco material or substitute therefor either separately or in admixture with the lactone derivative(s) of our invention as follows:

I. Synthetic Materials

Beta-ethyl—cinnamaldehyde;
Eugenol;
Dipentene;
Beta-damascenone;
Maltol;
Ethyl maltol;
Delta undecalactone;
Delta decalactone;
Benzaldehyde;
Amyl acetate;
Ethyl butyrate;
Ethyl valerate;
Ethyl acetate;
2-Hexenol-1;
2-Methyl-5-isopropyl-1,3-nonadiene-8-one;
2,6-Dimethyl-1,6-undecadiene-10-one;
2-Methyl-5-isopropyl acetophenone;
2-Hydroxy-2,5,5,8a-tetramethyl-1-(2-hydroxyethyl)-decahydronaphthalene;
Dodecahydro-3a-6,6,9a-tetramethyl naphtho(2,1-b)furan;
4-Hydroxy hexanoic acid, gamma lactone; and
Polyisoprenoid hydrocarbons defined in Example V of U.S. Pat. No. 3,589,372 issued on June 29, 1971.

Natural Oils

Celery seed oil;
Coffee extract;
Bergamot oil;
Cocoa extract;
Nutmeg oil; and
Origanum oil.

An aroma and flavoring concentrate containing one or more of the lactone derivative(s) of our invention and, if desired, one or more of the above indicated additional flavoring additives may be added to the smoking tobacco material, to the filter or to the leaf or paper wrapper. The smoking tobacco material may be shredded, cured, cased and blended tobacco material or reconstitued tobacco material or tobacco substitutes (e.g., lettuce leaves) or mixtures thereof. The proportions of flavoring additives may be varied in accordance with taste but insofar as enhancement or the imparting of oriental and/or Turkish tobacco notes, we have found that satisfactory results are obtained if the proportion by weight of the sum total of lactone derivative(s) to smoking tobacco material is between 50 ppm and 1,500 ppm (0.005%–0.15%) of the active ingredients to the smoking tobacco material. We have further found that satisfactory results are obtained if the proportion by weight of the sum total of lactone derivative(s) used to flavoring material is between 500 and 15,000 ppm (0.05%–1.5%).

Any convenient method for incorporating the lactone derivative(s) into the tobacco product may be employed. Thus, the lactone derivative(s) taken alone or along with other flavoring additives may be dissolved in a suitable solvent such as ethanol diethylether and/or volatile organic solvents and the resulting solution may either be spread onto the cured, cased, and blended tobacco material or the tobacco material may be dipped into such solution. Under certain circumstances, a solution of the lactone derivative(s) taken alone or taken further together with other flavoring additives as set forth above may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated and the thus-treated tobacco may be blended with other tobaccos before the ultimate tobacco product is formed. In such cases, the tobacco treated may have the lactone derivative(s) in excess of the amounts or concentrations above indicated so that when blended with other tobaccos, the final product will have the percentage within the indicated range.

In accordance with one specific example of our invention, an aged, cured and shredded domestic Virginia tobacco is spread with a 20% alcohol solution of the compound having the structure:

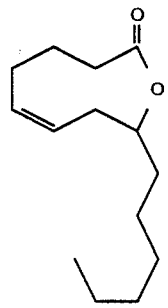

on a dry basis. Thereafter, the alcohil is removed by evaporation and the tobacco is manufactured into cigarettes by the usual techniques. The cigarette, when treated is indicated, has a desired and pleasing aroma which is detectable in the main stream and the side stream when the cigarette is smokked. This aroma is described as being sweeter, with pronounced Turkish-/oriental characteristics and with improved body and enhanced tobacco character in the main stream and side stream. In addition, interesting amber nuances are imparted.

While our invention is particularly useful in the manufacture of smoking tobacco such as cigarette tobacco, cigar tobacco and pipe tobacco, other tobacco products formed from sheeted tobacco dust or fines may also be used. Likewise the lactone derivative(s) of our invention can be incorporated with materials such as filter tip materials, seam paste, packaging materials and the like which are used along with tobacco to form a product adapted for smoking. Furthermore, the lactone derivative(s) can be added to certain tobacco substitutes of natural or synthetic origin (e.g., dried lettuce leaves) and, accordingly, by the term "tobacco" as used throughout this specification, is meant any composition intended for human consumption by smoking or otherwise when composed of tobacco plant parts or substitute materials or both.

EXAMPLE I

Preparation of Lactone Composition

Reactions:

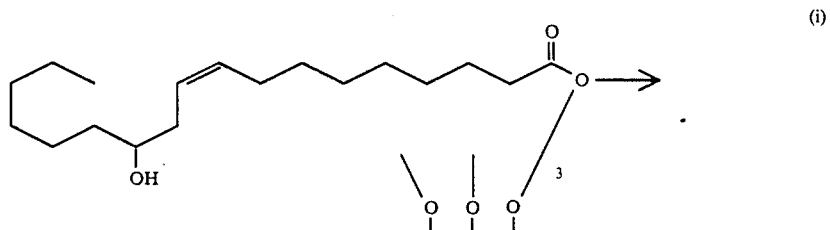

(i)

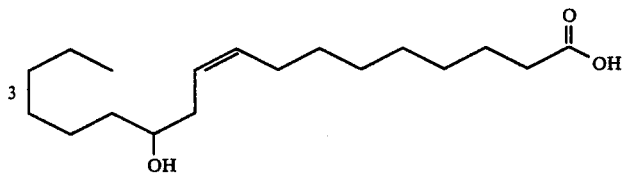
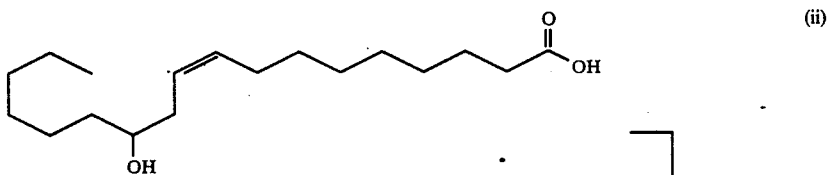
(ii)
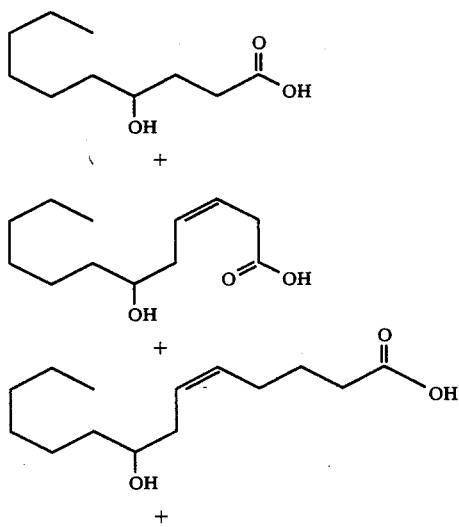
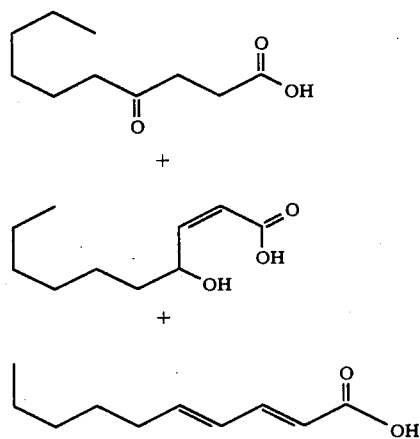
(iii)
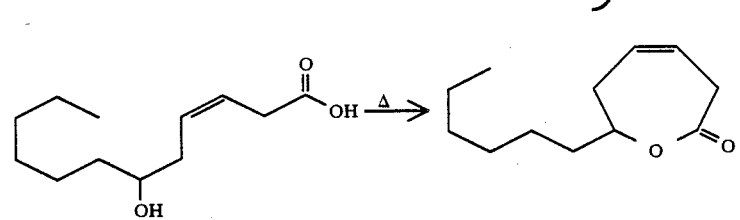

-continued

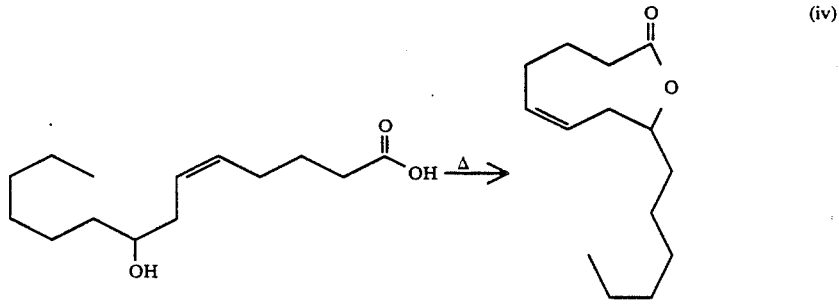 (iv)

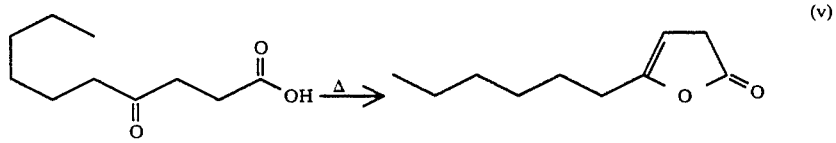 (v)

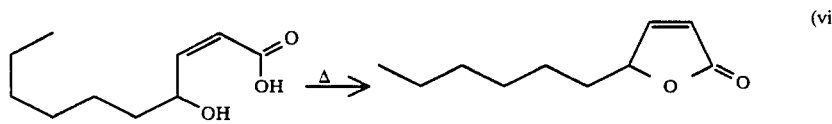 (vi)

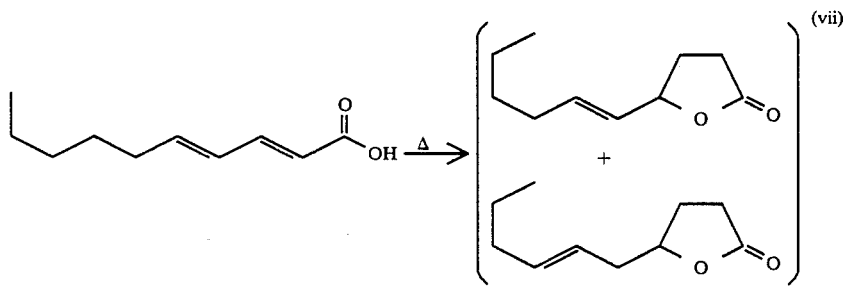 (vii)

and

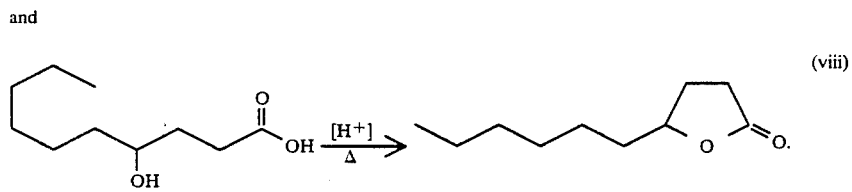 (viii)

Into a 200 liter fermentation vessel is placed a composition of matter containing 10% castor oil; 0.02% TWEEN ®80; 0.05% MgSO4.7H2O; 0.1% KH2PO4 2% beef extract and *Candida petrophilum,* ATCC 20226. The fermentation conditions are as follows:
Aeration: 0.5 liters per minute
RPM: 175
Temperature: 28° C.
Duration of fermentation: 44 hours.
Foaming was automatically controlled using silicone oil.

The *Candida petrophilum,* ATCC 20226 was added as 3 liter batch of inoculum consisting of 3% yeast extract; 0.1% KH2PO4; 0.05% MgSO47H2O; 0.02% TWEEN ®80 and 10% olive oil (aqueous emulsion).

The pH of the fermentation batch was adjusted to 2 using 85% phosphoric acid and the fermentation batch was boiled at 100° C. for a period of 30 minutes after the 44 hour fermentation period.

The fermentation batch was then cooled to 25° C. and extracted with ethyl acetate using a countercurrent extractor. Two passes was sufficient for the extraction. The ratio of broth:solvent was 2:1.

The ethyl acetate was removed in an evaportor and an oily residue of 6.1 kilograms was obtained.

The residue was subjected to fractional distillation in a 10 liter glass still using an 18" Goodloe column equipped with fraction cutter. The fractions obtained by this distillation are as follows:

| Fraction No. | Vapor Temp. (°C.) | Liquid Temp. (°C.) | Vacuum mm/Hg. Pressure | Reflux Ratio |
| --- | --- | --- | --- | --- |
| 1 | 118/145 | 183/185 | 14.5 | 2:1 |
| 2 | 150 | 185 | 14.5 | 2:1 |
| 3 | 153 | 185 | 14.5 | 2:1 |
| 4 | 154 | 186 | 14.0 | 2:1 |
| 5 | 155 | 187 | 14.0 | 2:1 |
| 6 | 155 | 187 | 14.0 | 2:1 |
| 7 | 155 | 189 | 14.0 | 2:1 |
| 8 | 155 | 189 | 14.0 | 2:1 |
| 9 | 155 | 190 | 15.0 | 2:1 |
| 10 | 155 | 191 | 16.0 | 2:1 |
| 11 | 156 | 193 | 16.0 | 2:1 |
| 12 | 156 | 195 | 16.5 | 2:1 |

| Fraction No. | Vapor Temp. (°C.) | Liquid Temp. (°C.) | Vacuum mm/Hg. Pressure | Reflux Ratio |
|---|---|---|---|---|
| 13 | 157 | 196 | 16.5 | 2:1 |
| 14 | 157 | 198 | 16.5 | 2:1 |
| 15 | 157 | 200 | 16.5 | 2:1 |
| 16 | 156 | 204 | 16.0 | 2:1 |
| 17 | 156 | 205 | 16.0 | 2:1 |
| 18 | 154 | 207 | 15.5 | 2:1 |
| 19 | 154 | 210 | 15.0 | 2:1 |
| 20 | 154 | 214 | 15.0 | 2:1 |
| 21 | 156 | 216 | 15.5 | 2:1 |
| 22 | 160 | 220 | 17.0 | 2:1 |
| 23 | 167 | 226 | 17.0 | 2:1 |
| 24 | 167 | 230 | 16.5 | 2:1 |
| 25 | 171 | 236 | 16.5 | 2:1 |
| 26 | 173 | 245 | 16.0 | 2:1 |
| 27 | 174 | 251 | 16.0 | 2:1 |

A total of 1351 grams of distillate in 29 fractions was obtained.

Fractions 1–19 were bulked and a mixed product was obtained. 898 Grams of this product was analyzed and determined to contain the following materials:

0.8% of the compound having the structure:

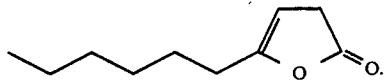

40.1% of the compound having the structure:

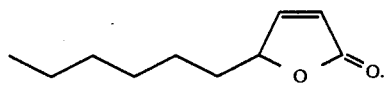

1.0% of the mixture of compounds having the structures:

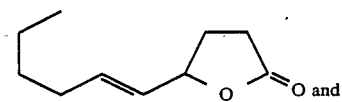

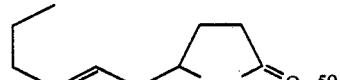

55.5% of the compound having the structure:

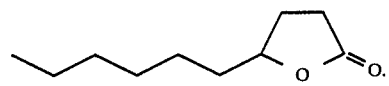

Fractions 23–27 were bulked (453 grams obtained) and determined to have the following ingredients:

5.9% of the compound having the structure:

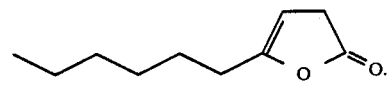

21.2% of the compound having the structure:

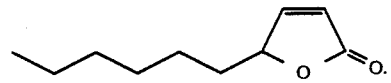

1.1% of the mixture of compounds having the structures:

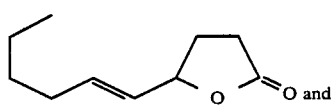

7.18% of the compound having the structure:

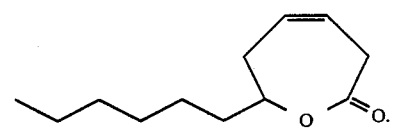

43.2% of the compound having the structure:

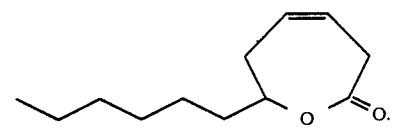

16.21% of the compound having the structure:

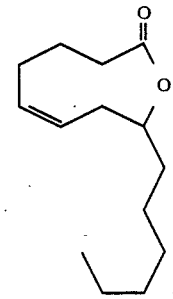

FIG. 1 is the GLC profile for bulked fractions 1–19. The peak indicated by reference numeral 10 is the peak for the compound having the structure:

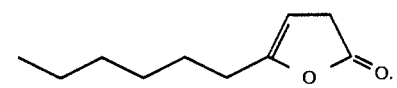

The peak indicated by reference numeral 11 is the peak for the compound having the structure:

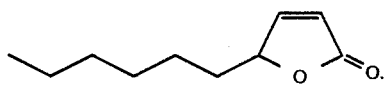

The peak indicated by reference numeral 12 is the peak for the compound having the structure:

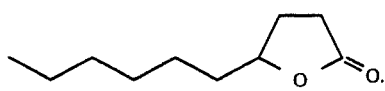

The peak indicated by reference numeral 13 is the peak for the mixture of compounds having the structures:

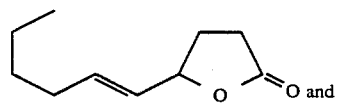

FIG. 2 is the GLC profile for bulked fractions 23–27. The peak indicated by reference numeral 20 is the peak for the compound having the structure:

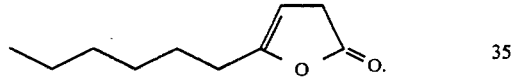

The peak indicated by reference numeral 21 is the peak for the compound having the structure:

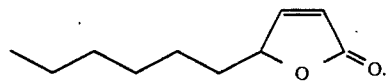

The peak indicated by reference numeral 22 is the peak for the mixture of compounds having the structures:

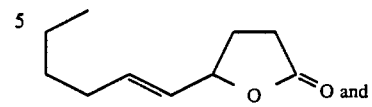

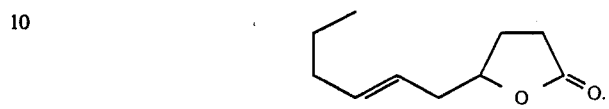

The peak indicated by reference numeral 23 is the peak for the compound having the structure:

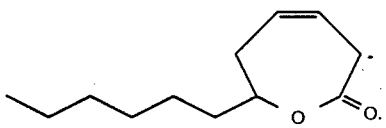

The peak indicated by reference numeral 24 is the peak for the compound having the structure:

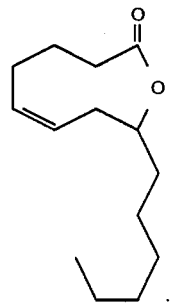

EXAMPLE II

Preparation of Lactone Composition

Reactions:

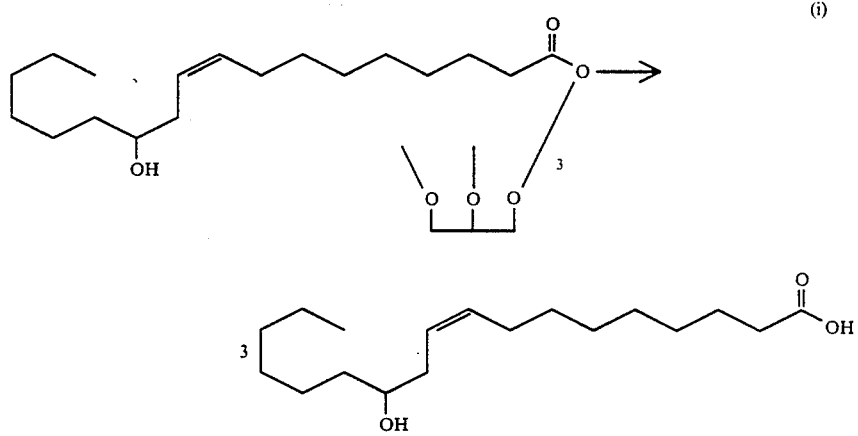

(i)

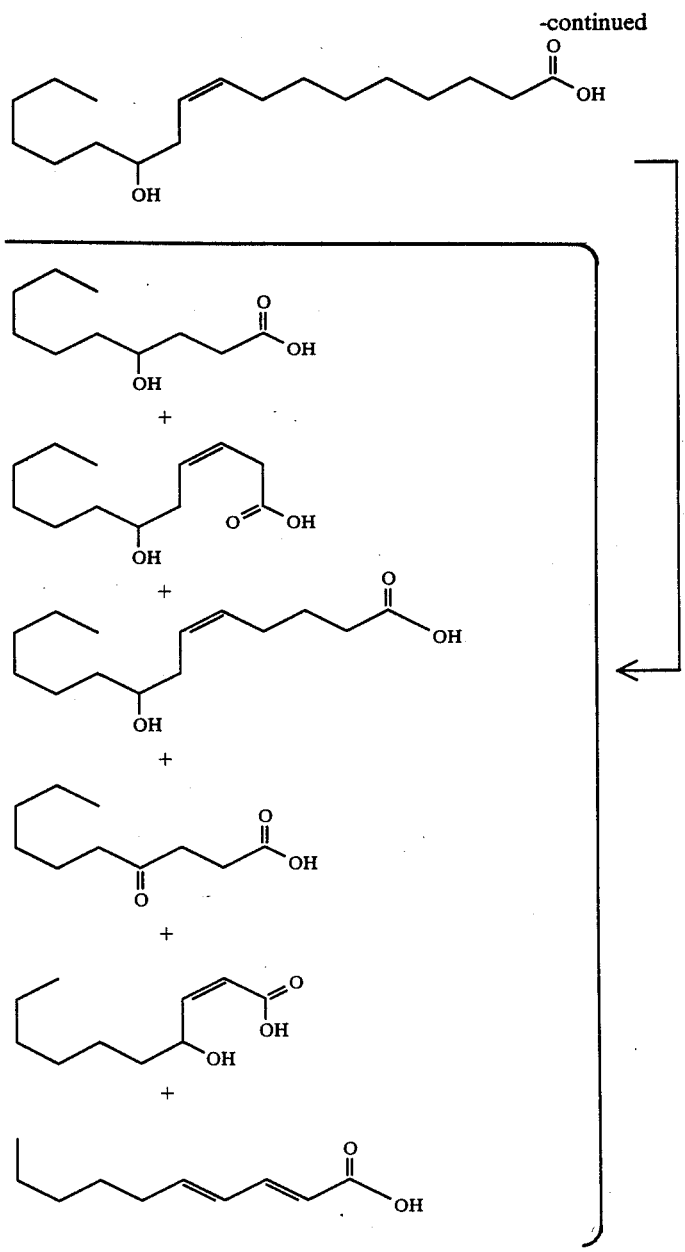
(ii)
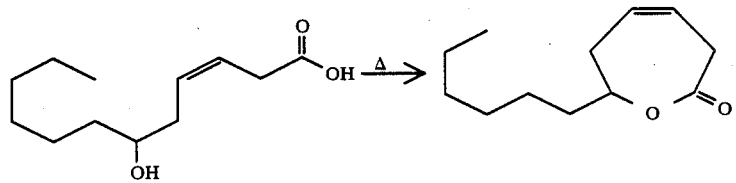
(iii)
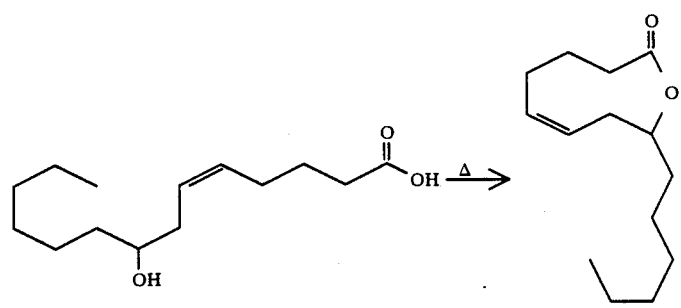
(iv)

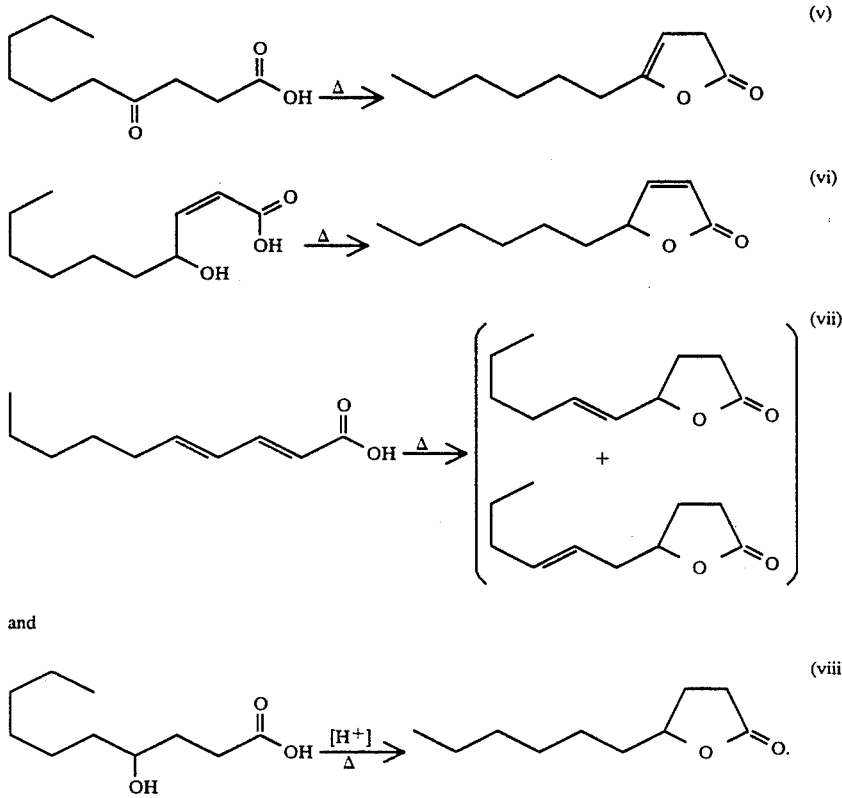

and

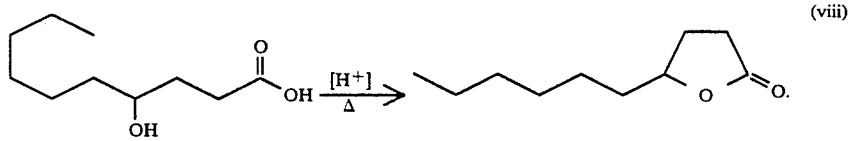

*Candida petrophilum*, ATCC 20226 inoculum (30 liters) was prepared by growing the *Candida petrophilum*, ATCC 20226 in a mixture of 3% yeast extract; 0.1% $KH_2PO_4$; 0.05% $MgSO_4 \cdot 0.7H_2O$; 0.02% TWEEN®80 and 10% olive oil at a pH of 7. The resulting inoculum was then added to the following fermentation reaction mass:

| | |
|---|---|
| 3% | AMBREX ® 5500 |
| 0.1% | $KH_2PO_4$ |
| 0.05% | $MgSO_4 \cdot 7 H_2O$ |
| 0.02% | TWEEN ® 80 |
| 10% | castor oil. |

The fermentation conditions are as follows:
Aeration: 0.5 liters per minute;
10 Psig: back pressure;
75: RPM
28° C.: temperature;
Duration: 48 hours.

Automatic foam control was effected using silicone oil as an antifoam agent.

The pH was automatically kept at 6.9 using 50% aqueous sodium hydroxide. At the end of the fermentation period (48 hours) the pH was adjusted to 2 using 85% phosphoric acid. The resulting product was boiled at 100° C. for 30 minutes and then cooled to 25° C. The resulting product was then extracted with ethyl acetate using counter current extraction. The solvent was then removed by means of evaporation.

365.5 Pounds of crude oil was obtained. The crude oil was fractionally distilled and 24 fractions were obtained having a total weight of 93.3 pounds.

The distillation fractions obtained are as follows:

| Fraction No. | Vapor Temp. (°C.) | Liquid Temp. (°C.) | Vacuum mm/Hg. Pressure | Reflux Ratio |
|---|---|---|---|---|
| 1 | 26/ | 175/ | 26/ | 1:1 |
| 2 | 140 | 196 | 24 | 1:1 |
| 3 | 145 | 198 | 22 | 1:1 |
| 4 | 145 | 198 | 22 | 1:1 |
| 5 | 148 | 198 | 22 | 1:1 |
| 6 | 150 | 198 | 22 | 1:1 |
| 7 | 160 | 200 | 22 | 1:1 |
| 8 | 164 | 200 | 22 | 1:1 |
| 9 | 164 | 200 | 23 | 1:1 |
| 10 | 165 | 205 | 23 | 1:1 |
| 11 | 165 | 205 | 23 | 1:1 |
| 12 | 165 | 205 | 24 | 1:1 |
| 13 | 168 | 210 | 24 | 1:1 |
| 14 | 170 | 210 | 24 | 1:1 |
| 15 | 170 | 212 | 24 | 1:1 |
| 16 | 172 | 215 | 23 | 1:1 |
| 17 | 172 | 220 | 23 | 1:1 |
| 18 | 176 | 225 | 23 | 1:1 |
| 19 | 176 | 228 | 23 | 1:1 |
| 20 | 175 | 230 | 23 | 1:1 |
| 21 | 177 | 240 | 22 | 1:1 |
| 22 | 178 | 240 | 22 | 1:1 |
| 23 | 178 | 255 | 17 | 1:1 |
| 24 | 178 | 265 | 6 | 1:1. |

Fraction 19 of the foregoing distillation contain the following materials:
2.9% of the compound having the structure:

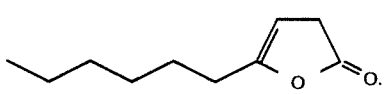

41

76.4% of the compound having the structure:

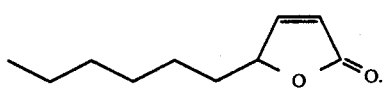

1.2% of the mixture of compounds having the structures:

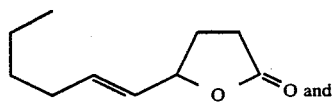

15.3% of the compound having the structure:

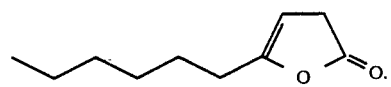

FIG. 3 is the GLC profile for fraction 19. The peak indicated by reference numeral 30 is the peak for the compound having the structure:

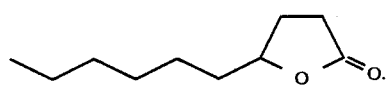

42

The peak indicated by reference numeral 31 is the peak for the mixture of compounds having the structures:

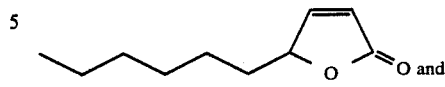

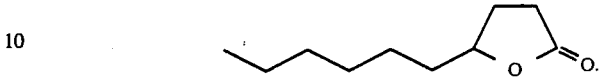

The peak indicated by reference numeral 32 is the peak for the mixtures of compounds having the structures:

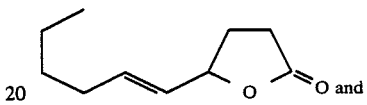

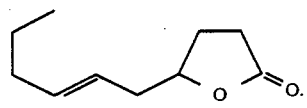

FIG. 4 is another GLC profile for fraction 19 of the foregoing distillation.

EXAMPLE III

Preparation of Mixture of Lactones

Reactions:

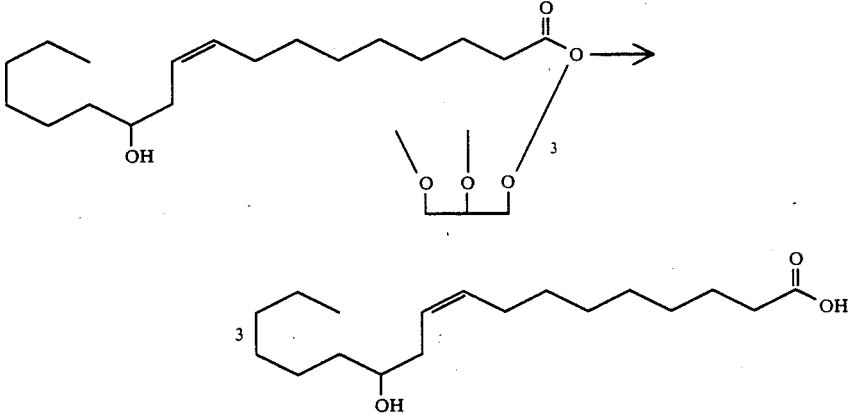

(i)

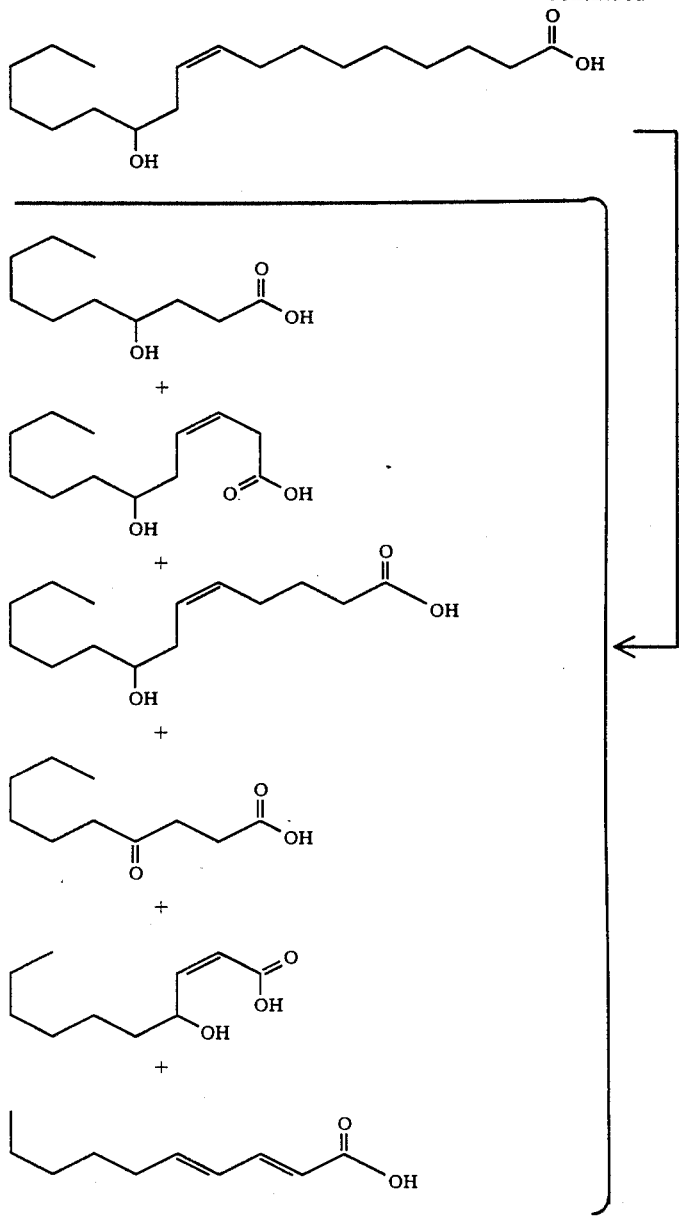

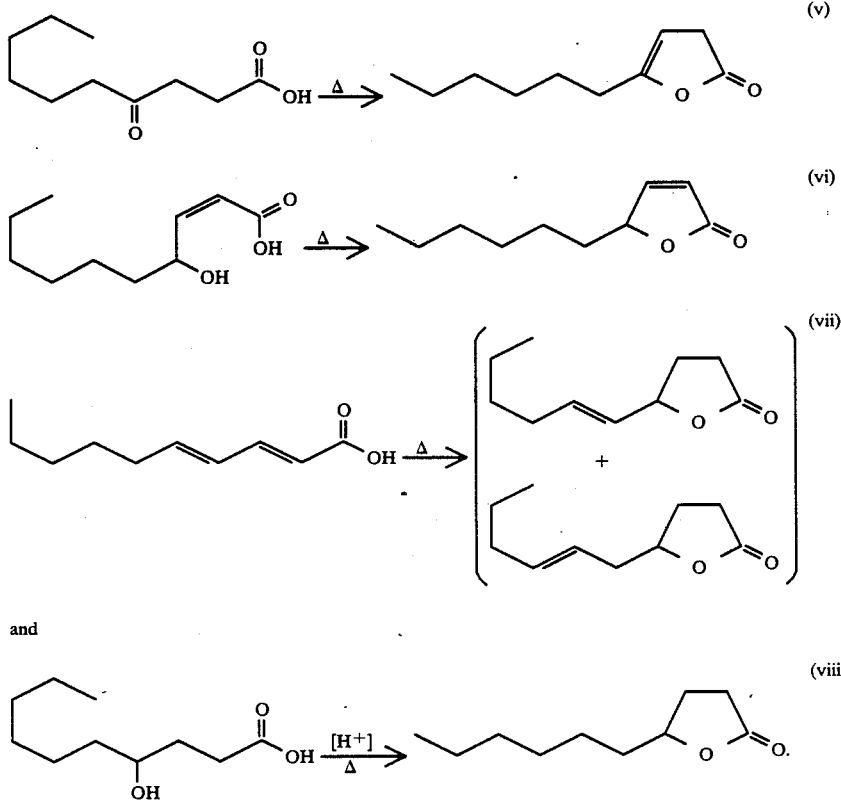

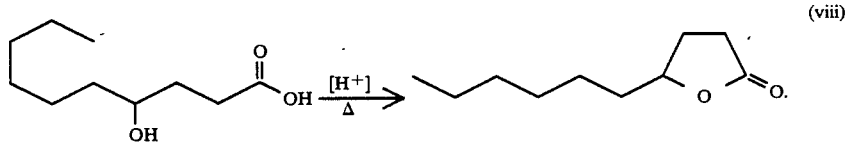

3.5 Liters of an inoculum of *Candida petrophilum*, ATCC 20226 was prepared by growing for 30 hours at 28° C. *Candida petrophilum* in the following inoculum medium:

| | |
|---|---|
| 3% | Yeast extract; |
| 0.1% | KH$_2$ PO$_4$; |
| 0.05% | MgSO$_4$.7 H$_2$O; |
| 0.02% | TWEEN ® 80; and |
| 10% | Olive oil. |

The pH of the inoculum medium was 7.0.

Into a 135 liter fermenter was placed 100 liters of the following material:

| | |
|---|---|
| 3% | Yeast extract; |
| 0.1% | KH$_2$ PO$_4$; |
| 0.05% | MgSO$_4$.7 H$_2$O; |
| 0.02% | TWEEN ® 80; and |
| 10% | Castor oil. |

The 3.5% liter mixture of inoculum was then added to the fermenter.

The fermentation conditions are as follows:

| | |
|---|---|
| pH = 6.9 + or − 0.1. | |
| Aeration: | 1 liter per minute. |
| RPM: | 220. |
| Temperature: | 28° C. + or − 0.2° C. |
| Back pressure: | 10 psig. |

The foaming was controlled using automatic foam control and silicone oil as an antifoam.

The incubation time in this particular example is 29 hours.

At the end of the 29 hour period, the pH was adjusted to 2 using 85% phosphoric acid. The fermentation batch was then boiled at 100° C. for 30 minutes and cooled to room temperature. The fermentation batch was then extracted with two batches of ethyl acetate using counter current extraction.

The solvent was evaporated on an evaportor and 5500 grams of crude oil was obtained.

The 5500 grams of crude oil was placed in a 10 liter distillation flask using a 2"×18" Goodloe column at reflux ratio 2:1 and a vacuum of 20 mm/Hg. Distillation was carried out until the vapor temperature reached 160° C. and the pot temperature reached 212° C. A total of 1505 grams of distillate was obtained having a purity of 59%. 1500 Grams of distillate was redistilled using a 3 liter flask and a 2"×18" Goodloe column with a reflux ratio of 4:1 at 1 mm/Hg. pressure and a pot temperature of 139°-164° C. and a vapor temperature of 116° C. All of the fractions were collected at a vapor temperature of 116° C. The combined fractions weighed 835 grams. FIG. 5 is the GLC profile for the resulting product.

EXAMPLE IV

Preparation of Lactones

Where reactions took place the reactions are as follows:

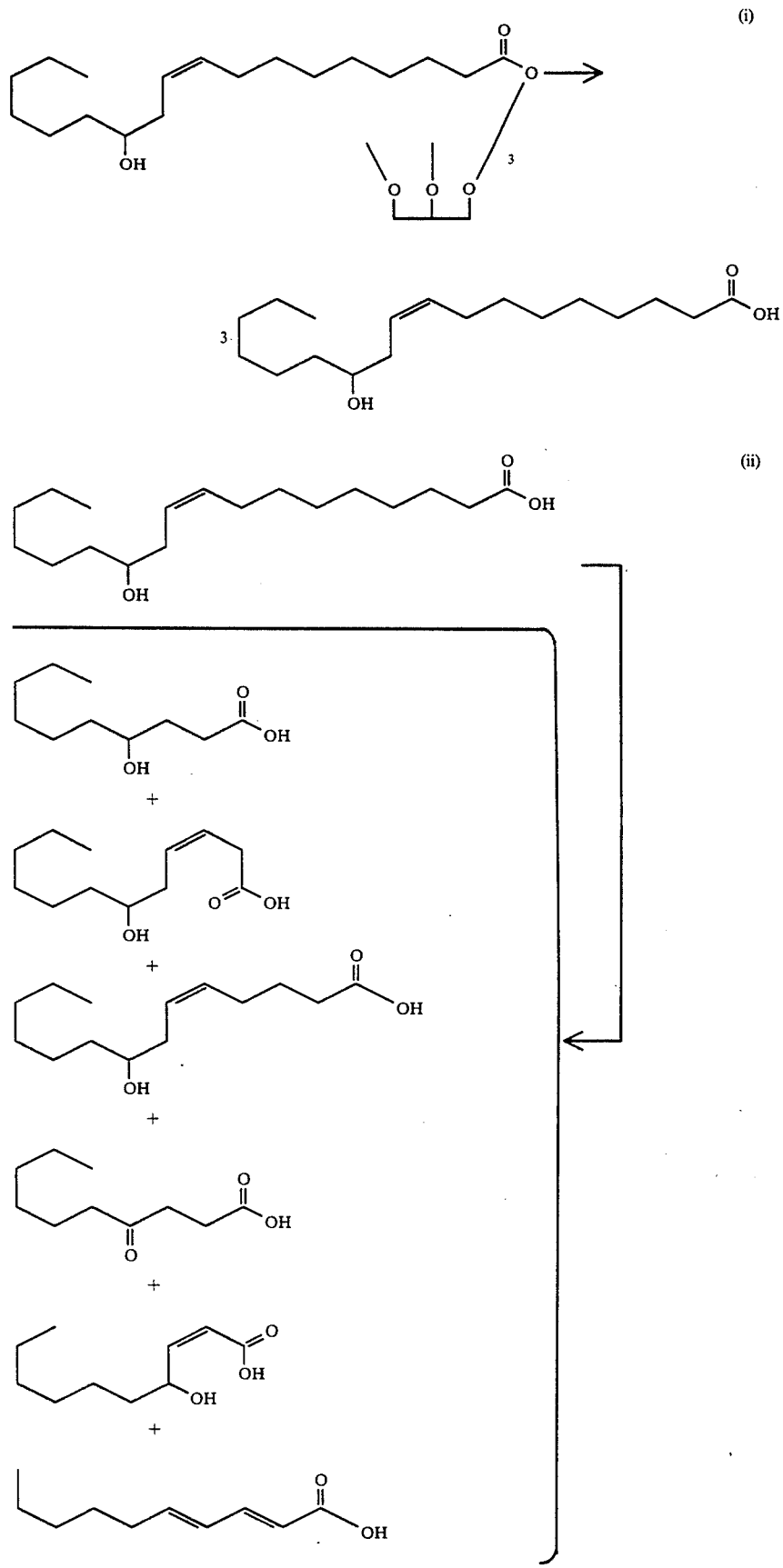

-continued
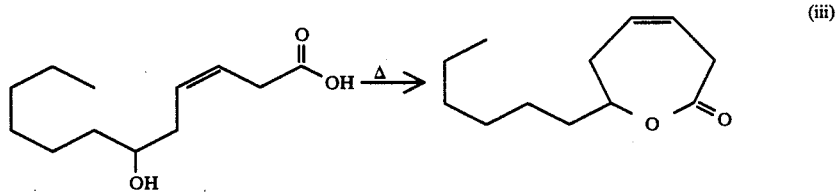
(iii)
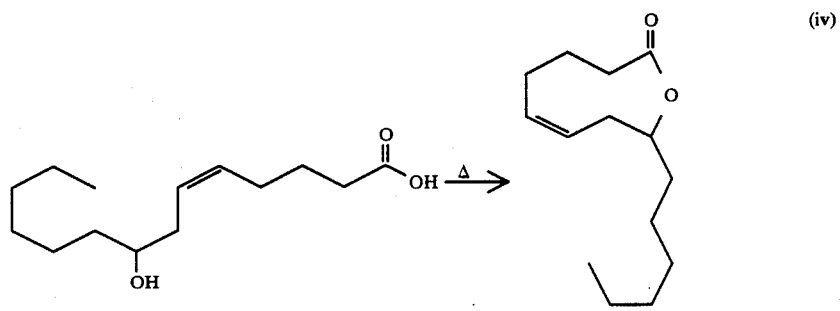
(iv)
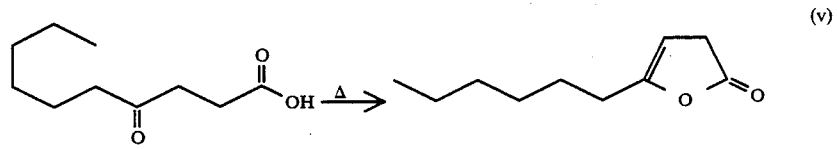
(v)
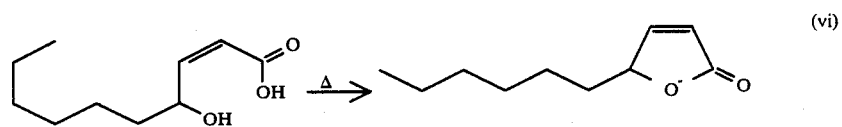
(vi)
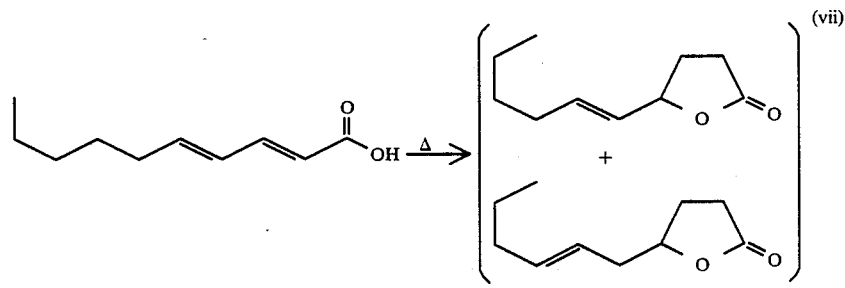
(vii)
and
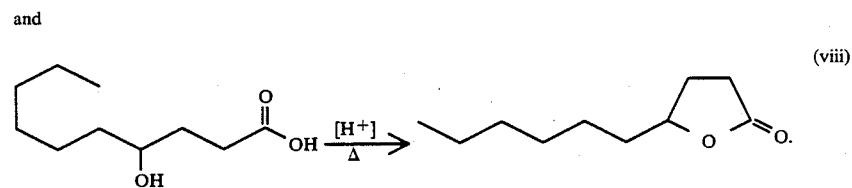
(viii)
Fermentation runs using various organisms were carried out as follows where the results as indicated below were obtained:

(i)
  Temperature: 25° C.
    RPM: 200
    Media: 2% Beef extract, 0.1% yeast extract, 0.02% TWEEN ® 80
  Substrate: Castor oil - 1 ml/100 ml broth - added 7-15-85.

| Organism | ATCC# | Growth | Results |
|---|---|---|---|
| (1) *Candida utilis* | 9226 | good | negative |
| (2) *Candida sake* | 28137 | good | some lactone |
| (3) *Metarrhizium anisopliae* | 26852 | fair | negative |
| (4) *Myriococcum sp. | 20374 | fair | negative |
| (5) *Paecilomyces farinosus* | 26853 | fair | negative |
| (6) *Penicillium caseicolum* | 24936 | fair | negative |
| (7) *Rhizopus oryzae* | 34612 | good | negative |

Samples from each flask were acidifed to pH$^2$ with phosphoric acid and heated to lactonize.

(ii)
  Temperature: 25° C.
    RPM: 200
    Media: 2% Malt extract, 0.1% Peptone, 0.02% TWEEN ® 80
  Substrate: Castor Oil - 1 ml/100 ml both - added 7-15-85.

| Organism | ATCC# | Growth | Results |
|---|---|---|---|
| (1) *Candida utilis* | 9226 | good | negative |
| (2) *Candida sake* | 28137 | good | some lactone |
| (3) *Metarrhizium anisopliae* | 26852 | fair | negative |
| (4) *Myriococcum sp. | 20374 | fair | negative |
| (5) *Paecilomyces farinosus* | 26853 | fair | negative |
| (6) *Penicillium caseicolum* | 24936 | fair | negative |
| (7) *Rhizopus oryzae* | 34612 | good | negative |

*Incubated at 42° C.

(iii)
  *Candida deformans* revived from ATCC culture #22969 using YM agar.
  7/29 -Media: 0.1% Yeast extract, 0.1% KH$_2$PO$_4$, 0.05% MgSO$_4$.7 H$_2$O,
    0.2% (NH$_4$)$_2$ SO$_4$, pH 6.5
    0.05% TWEEN ® 80
  Incubated: 25° C., 200 RPM
  Substrate: 1 ml castor oil/flask,
    Growth: good
    No lactone production observed.
  Substrate: 1 ml P10 acid/flask
    Growth: good
  Very weak lactone odor after sample was acidified and heated.

(iv)
  Candida sp (ATCC #20504) inoculated into 2 flasks
  Media: 2% Malt extract, 0.1% Peptone,
    0.02% TWEEN ® 80
  Incubated: 25° C., 200 RPM
  Substrate: 1 ml P10 acid/flask.
  7/29  One flask acidifed with phosphoric acid to "pH 2
    Refluxed 30 minutes, extracted, and distilled
    0.055 Grams product obtained.

(v)
  Incubated: 25° C., 200 RPM
  Substrate: P10 Acid, 1 ml/flask
  Media: 2% Malt extract, 0.1% Peptone, 0.02% TWEEN ® 80.

| Organism | Growth | Results |
|---|---|---|
| *C. petrophilum* 20226 | good | good |
| *C. periphelosum* 20314 | good | negative |
| *C. periphelosum* 20317 | good | negative |
| *C. oleophila* 20177 | good | good |
| *C. kefyr* 42265 | good | negative |

Media: 2% Beef extract, 0.1% yeast extract, 0.02% TWEEN ® 80.

| Organism | Growth | Results |
|---|---|---|
| 20226 | good | some lactone - odor not as strong |
| 20314 | good | negative |
| 20317 | good | negative |
| 20177 | good | best lactone - strongest odor |
| 42265 | good | negative. |

(vi)
  Incubated: 25° C., 200 RPM
  Substrate: 1 ml P10 acid/100 ml broth
    Media: (1) 2% Malt extract, 0.1% Peptone, 0.02% TWEEN ® 80
      (2) 2% Beef extract, 0.1% yeast extract, 0.02% TWEEN ® 80
  2 Flasks of each medium inoculated for each organism.
        (1) Malt (2) Beef -continued

| Organism | Growth | Extract | Extract |
|---|---|---|---|
| *Candida petrophilum* ATCC 20226 | good | 0.031 g | 0.057 g |
| *Candida oleophila* ATCC 20177 | good | 0.021 g | 0.038 g |
| Candida sp. ATCC 20504 | good | 0.021 g | 0.045 g |
| *Candida sake* ATCC 28137 | good | 0.021 g | 0.027 g |

To 1 set of flasks, 1.0 ml additional castor oil hydrolysate added after 40 hrs. (8/9). For each organism, 0.5 ml additional castor oil hydrolysate was added to one flask of each media after 18 hours incubation. Incubation was continued at 25° C., 200 RPM.

Results

| Organism | Malt Extract | Beef Extract |
|---|---|---|
| *C. petrophilum* 20226 | 0.053 g | 0.028 g |
| *C. oleophila* 20177 | 0.040 g | 0.023 g |
| Candida sp. 20504 | 0.058 g | 0.039 g |
| *C. sake* 28137 | 0.029 g | 0.055 g |

8/9 Acidified after 48 hours. incubation.

(vii)  Media: 2% Malt extract, 0.1% Peptone, 0.02% TWEEN ® 80
Incubation: 25° C., 150 RPM
Substrate: Castor oil hydrolysate.

| Organism | Amt. Substrate | Growth | Results |
|---|---|---|---|
| *Candida petrophilum* ATCC 20226 | 0.1 ml | good | weak |
| *Candida petrophilum* ATCC 20226 | 0.2 ml | good | weak |
| *Candida petrophilum* ATCC 20226 | 0.3 ml | good | weak |
| *Candida petrophilum* ATCC 20226 | 0.5 ml | good | strong extracted 48 hrs. |
| Candida sp. ATCC 20504 | 0.1 ml | good | strong extracted 48 hrs. |
| Candida sp. ATCC 20504 | 0.2 ml | good | strong extracted 48 hrs. |
| Candida sp. ATCC 20504 | 0.3 ml | good | weak |
| Candida sp. ATCC 20504 | 0.5 ml | good | weak |
| *Candida sake* ATCC 28137 | 0.1 ml | good | weak |
| *Candida sake* ATCC 28137 | 0.2 ml | good | weak |
| *Candida sake* ATCC 28137 | 0.3 ml | good | weak |
| *Candida sake* ATCC 28137 | 0.5 ml | good | weak |

(viii)  Media: 2% Beef Extract
0.02% TWEEN ® 80
2% Castor oil
Incubation: 25° C., 200 RPM.

|  | Growth |  |
|---|---|---|
| Candida sp. ATCC 20504 | good | pH started at 8.5 (24 hrs.) 48 hrs. pH 7 and then remain at 7. |
| *C. petrophilum* 20226 | good | pH adjusted to 6.5 with NaOH during course of experiment. |
| *C. oleophila* 20177 | good | pH (24 hrs.) = 8.5 pH (30 hrs.) = 7, remained at 7. |
| *C. deformans* 22969 | good | pH remained at 7 throughout experiment. |

Results

| 20504 | 9/30 faint lactone odor. |
| 20226 | 9/29 acidified to pH 1 w/$H_2SO_4$. |
| 20177 | 9/30 negative. |
| 22969 | 9/30 faint lactone odor. |
| 20226 | Extracted w/Ethyl Acetate 9/30 after distillation 0.281 g/100 ml GC indicates no lactone present. |

(ix)  10 L. fermenter
Media: 2% Beef Extract pH .7
0.02% TWEEN ® 80
0.05% Antifoam
3% Castor Oil.
Inoculated with: 3% *Candida petrophilum* ATCC #20226
24 hr. Shake flask culture, 2% Beef extract, 0.02% TWEEN ® 80, 1% Castor Oil 10/8/85 - 9 A.M.
Fermentation Conditions: 27° C., 420 RPM
pH continuously adjusted to 6.5 w/NaOH
antifoam added as needed.
10/9/85 - 24 Hr. 100 ml Sample - growth good.

Procedure for all samples:
1. Acidifed to pH 2 with .7 $H_2SO_4$.
2. Refluxed 30 minutes.
3. Extract 3X with Ethyl Acetate (100 ml each time).
4. Wash with saturated NaCl (50 ml).
5. Wash with saturated $NaHCO_3$ 3X (20 ml each time).
6. Wash with saturated NaCl 3X (50 ml each time).
7. Dry over anhydrous sodium sulfate (granular).
8. Evaporate solvent.
9. Distill 235° C., for 2 hrs., at 5 mm/Hg.
10-9-85 - 32 Hrs. - 100 ml sample - growth - good.
10-10-85 - 48 Hrs. - 100 ml Sample - growth - good.
56 Hrs. - 100 ml Sample - growth - good.

-continued 10-11-85 - 72.0 Hrs. - 100 ml Sample - growth - good.
78.5 Hrs. - 100 ml Sample - growth - good.

Results

| Time (hrs) | % Dissolved Oxygen | Crude Wgt (g) | Sample Wgt (g) | % Purity | Yield (g) |
|---|---|---|---|---|---|
| 24 | 28 | 3.0 | 0.35 | 88.7 | 0.31 |
| 32 | 36 | 2.2 | 0.47 | 8.20 | 0.39 |
| 48 | 62 | 2.4 | 0.53 | 82.1 | 0.44 |
| 56 | 69 | 2.0 | 0.50 | 95.0 | 0.48 |
| 72 | 76 | 2.4 | 0.59 | 47.2 | |
| | | | 0.34 | 17.5 | 0.34 |
| 78.5 | 80 | 1.5 | 0.25 | 49.0 | 0.12 |

(x)
Media: 0.1% Yeast extract
0.1% Beef extract
0.2% $NH_4NO_3$
0.02% TWEEN ® 80
0.05% Antifoam
3% Castor Oil.
Incoluted: 3% *Candia petrophilum*, ATCC 20226
24 Hr. Shake flask culture.
Fermentation Conditions: 27° C., 420 RPM
pH continuously adjusted to 6.5
W/50% NaOH
antifoam added as needed
aeration rate 40.
100 ml Samples taken at following times:

| | | Growth |
|---|---|---|
| 11-6 | 24 hrs. | good |
| | 32 hrs. | good |
| 11-7 | 48 hrs. | good |
| | 56 hrs. | good |
| 11-8 | 72 hrs. | good |
| | 80 hrs. | good |
| 11-11 | 144 hrs. | good. |

Results:

| Time (hrs.) | $pO_2$ | Crude Wgt (g) | Sample Wgt (g) | % Purity | Yield (g) |
|---|---|---|---|---|---|
| 24 | 68 | 2.32 | 0.19 | 86.0 | 0.14 |
| 32 | 60 | 2.28 | 0.21 | 93.0 | 0.2 |
| 48 | 82 | 1.63 | 0.26 | 98.0 | 0.25 |
| 56 | 86 | 1.51 | 0.19 | 98.6 | 0.187 |
| 72 | 92 | 1.43 | 0.20 | 98.7 | 0.197 |
| 80 | 93 | 1.58 | 0.37 | 88.0 | 0.325 |
| 144 | 92 | 1.14 | 0.31 | 55.0 | 0.17. |

(xi)
Media: 0.1% Yeast extract
0.1% Beef extract
0.4% $NH_4NO_3$
0.02% TWEEN ® 80
0.05% Antifoam
3% Castor oil.
Inoculated with: 3% *Candida petrophilum*, ATCC 20226
64 Hr. shake flask culture.
Fermentation Conditions: 27° C., 420 RPM
pH = 6.5
aeration rate = 40
antifoam added as needed.
100 ml Samples taken at following times:

| Date | Time | Growth |
|---|---|---|
| 11-19 | 24 hr. | good |
| 11-19 | 32 hr. | good |
| 11-20 | 48 hr. | good |
| 11-10 | 56 hr. | good |
| 11-21 | 72 hr. | good |
| 11-21 | 80 hr. | good |
| 11-22 | 96 hr. | good |
| 11-22 | 101 hr. | good |

Results

| Time (hrs.) | $pO_2$ | Crude Wgt (g) | Sample Wgt (g) | % Purity | Yield (g) |
|---|---|---|---|---|---|
| 24 | 28 | 2.36 | 0.14 | 89.7 | 0.126 |
| 32 | 36 | 1.70 | 0.14 | 80.0 | 0.112 |
| 48 | 58 | 1.36 | 0.21 | 93.5 | 0.196 |
| 56 | 58 | 1.79 | 0.35 | 88.6 | 0.316 |
| 72 | 74 | 1.67 | 0.29 | 77.0 | 0.223 |

| | | | | | | |
|---|---|---|---|---|---|---|
| 80 | 78 | 1.44 | 0.30 | 78.6 | 0.236 | |
| 96 | 90 | 1.54 | 0.36 | 72.1 | 0.26 | |
| 101 | 90 | 1.61 | 0.33 | 69.7 | 0.230 | |

(xii)

Media: 0.1% Yeast extract
0.1% Beef extract
0.2% NH$_4$NO$_3$
0.02% TWEEN ® 80
0.05 Antifoam
3% Castor oil.
Inoculated with: 3% *Candida deophila*, ATCC 20177
24 Hrs. Shake flask culture.
27° C., 420 RPM, aeration rate = 40, pH = 6.5.
Procedure followed for each 100 ml sample.

| Date | Time | Growth | pO$_2$ | Crude Wt (g) | Sample Wt (g) | % Purity | Yield (g) |
|---|---|---|---|---|---|---|---|
| 1-8 | 24 | good | 67 | 2.38 | 0.27 | 76.48 | 0.21 |
| 1-8 | 32 | good | 30 | 2.35 | 0.09 | 94.43 | 0.085 |
| 1-9 | 48 | good | 78 | 1.69 | 0.16 | 46.41 | 0.07 |
| 1-9 | 56 | good | 80 | 1.79 | 0.11 | 51.2 | 0.06 |
| 1-10 | 72 | good | 81 | 1.47 | 0.06 | 73.34 | 0.04 |
| 1-10 | 77 | good | 82 | 1.40 | 0.08 | 54.28 | 0.04 |

(xiii)

Media: 0.1% Beef extract
0.1% Yeast extract
0.2% NH$_4$NO$_3$
0.02% TWEEN ® 80
0.05% Antifoam
5% Castor oil.
Inoculated with: 3% *Candida oleophila*, ATCC 20177
24 hr. shake flask culture.
27° C., 420 RPM, pH = 6.5, aeration rate = 40.
Procedure for each 100 ml sample.

| Date | Time | Growth | pO$_2$ | Crude Wt (g) | Sample Wt (g) | % Purity | Yield (g) |
|---|---|---|---|---|---|---|---|
| 1-15 | 24 | good | 69 | 2.40 | 0.03 | 98.52 | 0.03 |
| 1-15 | 32 | good | 74 | 2.39 | 0.09 | 97.51 | 0.09 |
| 1-16 | 48 | good | 80 | 3.15 | 0.16 | 98.99 | 0.159 |
| 1-16 | 57 | good | 78 | 1.86 | 0.02 | 98.63 | 0.02 |
| 1-17 | 72 | good | 78 | 3.30 | 0.11 | 98.51 | 0.108 |
| 1-17 | 77 | good | 77 | 2.06 | 0.10 | 98.49 | 0.1 |

(xiv)

Media: 0.1% Beef extract
0.1% Yeast extract
0.2% NH$_4$NO$_3$
0.02 TWEEN ® 80
0.05% Antifoam
5% Castor oil.
Inoculated with: 3% *Candia olephila*, ATCC 20177
24 Hr. Shake flask culture.
27° C., 420 RPM, pH = 6.5, aeration rate = 40.
Procedure followed for each 100 ml sample.

| Date | Time | Growth | pO$_2$ | Crude Wt (g) | Sample Wt (g) | % Purity | Yield (g) |
|---|---|---|---|---|---|---|---|
| 1-22 | 24 | good | 91 | 3.29 | 0.06 | 98.02 | 0.059 |
| 1-22 | 31 | good | 93 | 3.52 | 0.08 | 99.62 | 0.08 |
| 1-23 | 48 | good | 95 | 3.23 | 0.16 | 88.63 | 0.14 |
| 1-23 | 56 | good | 95 | 3.85 | 0.18 | 78.54 | 0.14 |
| 1-24 | 72 | good | 97 | 3.66 | 0.19 | 75.92 | 0.14 |
| 1-24 | 76 | good | 97 | 3.65 | 0.15 | 81.28 | 0.12. |

(xv)

Media: 0.1% Beef extract, 0.1% yeast extract, 0.4% NH$_4$NO$_3$,
0.02% TWEEN ® 80, 0.05% antifoam, 5% Castor oil.
27° C., 420 RPM, aeration rate = 40.
Procedure for each 100 ml sample.
Inoculated with 3%, 24 hrs. shake flask cultures.
*Candida petrophilum*, ATCC 20226.

| Date | Time | Growth | pO$_2$ | Crude Wt (g) | Sample Wt (g) | % Purity CBW | OVI | Yield (g) |
|---|---|---|---|---|---|---|---|---|
| 1-29 | 24 | good | 10 | 2.26 | 0.06 | 57.9 | 56.9 | 0.03 |
| 1-29 | 31 | good | 10 | 3.15 | 0.15 | 70.6 | 70.8 | 0.11 |
| 1-30 | 48 | good | 40 | 2.10 | 0.17 | 74.3 | 75.2 | 0.13 |
| 1-30 | 56 | good | 45 | 2.84 | 0.19 | 86.7 | 87.7 | 0.17 |
| 1-31 | 72 | good | 40 | 3.16 | 0.24 | 72.8 | 73.6 | 0.18 |
| 1-31 | 77 | good | 50 | 2.87 | 0.06 | 79.3 | 82.4 | 0.05 |

*Candidia oleophila*, ATCC 2107

| | | | | Crude | Sample | % Purity | | Yield |

-continued

| Date | Time | Growth | pO$_2$ | Wt (g) | Wt (g) | CBW | OVI | (g) |
|------|------|--------|--------|--------|--------|------|------|------|
| 1-29 | 24 | good | 30 | 1.70 | 0.04 | 83.7 | 85.7 | 0.03 |
| 1-29 | 31 | good | 6 | 4.51 | 0.10 | 56.0 | 57.4 | 0.06 |
| 1-30 | 48 | good | 35 | 3.42 | 0.05 | 79.1 | 80.1 | 0.04 |
| 1-30 | 56 | good | 35 | 4.27 | 0.06 | 37.6 | 36.8 | 0.02 |
| 1-31 | 72 | good | 30 | 4.58 | 0.08 | 50.9 | 50.2 | 0.04 |
| 1-31 | 77 | good | 33 | 4.54 | 0.06 | 38.9 | 42.1 | 0.02 |

(xvi)

Media: 2% Malt extract, 0.1% peptone, 0.02% TWEEN ® 80,
0.05% antifoam, 5% Castor oil.
27° C., 420 RPM, aeration rate = 40, pH = 6.5.
Inoculated with 3% *Candida petrophilum*, ATCC 20226
24 hour shake flask culture.
Procedure followed for each sample.
100 ml Samples taken at the following times:

| Date | Time | Growth | pO$_2$ | Crude Wt (g) | Sample Wt (g) | % Purity CBW | % Purity OVI | Yield (g) |
|------|------|--------|--------|--------------|---------------|--------------|--------------|-----------|
| 2-12 | 24 | good | 75 | 3.34 | 0.08 | 78.8 | 89.4 | 0.06 |
| 2-12 | 30 | good | 77 | 3.27 | 0.23 | 63.2 | 62.1 | 0.14 |
| 2-13 | 48 | good | 74 | 3.19 | 0.11 | 69.1 | 65.4 | 0.07 |
| 2-13 | 56 | good | 73 | 4.00 | 0.19 | 74.2 | 68.4 | 0.13 |
| 2-14 | 72 | good | 70 | 3.56 | 0.18 | 78.7 | 77.0 | 0.14 |
| 2-14 | 77 | good | 71 | 3.24 | 0.25 | 75.4 | 72.8 | 0.18 |

(xvii)

Media: 2% Malt extract, 0.1% peptone, 0.02% TWEEN ® 80,
0.05% antifoam, 5% castor oil.
27° C., 420 RPM, aeration rate = 40, pH = 6.5.
Inoculated with 3% *Candidia oleophila*, ATCC 21077
24 hr. shake flask culture.
Procedure followed for each sample.

| Date | Time | Growth | pO$_2$ | Crude Wt (g) | Sample Wt (g) | % Purity CBW | % Purity OVI | Yield (g) |
|------|------|--------|--------|--------------|---------------|--------------|--------------|-----------|
| 2-19 | 24 | good | 90 | 2.39 | 0.05 | 17.6 | 17.2 | 0.01 |
| 2-19 | 30 | good | 90 | 3.20 | 0.07 | 7.2 | 6.9 | 0.005 |
| 2-20 | 48 | good | 96 | 3.86 | 0.06 | 77.0 | 72.3 | 0.04 |
| 2-20 | 55 | good | 97 | 2.64 | 0.03 | 2.8 | 2.8 | 0.0008 |
| 2-21 | 72 | good | 97 | 2.80 | 0.04 | 19.1 | 18.2 | 0.007 |
| 2-21 | 77 | good | 97 | 2.89 | 0.03 | 0.3 | 0.3 | 0.00009 |

(xviii)

Media: Malt extract 3 g/L, Peptone 5 g/L, yeast extract 3 g/L
26° C., 200 RPM.
Substrate: 2% Castor oil.

| | 3-6 | | 3-7 | | 3-10 | | 3-11 | | 3-12 |
|---|---|---|---|---|---|---|---|---|---|
| | pH | Lact | pH | Lact | pH | Lact | pH | Lact | Lact |
| *Penicillium aurantiogris* #34613 | 6.0 | − | 5.5 | − | 6.0 | − | 6 | − | − |
| *Penicillium chrysogenum* #100026 | 5.0 | − | 6.0 | − | 5.5 | − | 6 | − | − |
| *Proteus mitajiri* #21136 | 8.0 | − | 8.0 | − | 7.0 | − | 8.0 | − | − |
| *Serratia grimesii* # E 14460 | 6.5 | − | 6.0 | + | 6.0 | − | 6.0 | − | − |
| *Serratia liquefaciens* #11367 | 6.5 | − | 7.0 | − | 6.0 | − | 6.0 | − | − |
| *Xanthomonas campestris* #19155 | 6.0 | + | 6.0 | + | 8.0 | − | 8.5 | − | − |
| *Rhodococcus* sp.#21504 | 5.5 | − | 6.0 | + | 6.0 | + | 6.0 | + | + |
| *Rhodococcus* sp.#21507 | 6.0 | − | 5.5 | − | 7.0 | + | 7.5 | + | + |
| *Rhodococcus* sp. #21508 | 6.0 | − | 60 | − | 6.0 | + | 6.0 | − | − |

(xix)

Media: Malt extract 3 g/L, Peptone 5 g/L, yeast extract 3 g/L
26° C., 200 RPM.
Substrate: 0.5% Castor oil hydrolysate.

| | 3-6 | | 3-7 | | 3-10 | | 3-11 | | 3-12 | | 3-14 | |
|---|---|---|---|---|---|---|---|---|---|---|---|---|
| | pH | Lac | pH | Lac | pH | Lac | pH | Lac | pH | Lac | pH | Lac |
| *Penicillium aurantiogris* #34613 | 6 | − | 6 | − | 7 | − | 7.5 | − | − | − | − | − |
| *Penicillium chrysogenum* #100026 | 6 | − | 6 | − | 5.5 | + | 7 | + | − | + | 4 | − |
| *Proteus mitajiri* #21136 | 6 | − | 6.5 | + | 7 | − | 7 | − | − | − | − | − |
| *Serratia grimesii* # E14460 | 6.5 | + | 7.5 | − | 8.5 | − | 8 | − | − | − | − | − |
| *Serratia liquefaciens* #11367 | * | − | ** | | 5 | + | 4.5 | + | 4.5 | − | | |
| *Xanthomomonas campestris* #191556 | 6 | − | 7 | − | 8 | + | 8.5 | − | − | − | − | − |
| *Rhodococcus* sp. #21504 | 6 | − | 6 | − | 6 | − | 6 | − | − | − | − | − |
| *Rhodococcus* sp. #21507 | 6 | − | 6 | − | 6 | + | 6 | − | − | + | − | − |
| *Rhodococcus* | 6 | − | * | | ** | | 6 | + | 6 | − | 6 | − |

-continued sp. #21508

*Flask broke.
**Inoculate.

(xx)

Media: 2% Beef extract
0.2% Yeast extract
0.02% TWEEN ® 80
0.05% Antifoam
3% Castor Oil
Temperature: 27° C.
RPM: 420
Flow: 0.5 v/v/m
ph = 6.5
Inoculum: 3% *Candida petrophilum.* ATCC 20226

| Time | Crude Wt | Distilled Wt | % Purity | Yield (g/L) | $dO_2$ |
|---|---|---|---|---|---|
| 24 hr. | 1.9 g | 0.25 | 96.11 | 2.4 | 14 |
| 30 | 1.0 | 0.20 | 94.17 | 1.9 | 24 |
| 48 | 1.0 | 0.39 | 30.45 | 1.2 | 64 |
| 56 | 1.0 | 0.17 | 96.25 | 1.8 | 81 |
| 72 | 0.78 | 0.1 | 91.96 | 0.9 | 86 |
| 96 * | 0.2 | 0.17 | 37.35 | 0.6 | 95 |

100 ml Samples: Centrifuge
Extract 3X, 100 ml ethyl acetate each time
Wash with sat'd NaCl (50 ml)
Wash with sat'd naHCO$_3$ 3X (20 ml each time)
Wash with sat'd NaCl 3X (50 ml each time)
Dry over anhydrous sodium sulfate
Evaporate solvent
Distill 225° C., 1 mm/Hg..

(xxi)

Media: 2% Beef extract C-2 10L
0.1% Yeast extract
0.02% TWEEN ® 80
0.05% Antifoam
3% Castor Oil.
Temperature = 27° C.
Agitation = 420 RPM.
Flow = 0.5 v/v/m
pH = 6.5
Inoculum: 3% *Candida petrophilum*
200 ml Samples taken, acidify w/H$_2$SO$_4$ pH = 1.5, reflux 30 min.

| Time | Crude Wt | Distilled Wt | % Purity | Yield(g/L) |
|---|---|---|---|---|
| 24 hr. | 0.9 g | 0.17 g | 94.0 | 0.94 g/L |
| 30 | 1.71 | 0.33 | 92.36 | 1.52 |
| 48 | 1.2 | 0.19 | 95.04 | 0.90 |
| 54 | 1.2 | 0.21 | 85.29 | 0.9 |
| 72 | 1.0 | 0.14 | 41.21 | 0.29 |

For each sample: Centrifuge
Extract 3X, 1:1 solvent to broth
Wash with sat'd NaCl
Wash with sat'd NaHCO$_3$ (3X)
Wash with sat'd NaCl (3X)
Dry over anhydrous sodium sulfate
Evaporate solvent
Distill 225° C., 1 mm/Hg., 2 hours.

(xxii)
C-3 10L

Media: 2% Beef extract
0.1% Yeast extract
0.02% TWEEN ® 80
0.05% Antifoam
3% Castor Oil.
Flow = 1 v/v/m
Temperature = 27° C.
Agitation = 420 RPM
pH = 6.5
Inoculum: 3% *Candida petrophilum*, ATCC 20226
200 ml Samples.

| Time | $dO_2$ | Crude Wt | Distilled Wt. | % Purity | Yield (g/L) |
|---|---|---|---|---|---|
| 24 hr | 17 | 5.7 | 0.44 | 92.18 | 2.03 |
|  |  |  | 0.37 | 94.07 |  |
| 30 | 37 | 5.8 | 0.31 | 92.78 | 3.52 |
|  |  |  | 0.66 | 9.91 |  |
|  |  |  | 0.28 | 93.15 |  |
| 48 | 66 | 7.8 | 0.12 | 92.05 | 2.54 |
|  |  |  | 1.44 | 9.45 |  |

-continued (xxiii)
C-2 10L

Media: 2% Beef extract
0.1% Yeast extract
3% Castor Oil
0.02% TWEEN ® 80
0.05% Antifoam.
pH = 6.5
Flow = 1 v/v/m
Temperature = 27° C.
420 RPM
Inoculum: 3% *Candida petrophilum*, ATCC 20226

| Time | dO$_2$ | Crude Wt. | Distilled Wt | % Purity | Yield (g/L) |
|---|---|---|---|---|---|
| 23 | | 0.9 g | 0.22 g | 94.12 | 2.07 |
| 28 | | 2.1 g | 0.30 g | 77.49 | 2.32 |

(xxiv)

Media: 2% Beef extract
0.1% Yeast extract
5% Castor Oil
0.02% TWEEN ® 80
0.05% Antifoam.
ph = 6.5
Air flow = 1 v/v/m
Temperature = 27° C.
Agitation = 420 RPM
Inoculum: 3% *Candida petrophilum*, ATCC 20226
100 ml Samples.

| Time | dO$_2$ | Crude Wt. | Distilled Wt. | % Purity | Yield (g/L) |
|---|---|---|---|---|---|
| 21 hr. | | 5.8 g | 0.29 g | 87% | 2.52 |
| 26 hr. | | 7.2 g | 0.55 g | 92.13% | 5.01 |
| 45 hr. | | 4.8 g | 0.34 g | 87.01% | 2.96 |
| 50 hr. | | 7.2 g | 0.48 g | 61.76% | 2.96 |

(xxv)

| Medium: C-1 | C-2 | pH = 6.5 |
|---|---|---|
| 4 g/L (NH$_4$)$_2$SO$_4$ | 2% Beef extract | Back pressure = 7.5 psi |
| 0.04 g/L FeSO$_4$ | 0.1% Yeast Extract | Aeration = 0.25 v/v/m |
| 1 g/L Yeast extract | | Agitation = 300 RPM |
| 1 g/L Beef extract | 0.02% TWEEN ® 80 | Temperature: 27° C. |
| 1 g/L KH$_2$PO$_4$ | 5% Castor oil | |
| 0.5 g/L MgSO$_4$.7 H$_2$O | | |
| 0.1 g/L Primagen | | |
| 0.2 g/L TWEEN ® 80 | 3% Inoculum | |
| 5% Castor Oil. | *Candida petrophilum*, ATCC 20226 | |

| | Time | Crude Wt. | Distilled Wt. | % Purity | (g/L) |
|---|---|---|---|---|---|
| C-1 | 24 hr. | 4.4 g | 0.2 g | 83.03 | 1.66 |
| C-2 | 24 | 4.6 | 0.17 | 95.05 | 1.62 |
| C-1 | 29 | 5.8 | 0.2 | 84.38 | 1.69 |
| C-2 | 29 | 3.6 | 0.21 | 91.6 | 1.92 |
| C-1 | 31.5 | 1.3 | 0.17 | 67.01 | 1.14 |
| C-2 | 31.5 | 4.8 | 0.21 | 87.3 | 1.83 |

(xxvi)

Medium: C-2           pH = 6.5
2% Beef extract       Back pressure = 7.5 psi
0.1% Yeast extract    Aeration = 0.5 v/v/m
0.01% KH$_2$PO$_4$    Agitation = 400 RPM
0.005% MgSO$_4$.7 H$_2$O   Temperature = 27° C.
0.02% TWEEN ® 80      3% Inoculum *Candida petrophilum*, ATCC 20226
4% Castor Oil.

| Time Hr. | Crude Wt. | Distilled Wt. | % Purity | (g/L) | dO$_2$ |
|---|---|---|---|---|---|
| 24 | 4.6 g | 0.281 g | 89.4 | 2.5 | 35 |
| 30 | 4.6 | 0.172 | 85.16 | 1.46 | 45 |
| | 1 g lipase, 15 Castor Oil added. | | | | |
| 32 | 5.3 | 0.334 | 13.68 | 0.46 | 2.19  22 |
|    |     | 0.200 | 86.47 | 1.73 |           |
| 37 | ½% Castor Oil added | | | | |
| 19 | | | | | |
| 48 | 8.5 | 0.210 | 89.27 | 1.87 | 46 |

Total NaOH added = 92.8 g
Total antifoam added = 600 ml
Phosphoric acid used = 188 g.

(xxvii)

-continued

| | Medium: C-1 | pH = 6.5 | | | |
|---|---|---|---|---|---|
| | 2% Beef Extract | Back pressure = 7.5 psi | | | |
| | 0.1% Yeast extract | Agitation = 400 RPM | | | |
| | 0.01% KH₂ PO₄ | Temperature = 27° C. | | | |
| | 0.005% MgSO₄.7 H₂O | Aeration = 0.5 v/v/m | | | |
| | 4% Castor Oil. | | | | |
| | 0.02% TWEEN ® 80 | 3% inoculum *Candida petrophilum*, ATCC 20226. | | | |
| Time Hr | Crude Wt. | Distilled Wt. | % Purity | (g/L) | dO₂ |
| 23 | 3.8 g | 0.274 g | 83.81 | 2.3 | 13 |
| 30 | 5.4 | 0.342 | 78.00 | 2.67 | 58 |
| | Add 0.2% capric Acid, lower pH = 6, lower aeration 0.25 v/v/m. | | | | |
| 42 | 4.2 | 0.15 | 56.25 | 0.84 | 58 |

Total NaOH added = 77.3 g
Total antifoam added = 300.5 g
Phosphoric acid used = 595 g.

(xxviii)

| | Medium: 2% Beef extract | C-1 | | | pH = 6.5 |
|---|---|---|---|---|---|
| | 0.1% Yeast extract | 4% Castor oil | | | 400 RPM |
| | 0.01% KH₂ PO₄ | C-2 | | | 27° C. |
| | 0.005% MgSO₄.7 H₂O | | | | |
| | 0.02% TWEEN ® 80 | | | | 0.5 v/v/m |
| | 3% Inoculum *Candida petrophilum*, ATCC 20226 | | | | |
| | Time Hr | Crude Wt. | Distilled Purity | % (g/L) | Yield dO₂ |
| C1 | 16 | 4.6 g | 0.12 g | 79.36 | 0.95 | 0 |
| C2 | 16 | 3.1 | 0.14 | 52.8 | 0.74 | 32 |
| C1 | 24 | 5.9 | 0.11 | 74.03 | 0.81 | 8 |
| C2 | 24 | 2.9 | 0.29 | 24.33 | 0.71 | 8 |
| | 0.05% Capric Acid added to each fermenter. | | | | |
| C1 | 30 | 5.7 | 0.21 | 63.39 | 1.33 | 31 |
| C2 | 30 | 2.7 | 0.24 | 5.39 | 0.13 | 18 |
| | Total NaOH added: | | | Total antifoam added: | |
| | C1 | 134 g | | C1 | 293 g |
| | C2 | 60 g | | C2 | 171 g. |

(xxix)

| | 800 L | | pH = 6.5 | |
|---|---|---|---|---|
| | 2% Beef extract | | Temperature = 27° C. | |
| | 0.1% Yeast extract | | | |
| | 0.02% KH₂ PO₄ | | | |
| | 0.005% MgSO₄.7 H₂O | | | |
| | 0.2% TWEEN ® 80 | | | |
| | 0.05% Antifoam | | | |
| | 4% Castor Oil | | | |
| | Inoculum 3% *Candida petrophilum*, ATCC 20226 | | | |
| Time Hr. | Crude Wt. | Distilled Wt. | % Purity | g/L |
| 22 | 3 g | 0.26 g | 3.03 | 0.08 |
| 24 | 2.9 | 0.20 | 3.48 | 0.07 |
| 30 | 2.3 | 0.28 | 75.45 | 2.11 |

(xxx)

| | C-1 | 2% Beef extract | C-2 | 2% Beef extract |
|---|---|---|---|---|
| | | 0.2% Yeast extract | | 0.5% Yeast extract |
| | | 0.1% KH₂ PO₄ | | 0.1% KH₂ PO₄ |
| | | 0.05% MgSO₄.7 H₂O | | 0.05% MgSO₄.7 H₂O |
| | | 0.02% TWEEN ® 80 | | 0.02% TWEEN ® 80 |
| | | 0.05% Antifoam | | 0.05% Antifoam |
| | | 0.05% Castor Oil | | 5% Castor Oil |
| | Inoculum: | 3% *Candida petrophilum*, ATCC 20226 (1% Olive Oil) | | |
| | 27° C. | pH = 6.5 | | |
| | 400 RPM | 7.5 psi | | |
| | 0.5 v/v/m | | | |
| | Time Hr. | Crude Wt. | Distilled Wt. | % Purity | Yield (g/L) | dO₂ |
| 24 Hr | C1 | 7.7 g | 0.21 g | 72.27 | 1.52 | 47 |
| | C2 | 8.3 | 0.22 | 89.49 | 1.97 | 2 |
| 30 Hr | C1 | 8.7 | 0.38 | 38.65 | 3.6 | 60 |
| | | | 0.22 | 96.7 | | |
| | C2 | 8.7 | 0.40 | 19.4 | 0.78 | 9 |
| 32 Hr | C1 | 8.8 | 0.25 | 54.64 | 4.67 | 62 |
| | | | 0.345 | 95.7 | | |
| 35 Hr | C2 | 10.5 | 0.25 | 85.52 | 2.14 | 24 |
| | Total NaOH added: | | | Total Antifoam added: | | |
| | C1 | 131 g | | C1 = 566 g | | |
| | C2 | 131 g | | C2 = 765 g | | |

(xxxi)

800 L
2% Beef extract

-continued 0.1% Yeast extract
0.01% $KH_2PO_4$
0.005% $MgSO_4.7 H_2O$
0.02% TWEEN ® 80
0.05% Antifoam
5% Castor Oil
3% Inoculum *Candida petrophilum*, ATCC 20226 (1% Olive Oil)

| Time | Crude Wt | Distilled Wt | % Purity | Yield(g/L) |
|---|---|---|---|---|
| 24 hr. | 4.7 g | 0.21 g | 75.79 | 1.59 |
| 29 hr. | 4.6 | 0.322 | 89.66 | 2.89 |
| 32 hr. |  | 0.40 | 66.89 | 2.68 |
| 35 hr. | 4.3 | 0.87 | 5.42 | 0.47 |

(xxxii)
C1 Medium:                          Temperature = 27° C.
3% Beef extract                     Aeration = 0.5 v/v/m
0.1% Yeast extract                  Agitation = 400 RPM
0.1% $KH_2PO_4$                     Backpressue = 7.5 psi
0.05% $MgSO_4.7 H_2O$               pH = 6.0
0.02% TWEEN ® 80
0.05% Antifoam
10% Castor Oil
3% Inoculum *Candida petrophilum*, ATCC 20226 (1% Olive Oil)
100 ml Samples

| Time | Crude Wt | Distilled Wt | % Purity | Yield (g/L) | $dO_2$ |
|---|---|---|---|---|---|
| 24 hr | 9.3 | 0.31 | 32.5 | 3.24 | 9 |
|  |  | 0.24 | 92.83 |  |  |
| 30 hr | 7.0 | 0.62 | 92.8 | 5.75 | 40 |

Total NaOH added = 91 g
Total antifoam added = 32 g (xxxiii)
800 L                               pH = 6.5
Medium:   2% Beef extract           Aeration = 0.5 v/v/m
          0.2% Yeast extract        Temperature = 27° C.
          0.01% $KH_2PO_4$
          0.005% $MgSO_4.7 H_2O$
          0.02% TWEEN ® 80
          0.05% Antifoam
          5% Castor Oil
3% inoculum *Candida petrophilum*, ATCC 20226 (1% Olive Oil)

| Time | Crude Wt | Distilled Wt | % Purity | Yield (g/L) |
|---|---|---|---|---|
| 24 hr | 3.9 g | 0.83 g | 21.54 | 1.79 |
| 30 hr | 3.4 | 0.40 | 90.68 | 3.63 |

(xxxiv)
Medium:   2% Beef extract           Temperature = 27° C.
          0.5% Yeast extract        Aeration = 0.5 v/v/m
          0.1% $KH_2PO_4$           Backpressure = 7.5 psi
          0.05% $MgSO_4.7 H_2O$     Agitation = 400 RPM
          0.02% TWEEN ® 80          C1 pH = 6.0
          0.05% Antifoam            C2 pH = 5.5
          10% Castor Oil
3% Inoculum *Candida petrophilum*, ATCC 20226 (1% Olive Oil)

| | Crude Wt | Distilled Wt | % Purity | Yield g/L | $dO_2$ |
|---|---|---|---|---|---|
| 22 Hrs. | | | | | |
| C1 | 9.5 g | 0.38 g | 64.49 | 2.45 | 12 |
| C2 | 8.2 | 0.40 | 82.21 | 3.29 | 0 |
| 29 Hrs. | | | | | |
| C1 | 9.4 g | 0.65 g / 0.26 g | 11.73 / 88.14 | 0.76 / 2.29 |  |
| C2 | 7.9 g | 0.39 g / 0.32 g | 18.62 / 87.73 | 3.54 | 20 |
| 48 Hrs. | | | | | |
| C1 | 6.0 g | 0.22 | 79.03 | 513 | 35 |
| C2 | 6.6 | 0.36 | 94.12 | | |
| 52 Hrs. | | | | | |
| C1 | 7.6 g | 0.9 / 1.44 | 80.24 / 40.74 | 13.09 | 37 |
| C2 | 6.9 | 0.31 / 0.54 | 80.87 / 16.73 | 3.41 | 36 |

Total NaOH added:                   Total Antifoam added:
C1 = 158 g                          C1 = 27 g FG. 10

| -continued | |
|---|---|
| C2 = 61 g | C2 = 65 g SAG 5693 |

(xxxv)

800 L Pilot Plant  pH = 6
2% Beef extract  Agitation = 75 RPM
0.2% Yeast extract  0.5 v/v/m
0.1% KH$_2$ PO$_4$
0.05% MgSO$_4$.7 H$_2$O
0.02% TWEEN ® 80  3% Inoculum *Candida petrophilum*, ATCC 20226
0.05% Antifoam
10% Castor Oil

| Time | Crude Wt | Distilled Wt | % Purity | Yield (g/L) |
|---|---|---|---|---|
| 24 Hr | 2.0 g | 0.37 g | 60.25 | 2.23 |
| 30 Hr | 8.5 g | 0.55 g<br>0.64 g | 84.61<br>15.33 | 5.63 |

(xxxvi)

C-1 10 L  pH = 6
Medium  2% Beef extract  Agitation = 420 RPM
 0.5% Yeast extract  Aeration = 0.5 v/v/m
 0.1% KH$_2$ PO$_4$  7.5 psi Backpressure
 0.05% MgSO$_4$.7 H$_2$O
 0.02% TWEEN ® 80
 0.05% Antifoam
 10% Castor Oil
3% Inoculum *Candida petrophilum*, ATCC 20226

| Time Hr. | Crude Wt | Distilled Wt | % Purity | Yield (g/L) | | dO$_2$ |
|---|---|---|---|---|---|---|
| 24 Hr | 10.3 g | 0.99 g | 65 | 6.44 | | 1 |
| 30 Hr | 6.7 g | 0.29 g<br>0.29 g | 79<br>25 | 3.4<br>0.73 | 4.13 | 14 |
| 48 Hr | 7.5 g | 0.62 g<br>0.66 g | 84<br>28 | 7.0 | | 42 |
| 52 Hr | 7.3 g | 0.78 g<br>1.04 g | 5.3<br>11 | 1.14 | 6.44 | 44 |

(xxxvii)

800 L - Pilot Plant  pH = 6 Batch 6
Medium:  Agitation = 70 RPM
2% Beef extract  Agitation = 0.5 v/v/m
0.5% Yeast extract
0.1% KH$_2$ PO$_4$
0.05% MgSO$_4$.7 H$_2$O
0.02% TWEEN ® 80
0.05% Antifoam
10% Castor Oil
3% Inoculum *Candida petrophilum*, ATCC 20226

| Time Hr. | Crude Wt | Distill Wt | % Purity | Yield | |
|---|---|---|---|---|---|
| 24 | 9.1 g | 0.94 g | 77 | 3.77 | |
| 32 | 8.5 g | 0.83 g<br>0.58 g | 40<br>37 | 3.32<br>0.21 | 3.53 g/L |
| 48 | 6.8 g | 0.67 g<br>0.88 g | 66<br>11 | 4.42<br>0.97 | 5.39 g/L |
| Final 1-12 48 Hr. | 8.5 g | 0.78 g<br>0.22 g | 74<br>24 | 5.77<br>0.53 | Batch 7<br>1-10-87 |

(xxxviii)

C-3 10 L  pH = 6
Medium:  Agitation = 420 RPM
3% Amberex 5500  Aeration = 0.5 v/v/m
0.1% KH$_2$ PO$_4$  Temperature = 27° C.
0.05% MgSO$_4$.7 H$_2$O
0.02% TWEEN ® 80
0.05% Antifoam
3% Inoculum *Candida petrophilum*, ATCC 20226

| Time | Crude Wt | Distilled Wt | % Purity | Yield | |
|---|---|---|---|---|---|
| 24 Hr | 1.3 g | 0.56 g<br>0.54 g | 60<br>8 | 3.36<br>.43 | 3.79 g/L |
| 40 Hr | 6.8 g | 0.54 g<br>1.42 g | 67<br>27 | 3.62<br>3.83 | 7.45 g/L |

-continued

| | | | | | | |
|---|---|---|---|---|---|---|
| 48 hr | 7.3 g | 0.98 g | 60 | 5.88 | } | 13.08 g/L |
| | | 2.4 g | 30 | 7.2 | | |
| 64 Hr | 5.7 g | 0.68 g | 70 | 4.76 | } | 11.29 g/L |
| | | 2.51 g | 26 | 6.53 | | |

(xxxix)

C-2, C-3 10L  Agitation = 420 RPM
Medium:  Aeration = 0.5 v/v/m
3% Amberex 5500  Temperature = 28° C.
0.1% KH$_2$ PO$_4$  pH C-2 = 6
0.05% MgSO$_4$.7 H$_2$O  pH C-3 = 7
0.02% TWEEN ® 80
0.005% Antifoam (FG-10)
3% Inoculum *Candida petrophilum*, ATCC 20226

| Time | Crude Wt | Distilled Wt | % Purity | Yield (g/L) | dO$_2$ |
|---|---|---|---|---|---|
| 24 Hr. | | | | | |
| C2 | 8.2 g | 0.23 g, 0.71 g | 60.8, 10.2 | 2.12 | 8 |
| C3 | 8.4 g | 0.89 g, 1.36 g | 21.3, 41.15 | 7.5 | 6 |
| 30 Hr. | | | | | |
| C2 | 8.8 g | 0.39 g, 0.53 g | 53.2, 6.31 | 2.40 | 14 |
| C3 | 7.6 g | 0.56 g, 0.93 g | 27.68, 5.52 | 2.06 | 0 |
| 48 Hr. | | | | | |
| C2 | 5.5 g | 0.28, 1.01 g | 50.18, 8.26 | (× 1.19) = | 14 |
| C3 | 4.9 g | | | | 16 |
| 50 Hr. | | | | | |
| C2 | 7.9 g | 0.83 g, 1.07 g | 28.9, 14.45 | 3.95 | 2 |
| C3 | 6.2 g | 0.62 g, 1.9 g | 56,03, 6.42 | 4.69 | 18 |

| Total NaOH added: | Total Antifoam added: | % Purity correct |
|---|---|---|
| C-2 = 213 g | C-2 = 110 g | with internal std. |
| C-3 = 358 g | C-3 = 111 g | |

(xl)

800 L Batch 8
2% Beef Extract
0.5% Yeast extract
0.1% KH$_2$ PO$_4$
0.05% MgSO$_4$.7 H$_2$O
0.02% TWEEN ® 80
0.05% Antifoam

| | Crude | Distilled | % Purity | Yield | | |
|---|---|---|---|---|---|---|
| 48 Hr. | 8.4 g | 0.60 g | 69 | 4.14 | } | 4.95 g/L |
| | | 0.74 g | 11 | 0.81 | | |

1-16 Batch 9 - Temperature controller malfunction

| | | | | | | |
|---|---|---|---|---|---|---|
| 48 Hr. | 8.28 | 0.38 g | 62.4 | 2.37 | } | 2.41 g/L |
| | | 0.32 g | 1.3 | 0.04 | | |

EXAMPLE V

Preparation of Mixture of Lactones

Reactions:

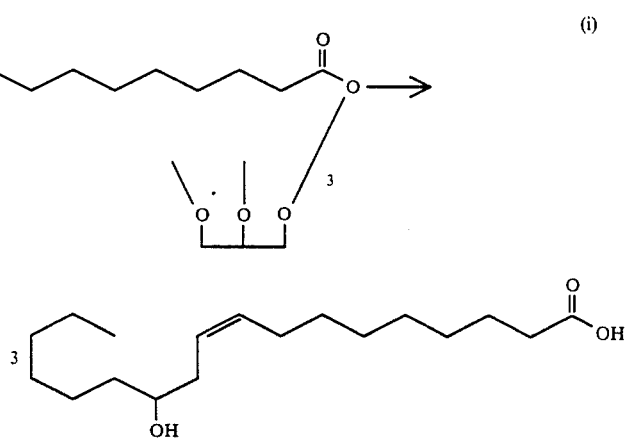

(i)

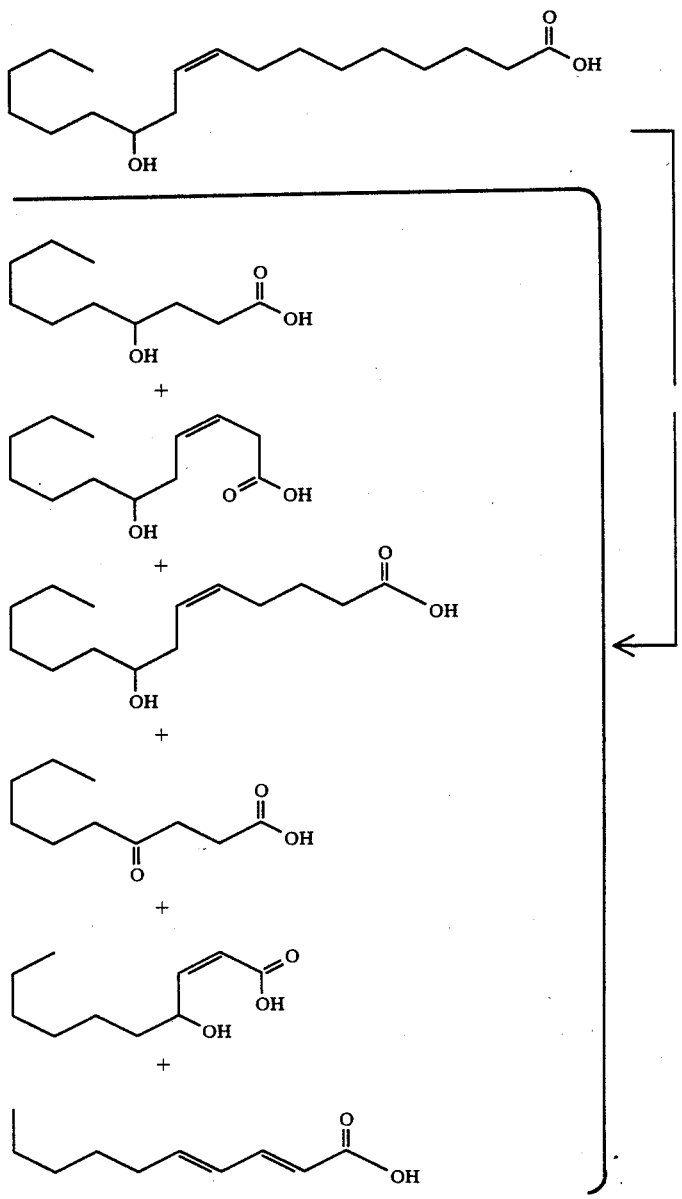
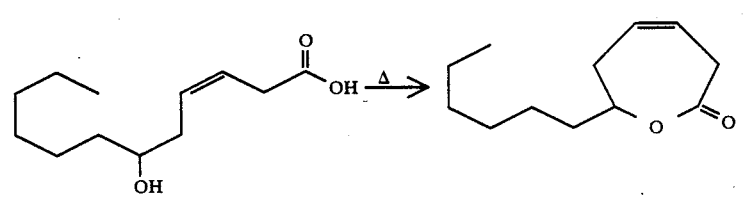
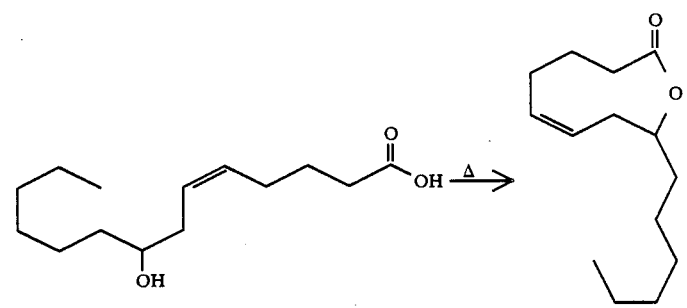

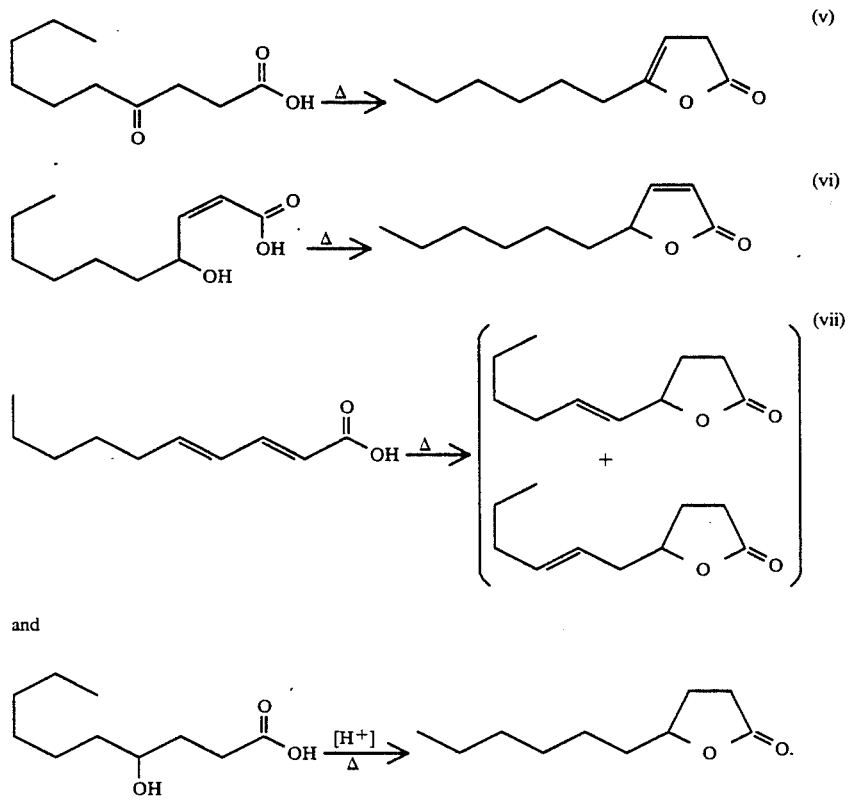

and

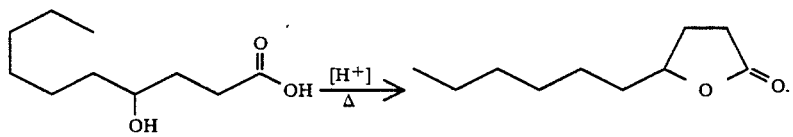

Using the same conditions as Example III a fermentation reaction was carried out. The fermentation batch after extraction and evaporation was distilled on a 12" Goodloe column yielding the following fractions:

| Fraction No. | Vapor Temp. (°C.) | Liquid Temp. (°C.) | Vacuum mm/Hg. Pressure | Reflux Ratio |
|---|---|---|---|---|
| 1 | 188/145 | 183/185 | 16.5/14.5 | 2:1 |
| 2 | 150 | 185 | 14.5 | 2:1 |
| 3 | 153 | 185 | 14.5 | 2:1 |
| 4 | 154 | 186 | 14.0 | 2:1 |
| 5 | 155 | 187 | 14.0 | 2:1 |
| 6 | 155 | 187 | 14.0 | 2:1 |
| 7 | 155 | 189 | 14.0 | 2:1 |
| 8 | 155 | 189 | 14.0 | 2:1 |
| 9 | 155 | 190 | 14.0 | 2:1 |
| 10 | 155 | 191 | 16.0 | 2:1 |
| 11 | 156 | 193 | 16.0 | 2:1 |
| 12 | 156 | 195 | 16.5 | 2:1 |
| 13 | 157 | 196 | 16.5 | 2:1 |
| 14 | 157 | 198 | 16.5 | 2:1 |
| 15 | 157 | 200 | 16.5 | 2:1 |
| 16 | 156 | 204 | 16.0 | 2:1 |
| 17 | 156 | 205 | 16.0 | 2:1 |
| 18 | 154 | 207 | 15.5 | 2:1 |
| 19 | 154 | 210 | 15.0 | 2:1 |
| 20 | 156 | 214 | 15.0 | 2:1 |
| 21 | 160 | 216 | 15.5 | 2:1 |
| 22 | 167 | 220 | 17.0 | 2:1 |
| 23 | 167 | 226 | 17.0 | 2:1 |
| 24 | 171 | 230 | 16.5 | 2:1 |
| 25 | 173 | 236 | 16.5 | 2:1 |
| 26 | 174 | 245 | 16.0 | 2:1 |
| 27 | 174 | 251 | 16.0 | 2:1. |

FIG. 6 is the GLC profile for fraction 23 (Conditions: 50 m×0.31 mm OV-1 column programmed at 75°–225° C. at 2° C. per minute).

FIG. 7 is the GLC profile for fraction 24 of the foregoing distillation.

FIG. 8 is is the GLC profile for fraction 1 of the foregoing distillation. The peak indicated by reference numeral 80 is the peak for the compound having the structure:

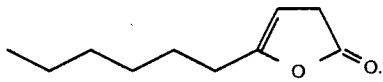

The resulting product has (bulked fractions 2–25) has a lactonic coconut and peach aroma and taste profile at 1 ppm causing it to be useful in coconut, apricot, peach and vanilla-flavored foodstuffs.

EXAMPLE VI

Patchouli Perfume Formulation

The following mixture is prepared:

| Ingredients | Parts by Weight |
|---|---|
| Orange oil | 50 |
| Bergamot oil | 20 |
| Lime oil | 100 |
| Neroli oil | 5 |
| 4-(4-methyl-4-hydroxyamyl)delta[3]-cyclohexene carboxaldehyde | 5 |
| 2,3,3A,4,5,7A-hexahydro-6,7A,8,8-tetramethyl-1,5,methano-1H-inden-1-ol | 100 |

| Ingredients | Parts by Weight |
|---|---|
| (prepared according to the process No. 3,989,760 issued on November 2, 1976) | |
| 1',2',3',4',5',6',7',8'-octahydro 2',3',8',8'-tetramethyl-2'aceto-naphthone isomer mixture produced according to the process of Example VII of Application for U.S. Letters Pat., Serial No. 434,948 filed on January 21, 1974, now U.S. Letters Pat. No. 3,911,018 issued on October 7, 1975 | 50 |
| Gamma methyl ionone | 20 |
| 1-acetyl-2,5,5-trimethylcyclo-heptane produced according to U.S. Pat. No. 3,869,411 issued on March 4, 1975 | 50 |
| Mixture of compounds prepared according to Example I | 150 |

The mixture of lactones prepared according to Example I add to this patchouli formulation a sophisticated, sweet, fruity, peach-like aroma profile with green and herbaceous topnotes.

EXAMPLE VII

Preparation of Soap Compositions

One hundred grams of soap chips are produced according to Example V of U.S. Pat. No. 4,058,487 issued on Nov. 15, 1977, the specification for which is incorporated herein by reference, as follows:

The sodium salt of an equal mixture of $C_{10}$–$C_{14}$ alkane sulfonate (95% active), 40 pounds, is dissolved in a mixture of 80 pounds of anhydrous isopropanol and 125 pounds of deionized water at 150° F. In this mixture is dissolved 10 pounds of partially hydrogenated coconut oil fatty acids and 15 pounds of sodium mono-$C_{14}$ alkyl maleate, and the pH of this solution is adjusted to 6.0 by the addition of a small amount of 50% aqueous solution of sodium hydroxide. The isopropanol is distilled off and the remaining aqueous solution is drum dried. The resulting solid actives are then blended in a chip mixture with 10 pounds of water, 0.2 points of titanium hydroxide and 0.7 pounds of one of the perfume ingredients set forth in Table I below. The chips are then plodded into logs, cut to size and finally stamped into bars having a pH of approximately 6.9.

Each of the perfumed soaps produced by means of the foregoing procedure manifests an excellent aroma as set forth in Table I, infra.

TABLE I

| Ingredient | Fragrance Profile |
|---|---|
| Mixture of compounds produced according to Example I, bulked fractions 1–19. | A peach aroma. |
| Mixture of lactones produced according to Example I, bulked fractions 23–27. | A peach and apricot aroma profile. |
| Perfume composition of Example VI. | A patchouli aroma with peach-like undertones and herbaceous topnotes. |

EXAMPLE VIII

Preparation of a Detergent Composition

A total of 100 grams of a detergent powder prepared according to U.S. Pat. No. 4,058,472 (the specification for which is incorporated by reference herein) and containing 5% by weight of the sodium salts of a mixture of sulfonated $C_{14}$–$C_{18}$ alkyl catechol as a surface active component, the mixture being 60 parts by weight of mono-$C_{14}$–$C_{18}$ alkyl catechol and 40 parts by weight of di-$C_{14}$–$C_{18}$ alkyl catechol, 35% sodium tetrapyrophosphate, 30% sodium silicate, 20% of sodium carbonate, 3% of sodium carboxymethyl cellulose and 7% of starch is mixed with 0.15 grams individually with each of the aroma ingredients set forth in Table I of Example VII until a substantially homogeneous composition is obtained. Each of the compositions has an excellent aroma as set forth in Table I of Example VIII.

EXAMPLE IX

Preparation of a Cosmetic Powder Composition.

A cosmetic powder is prepared by mixing in a ball mill, 100 grams of talcum powder with 0.25 grams of each of the perfume materials of Table I of Example VII. Each of the powders has an excellent aroma as set forth in Table I of Example VI.

EXAMPLE X

Perfumed Liquid Detergent

Concentrated liquid detergents with aromas as set forth in Table I of Example VII are prepared by adding 0.10%, 0.15% and 0.20% of each of the ingredients set forth in Table I of Example VII. They are prepared by adding and homogeneously mixing the appropriate quantity of perfume substance of Table I of Example VII in the liquid detergent. The detergents individually possess aromas as set forth in Table I of Example VII, the intensity increasing with greater concentrations of perfume substance set forth in Table I of Example VII.

EXAMPLE XI

Preparation of a Cologne and Handkerchief Perfume

Each of the ingredients of Table I of Example VII is incorporated individually into colognes of several strengths at concentrations of 2.0%, 2.5%, 3.0%, 3.5%, 4.0% and 5.0% in 75%, 80%, 85%, 90% and 95% aqueous ethanol; and into several concentrations of handkerchief perfumes at the rate of 15%, 20% and 25% (in 80%, 85%, 90% and 95% aqueous ethanol). Distinct and definite aromas as set forth in Table I of Example VII are imparted to the colognes and to the handkerchief perfumes at the several concentrations set forth above.

EXAMPLE XII

Preparation of Soap Compositions

One hundred grams of soap chips (IVORY ® produced by the Proctor & Gamble Company of Cincinnati, Ohio) are admixed with one gram of each of the substances set forth in Table I of Example VII, supra, until homogeneous compositions are obtained. In each of the cases, the homogeneous compositions are heated under 3 atmospheres pressure at 180° C. for a period of three hours and the resulting liquids are placed into soap molds. The resulting soap cakes, on cooling, manifest excellent aromas as set forth in Table I of Example VII.

EXAMPLE XIII

Preparation of Solid Detergent Compositions

Detergents are prepared from the following ingredients according to Example I of Canadian Patent No. 1,007,948, the specification for which is incorporated by reference herein:

| Ingredients | Parts by Weight |
|---|---|
| NEODOL ® 45-11 (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of said detergent is admixed with 0.10, 0.15, 0.20 and 0.25 grams of each of the substances set forth in Table I of Example VII, supra. Each of the detergent samples has an excellent aroma as indicated in Table I of Example VII.

EXAMPLE XIV

Preparation of Drier-Added Fabric Softener Article

Utilizing the procedure of Example I at column 15 of U.S. Pat. No. 3,632,396 the specification for which is incorporated by reference herein, a non-woven cloth substrate useful as a drier-added fabric softening article of manufacture is prepared wherein the substrate, substrate coating and outer coating and the perfume material are as follows:
1. a water "dissolvable" paper ("Dissolve Paper") as the substrate;
2. ADOGEN ® 448 (melting point about 140° F.) as the first substrate coating; and
3. an outer coating having the following formulation (melting point about 150° F.):
   57% $C_{20}$-$C_{22}$ HAPS;
   22% isopropyl alcohol;
   20% antistatic agent; and
   1% of one of the perfumery substances set forth in Table I of Example VII, supra.

Fabric softening compositions containing the substances as set forth in Table I of Example VII, supra, essentially consist of a substrate having a weight of about 3 grams per 100 square inches; a substrate coating weighing about 1.85 grams per 100 square inches of substrate; and an outer coating weighing about 1.5 grams per 100 square inches of substrate are prepared thereby providing a total aromatized substrate and outer coating weight ratio of about 1:1 by weight of the substrate.

The aromas as set forth in Table I of Example VII, supra, are imparted in a pleasant manner to the head space in a drier on operation thereof using the said drier-added fabric softening non-woven fabric by adding to the drying cycle.

As stated above in the case of fabric softener articles, the entire U.S. Pat. No. 3,632,396 is incorporated by reference herein. Thus, all of the articles of U.S. Pat. No. 3,632,396 acting as fabric softening articles in said U.S. Patent may be perfumed in their outer coating with from 0.25% up to 5% by weight of each of the perfuming substances of Table I of Example VII, supra.

EXAMPLE XV

Hair Preparation

A "soft-feel, good-hold" hair spray is produced containing the following ingredients:

| Ingredients | Parts by Weight |
|---|---|
| Polyvinylprrilidones/vinyl acetate "E-735 Copolymer" manufactured by the GAF Corporation of New York, N.Y. | 4.00 |
| Anhydrous ethanol | 70.90 |
| Dioctyl sebecate | 0.05 |
| Benzyl alcohol | 0.05 |
| "Propellant A46" manufactured by the GAF Corporation of New York, N. Y. | 24.95 |
| Fragrance ingredient as set forth in Table I of Example VII, supra. | 0.05 |

The PVP/VA copolymers are first dissolved in alcohol and all other ingredients are added until uniform. The propellant is then pressurized and used as an aerosol. The resulting hair sprays each have pleasant aromas as set forth in Table I of Example VII.

EXAMPLE XVI

Scouring Cleanser Composition

A scouring cleanser composition is prepared in accordance with Example I at columns 11 and 12 of U.S. Pat. No. 4,193,888 issued on Mar. 18, 1980, the specification for which is incorporated by reference herein. To this composition, the substances set forth in Table I of Example VII, supra, are added at the level of 0.25% as set forth in the table in said Example I of U.S. Pat. No. 4,193,888 yielding an aroma on using said cleanser in ordinary circumstances which is quite pleasant and described in Table I of Example XII, supra.

EXAMPLE XVII

A fabric softening article prepared substantially as set forth in Example VIII of Canadian Patent No. 1,069,260, the specification for which is incorporated by reference herein, is prepared containing 0.21% by weight of a perfuming substance as set forth in Table I of Example VII, supra, and yielding on use in a drier, a faint aroma as set forth in Table I of Example VII, supra.

EXAMPLE XVIII

Tobacco Flavor Formulations

Cigarettes are produced using the following tobacco formulations:

| Ingredients | Parts by Weight |
| --- | --- |
| Bright | 40.1 |
| Burley | 24.9 |
| Maryland | 1.1 |
| Turkish | 11.6 |
| Stem (flue cured) | 14.2 |
| Glycerine | 2.8 |
| H₂O | 5.3 |

At the rate of 0.2%, the following tobacco formulation is applied to all of the cigarettes produced with the above tobacco formulation:

| Ingredients | Parts by Weight |
| --- | --- |
| Ethyl butyrate | 0.05 |
| Ethyl valerate | 0.05 |
| Maltol | 2.00 |
| Cocoa extract | 26.00 |
| Coffee extract | 10.00 |
| Ethyl alcohol (95%) | 20.00 |
| H₂O | 41.900 |

To portions of 50% of the cigarettes at levels of 10 and 20 ppm, a mixture of lactones produced according to Example II is added. These cigarettes are hereinafter called "experimental" cigarettes. The cigarettes without the mixture of lactones are hereinafter called "control" cigarettes. The control and experimental cigarettes are then evaluated by paired comparison and the results are as follows:

(a) In aroma, the experimental cigarettes are all found to be more aromatic with Turkish tobacco-like nuances.
(b) In smoke flavor, the experimental cigarettes are all found to be more aromatic, more sweet with Turkish tobacco, oriental-like nuances than the control cigarettes.

The experimental cigarettes containing the mixture of lactones are found to be fruity and have pleasant aesthetically pleasing fruity notes in addition.

EXAMPLE XIX

Pudding

At the rate of 0.8 ppm the mixture of lactones produced according to Example V, bulked fractions 4–9 are added to a royal butterscotch pudding. Pleasant aesthetically pleasing peach nuances were added to the butterscotch pudding causing a panel of 30 members to prefer the butterscotch pudding with the mixture of lactones added thereto to a butterscotch pudding without the mixture of lactones added thereto.

What is claimed is:

1. A process for the preparation of a mixture of unsaturated lactones each of which is defined according to the structure:

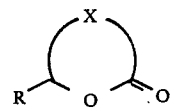

wherein R represents C₆ alkyl or alkenyl; and X represents C₂, C₄ or C₆ alkylene or alkenylene; with the provisos that R is C₆ alkyl when X is C₂, C₄ or C₆ alkenylene and R is C₆ alkenyl when X is C₂, C₄ or C₆ alkylene, said lactones having the structures:

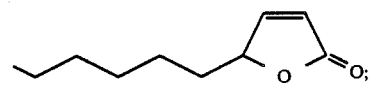

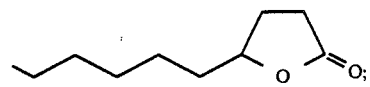

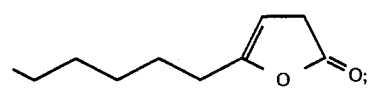

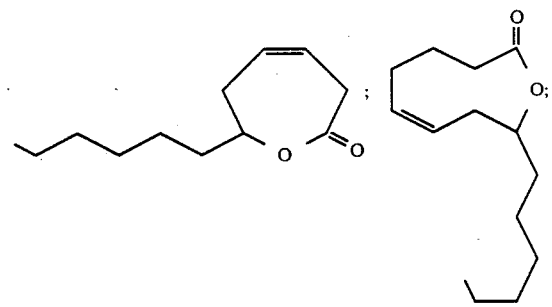

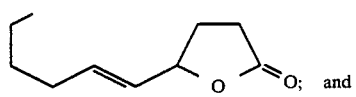

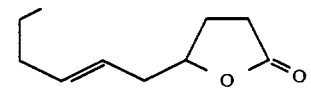

consisting of the sequential steps of:
(i) fermenting at a pH in the range of from about 5.5 up to about 7 and at a temperature in the range of from about 20° C. up to about 35° C., castor oil, a castor oil hydrolysate or ricinoleic acid with a micoorganism selected from the group consisting of:

Candida petrophilum, ATCC 20226;
Candida oleophila, ATCC 20177;
Candida sp., ATCC 20504; and
Candida sake, ATCC 28137 whereby gamma hydroxydecanoic acid and a mixture of other acids defined according to the generic structure:

$$Y-C\begin{matrix}\nearrow O\\ \searrow OH\end{matrix}$$

is formed having the specific structures:

-continued

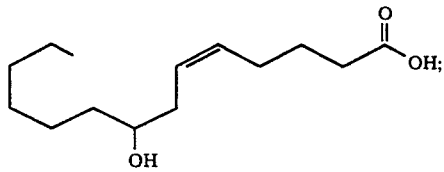

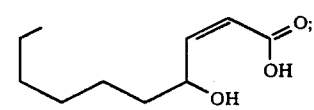

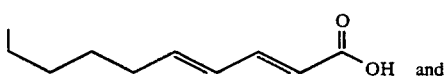 and

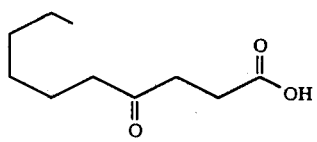

wherein Y represents an oxo-saturated, oxo-unsaturated or di-unsaturated $C_9$, $C_{11}$ or $C_{13}$ moiety according to the reaction:

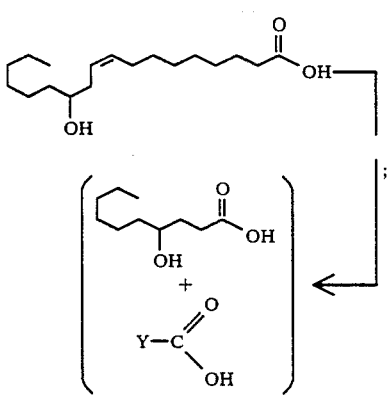

(ii) effecting the lactonization of the resulting gamma hydroxydecanoic acid at a pH in the range of 0–5 and at a temperature in the range of from about 90° C. up to about 120° C. by means of simultaneous acidification and heating according to the reaction:

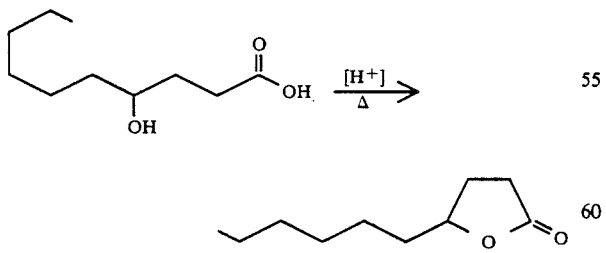

and then
(iii) effecting lactonization by means of distillation at a temperature in the range of 120°–220° C. and at a pH of between about 1 and about 7 of the resulting acids defined according to the structure:

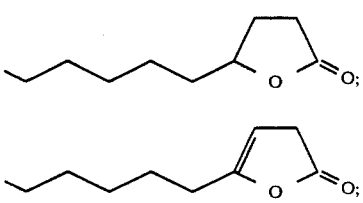

to form the mixture of lactones defined according to the structure:

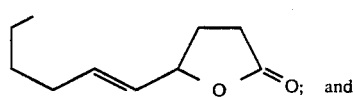

and having the structures:

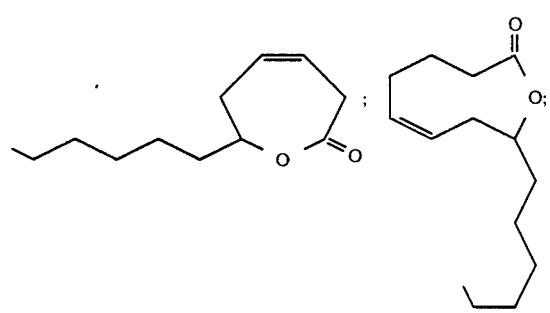

according to the reaction:

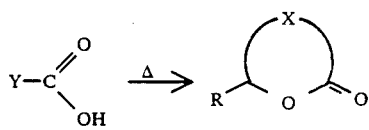

whereby the sum of the number of carbon atoms in the X moiety and in the R moiety is equal to the number of carbon atoms in the Y moiety minus 1.

* * * * *